(12) United States Patent
Grant et al.

(10) Patent No.: US 12,268,776 B2
(45) Date of Patent: Apr. 8, 2025

(54) ENCAPSULATION OF GASTRIC RESIDENCE SYSTEMS

(71) Applicant: Lyndra Therapeutics, Inc., Watertown, MA (US)

(72) Inventors: Tyler Grant, Arlington, MA (US); Erik Robert Waldemar Ryde, Boston, MA (US); Raymond Patrick Knox, Worcester, MA (US); Megan Bishoff, Boston, MA (US)

(73) Assignee: LYNDRA THERAPEUTICS, INC., Watertown, MA (US)

( * ) Notice: Subject to any disclaimer, the term of this patent is extended or adjusted under 35 U.S.C. 154(b) by 0 days.

(21) Appl. No.: 18/470,327

(22) Filed: Sep. 19, 2023

(65) Prior Publication Data

US 2024/0139102 A1    May 2, 2024

Related U.S. Application Data

(62) Division of application No. 16/648,207, filed as application No. PCT/US2018/051816 on Sep. 19, 2018, now Pat. No. 11,793,751.

(60) Provisional application No. 62/561,043, filed on Sep. 20, 2017.

(51) Int. Cl.
| | |
|---|---|
| *A61J 3/07* | (2006.01) |
| *A61K 9/00* | (2006.01) |
| *A61K 9/48* | (2006.01) |
| *A61M 31/00* | (2006.01) |

(52) U.S. Cl.
CPC .......... *A61K 9/0065* (2013.01); *A61K 9/4833* (2013.01); *A61M 31/002* (2013.01)

(58) Field of Classification Search
CPC . A61K 9/0065; A61K 9/4833; A61M 31/002; A61J 3/071; A61J 3/074
See application file for complete search history.

(56) References Cited

U.S. PATENT DOCUMENTS

| | | | |
|---|---|---|---|
| 3,044,599 | A | 7/1962 | Gajda |
| 4,304,767 | A | 12/1981 | Heller et al. |
| 4,758,436 | A | 7/1988 | Caldwell et al. |
| 4,767,627 | A | 8/1988 | Caldwell |
| 5,002,772 | A | 3/1991 | Curatolo et al. |
| 5,081,822 | A | 1/1992 | Boyd |
| 5,277,912 | A | 1/1994 | Lowe et al. |
| 5,443,843 | A | 8/1995 | Curatolo |
| 6,120,803 | A | 9/2000 | Wong et al. |
| 11,793,751 | B2 | 10/2023 | Grant et al. |
| 2010/0115751 | A1 | 5/2010 | Moodley |
| 2015/0150701 | A1 | 6/2015 | Betser et al. |
| 2017/0106099 | A1 | 4/2017 | Bellinger |
| 2020/0281851 | A1 | 9/2020 | Grant et al. |

FOREIGN PATENT DOCUMENTS

| | | |
|---|---|---|
| AU | 645518 B2 | 1/1994 |
| EP | 0415671 A2 | 3/1991 |
| WO | 2006010635 A2 | 2/2006 |
| WO | 2006010635 A3 | 3/2006 |
| WO | 2007083309 A2 | 7/2007 |
| WO | 2007083309 A3 | 9/2007 |
| WO | 2015191920 A1 | 12/2015 |
| WO | 2017093976 A1 | 6/2017 |
| WO | 2017100367 A1 | 6/2017 |

OTHER PUBLICATIONS

Capsule Sizes (Capsugel Lonza Pharma & Biotech, pp. 1-2, accessed on Apr. 19, 2024, accessed from https://www.capsugel.com/cpsl-web/kc/Coni-Snap%C2%AE-Gelatin-Capsule-Sizes.pdf) (Year: 2024).*
Holscot (The Advnatages of Using TeflonTM Coatings, Published Nov. 27, 2018, accessed from https://holscot.com/top-10-advantages-of-teflon-coating-services/, pp. 1-4) (Year: 2018).*
Extended European Search Report, dated Sep. 3, 2021, for European Patent Application No. 18858151.6, 9 pages.
International Preliminary Report on Patentability, issued Mar. 24, 2020, for PCT Application No. PCT/US2018/051816 filed on Sep. 19, 2018, 10 pages.
International Search Report and Written Opinion mailed on Jan. 8, 2019 for PCT Application No. PCT/US2018/051816 filed on Sep. 19, 2018, 19 pages.
Invitation to Pay Additional Fees and, Where Applicable, Protest Fee mailed on Oct. 25, 2018 for PCT Application No. PCT/US2018/051816 filed on Sep. 19, 2018, 2 pages.
Mukherji, G. et al. (2002). "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences vol. 126, New York: Marcel Dekker, 962 pages.
Partial Supplementary European Search Report, dated May 25, 2021, for European Patent Application No. 18858151.6, 10 pages.
Extended European Search Report, dated Jan. 29, 2025, for European Patent Application No. 24213233.0, 8 pages.

* cited by examiner

*Primary Examiner* — Alma Pipic
(74) *Attorney, Agent, or Firm* — MORRISON & FOERSTER LLP

(57) ABSTRACT

Compactable gastric residence systems comprising therapeutic agent formulations for sustained gastric release of therapeutic agents are disclosed, as well as methods and systems for encapsulating such gastric residence systems. The methods and systems for encapsulating the gastric residence systems can be automated from receiving a bulk of gastric residence systems, orienting, placing, compacting, securing, and encapsulating the gastric residence systems.

17 Claims, 33 Drawing Sheets

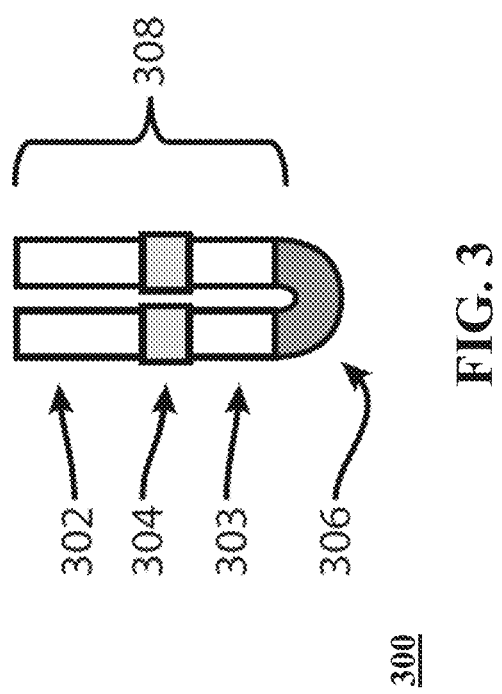

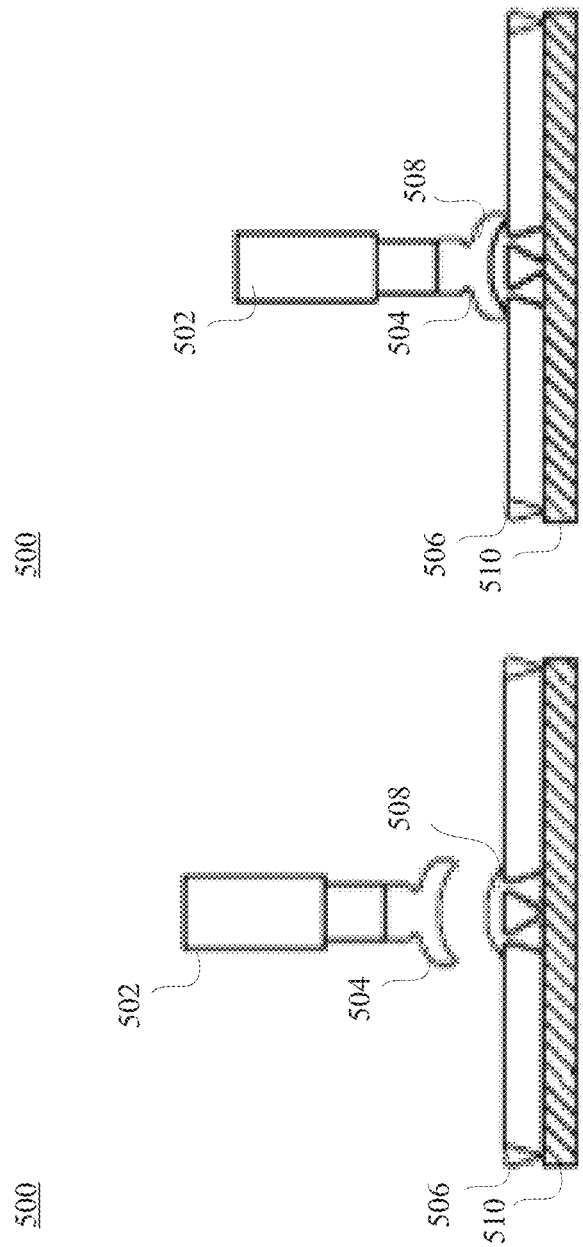

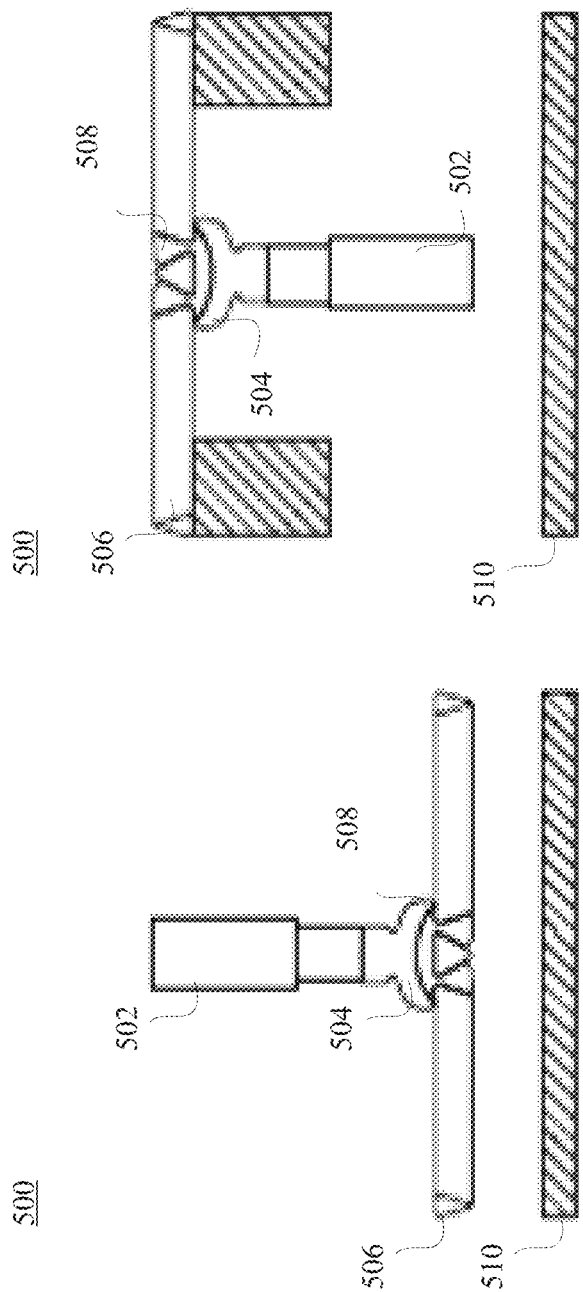

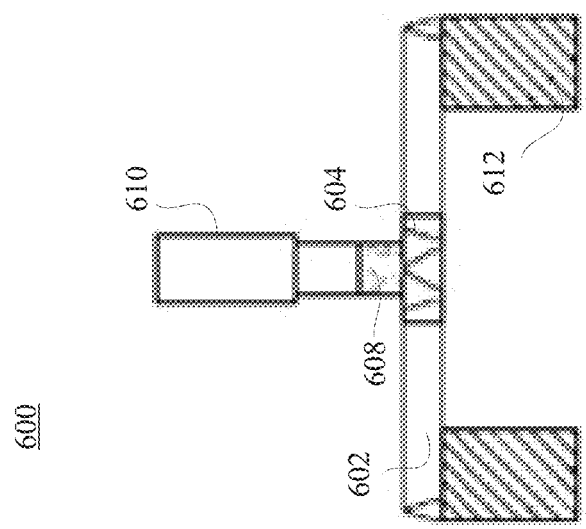
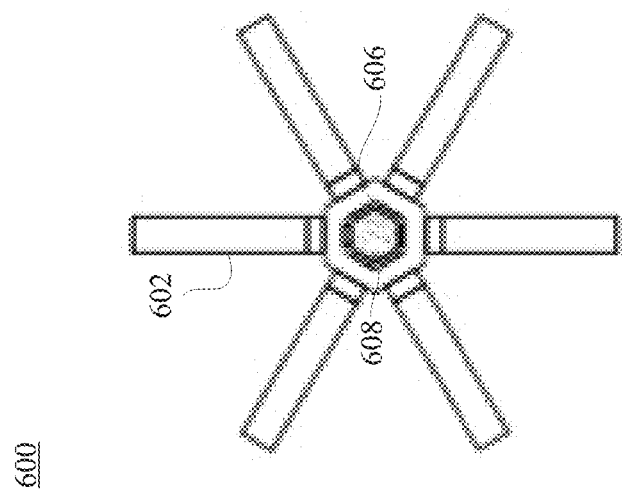
FIG. 6C
FIG. 6D

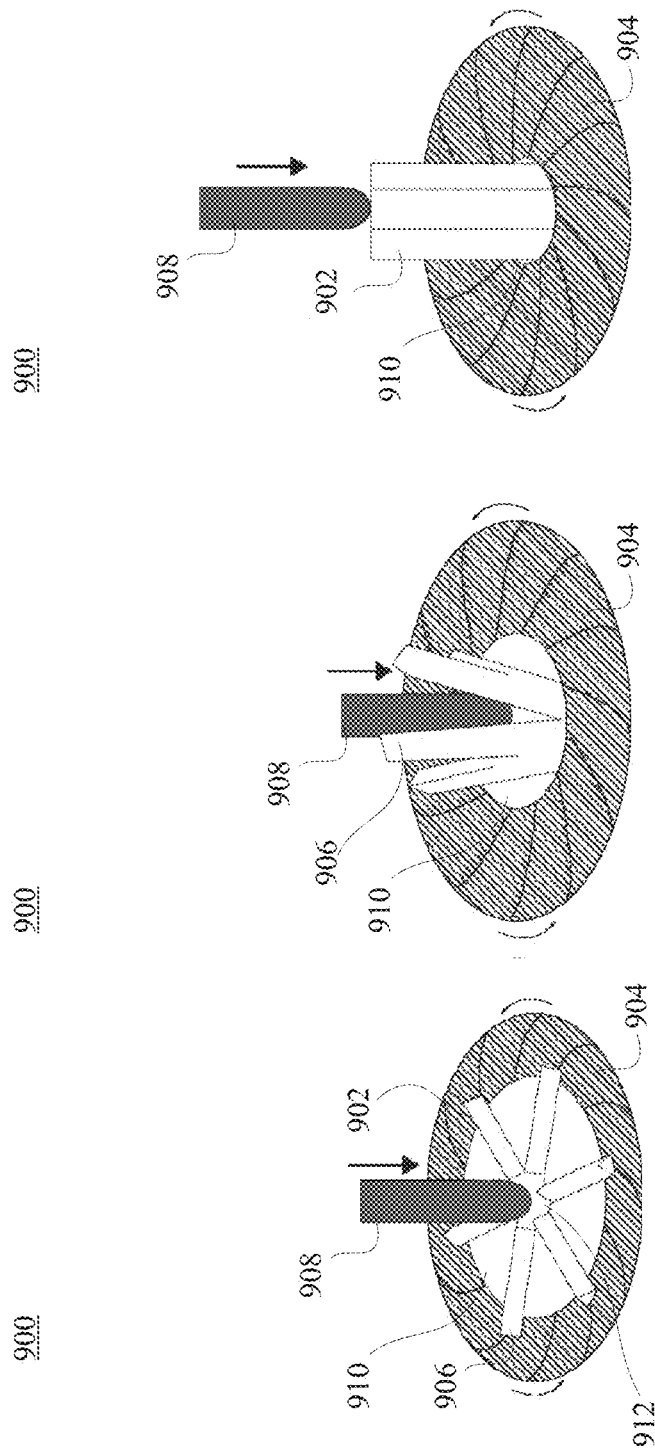

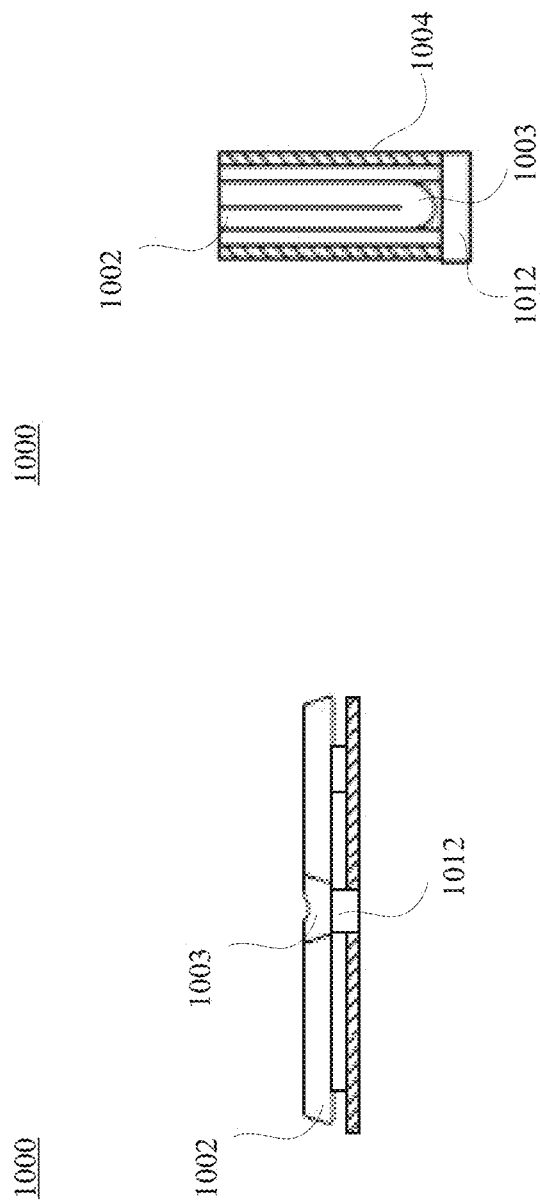

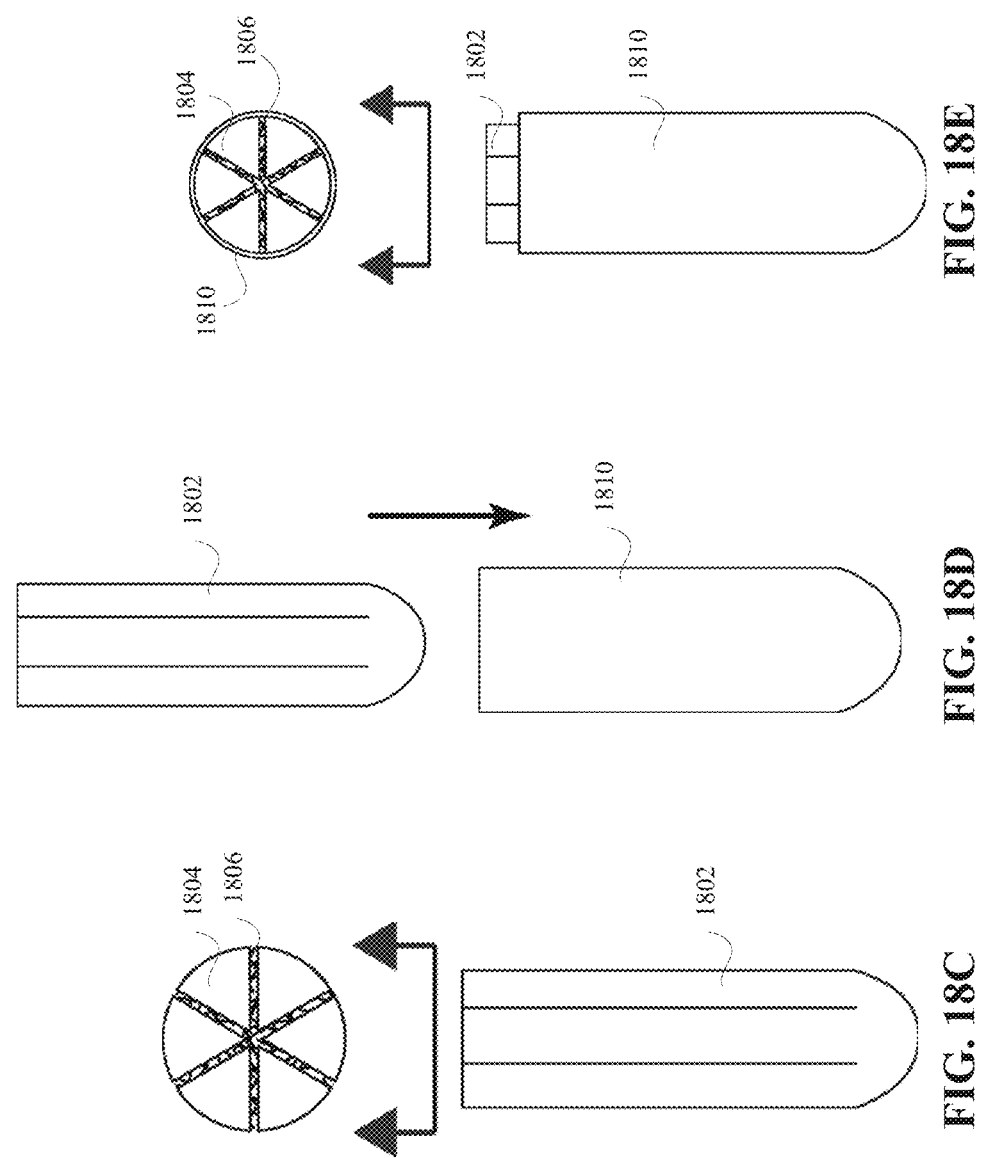

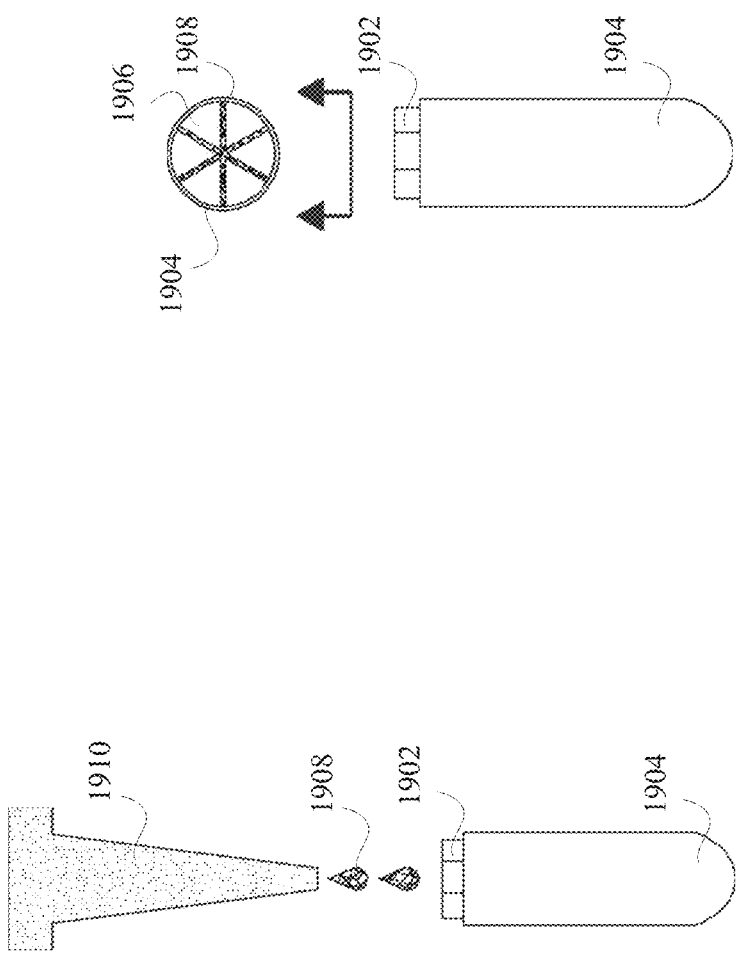

ENCAPSULATION OF GASTRIC RESIDENCE SYSTEMS

CROSS-REFERENCE TO RELATED APPLICATIONS

This application is a divisional application of U.S. patent application Ser. No. 16/648,207, filed internationally on Sep. 19, 2018, which is a national stage application under 35 U.S.C. § 371 of International Application No. PCT/US2018/051816 having an International Filing Date of Sep. 19, 2018, which claims priority benefit of U.S. Provisional Patent Application No. 62/561,043, filed Sep. 20, 2017. The entire contents of those applications are hereby incorporated by reference herein.

FIELD OF THE INVENTION

The invention relates to systems for sustained gastric release of therapeutic agents and methods of encapsulation thereof.

BACKGROUND OF THE INVENTION

Gastric residence systems are delivery systems for therapeutic agents which remain in the stomach for days to weeks, or even over longer periods, during which time drugs or other agents can elute from the systems for absorption in the gastrointestinal tract. Examples of such systems are described in International Patent Application No. PCT/US2015/035423. Gastric residence systems are most conveniently administered to a patient via a capsule in a compacted form. Upon dissolution of the capsule in the stomach, the systems expand to a size which resists passage through the pyloric sphincter over the desired residence period.

The current invention describes advancements in compacting and inserting gastric residence systems into a capsule for storage and administration to a patient.

SUMMARY OF THE INVENTION

Described are systems and methods for compacting and encapsulating a compactable gastric residence system for administration to a patient. The embodiments of the disclosure disclose methods and apparatus for receiving, orienting, sorting, compacting, securing, and packaging gastric residence systems. In particular, mechanical systems that can be used to rapidly and automatically compact and encapsulate commercial quantities of gastric residence systems are described.

Generally, the disclosed apparatus herein can be configured to work sequentially and cooperatively to rapidly and automatically perform some or all the steps of compacting and encapsulating the compactable gastric residence system with little or no manual interaction. In some embodiments, several steps can be performed by a single apparatus. For example, a vibratory bowl feeder can be configured to receive, orient and at least partially sort gastric residence systems. Furthermore, many of the compacting systems can also be configured to immediately package gastric residence systems after placing them into a compacted form. In some embodiments, a pick and place apparatus can be used to receive and orient gastric residence systems. In some embodiments, a vibratory bowl feeder can be used in conjunction with a pick and place system. For example, the vibratory bowl feeder can primarily function to separate entangled gastric residence systems and send them to a conveyor belt where the gastric residence systems can be picked up and oriented for compacting and encapsulation by the pick and place system. In some embodiments, different groupings of steps can be used to achieve the same result of automatically compacting an encapsulating the gastric residence systems. For example, gastric residence systems may be receiving oriented, sorted, and compacted and then placed into a cartridge or magazine for later packaging and/or securing by a packaging system configured to receive the cartridge or magazine.

The physical characteristics of the compactable gastric residence systems inform the design of the various systems and methods used for receiving, orienting, sorting compacting securing and packing the gastric residence systems. Accordingly, detailed information about the qualities and characteristics of embodiments of gastric residence systems are provided as context for the functions of the various systems and methods that are the subject of the application herein. It should be understood that these detailed descriptions of embodiments of gastric residence systems are presented primarily to provide context for the requirements of the embodiments of systems and apparatus. Furthermore, the systems and apparatus described herein can be adapted to other physical configurations of gastric residence systems other than those explicitly described, and physical characteristics the embodiments described in detail are provided as non-limiting examples of the systems and apparatus.

BRIEF DESCRIPTION OF THE DRAWINGS

FIG. 3 shows the embodiment of a gastric residence system of FIG. 2 in a folded configuration. The capsule holding the system in the folded configuration is not shown.

FIGS. 5A-5D show an embodiment of a pick and place system for placing gastric residence systems into position for compacting into a compacted for by a compacting fixture.

FIGS. 6A-6D show an additional embodiment of a pick and place system for placing gastric residence systems into position for compacting into a compacted for by a compacting fixture.

FIGS. 9A-9C show a second exemplary compacting system for compacting gastric residence systems and inserting the gastric residence system into a container.

FIGS. 10A-10D show a third exemplary compacting system according to examples of the disclosure.

FIGS. 18A-18E show an exemplary technique for mechanically securing a gastric residence system using a non-aqueous gel applied to extended portions of the gastric residence system prior to insertion of the gastric residence system in a capsule body.

FIGS. 19A-19D show an exemplary technique for mechanically securing a gastric residence system using a non-aqueous gel applied to extended portions of the gastric residence system after insertion of the gastric residence system in a capsule body.

DETAILED DESCRIPTION OF THE INVENTION

Figure 1:
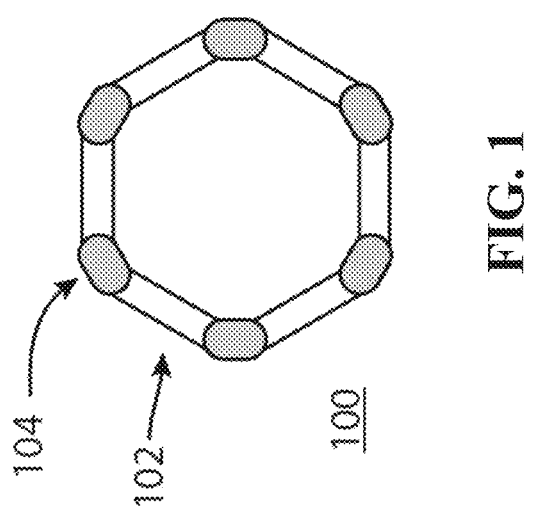
FIG. 1 shows one embodiment of a gastric residence system of the invention.

Described are systems and methods for compacting and encapsulating a compactable gastric residence system for storage and administration to a patient. The compactable gastric residence systems are configured to unfold and spread out when released from the capsule. The geometry, the need for compaction, and elasticity of compactable residence systems can make encapsulating the gastric residence systems particularly difficult. Manual methods of compacting and encapsulating compactible gastric residence systems are slow and inefficient. The described systems and methods allow for the efficient compaction and encapsulation of compactable gastric residence systems. In some embodiments, the systems and methods can be part of an automated encapsulation system. In some embodiments, the systems and methods can be used to modify prior encapsulation technologies to allow for the handling and encapsulation of compactable gastric residence systems.

Encapsulation of gastric residence systems including a linking member linking one or more segments can be performed by a method comprising:
  A. Receiving the compactable gastric residence system in an uncompacted form. In some embodiments, the compactable gastric residence system can be received at a vibratory bowl feeder or a pick and place conveyor.
  B. Orienting the compactable gastric residence system into a compacting position.
  C. Compacting the compactable gastric residence system into a compacted form; and
  D. Inserting the compactable gastric residence system in the compacted form into an opening of a container. In some embodiments, the compactable gastric residence system can be secured in the compacted form by a retaining element such as a band or a cap prior to insertion into the container to prevent expansion of the compactible gastric system in the case of early deployment.

In some embodiments, receiving and orienting compactible gastric residence systems can be performed by a vibratory bowl feeder. A bulk quantity of compactible residence systems can be inserted into the large bowl of a vibratory bowl feeder, for example by pouring the gastric residence systems into the bowl. When received in the bowl, the compactable gastric residence systems can be disorganized and entangled together. By applying a vibration to the bulk of gastric residence systems, individual gastric residence systems can be liberated from the bulk and approach outer walls of the vibratory bowl feeder. The outer walls of the vibratory bowl feeder can include an ascending spiraling track. The shape of the ascending spiraling track can be designed to propel gastric residence systems up the track while simultaneously orienting the gastric residence systems into a preferred orientation for further processing. The output of gastric residence systems that are oriented or partially oriented by the vibratory bowl feeder can be conveyed to further processing steps. In some embodiments, the output of vibratory bowl feeder can be placed onto a flat surface. In some embodiments, the flat surface can also be a moving surface such a conveyor belt for moving the gastric residence systems to a new location. In some embodiments, this output of the vibratory bowl feeder may be considered only partially oriented. For example, the vibratory bowl feeder may provide gastric residence systems flat and centered on a conveyor belt, but some embodiments of a compacting system may further require a particular rotational orientation to compact the gastric residence systems.

In some embodiments, a pick and place system can be used for further orienting and positioning gastric residence systems. The pick and place system can be configured to engage with a gripping portion of a gastric residence system. A tool tip of the pick and place system can be configured to engage with the gripping portion of the gastric residences system. In some embodiments, a gripping handle may be included on the gripping portion, and the pick and place system may be configured to lift the gastric residence system by the gripping handle. In some embodiments, a surface shape of the gripping portion of the gastric residence system may be matched to the shape of a vacuum cup such that sufficient suction can be applied to the gripping portion to allow the pick and place system to lift the gastric residence system and place it in a compacting fixture. In some examples, a flexible aperture may be provided in the gripping portion of the gastric residence system. An expanding head configured to insert into the aperture and expand can grip the flexible aperture by friction and allow the pick and place system to lift the gastric residence system and place it in a compacting fixture. In some embodiments, the pick and place system may include a pneumatic gripping arm that can grab exterior edges of the gripping surface to lift the gastric residence system and place it in a compacting fixture. The pick and place system may include optical sensors for recognizing the presence, position, and orientation of gastric residence systems to properly engage with the gripping portion of the gastric residence system. For example, the pick and place system may be able to recognize the orientation of the opening in the handle and properly position the grabbing tool to engage with the handle regardless of the rotational orientation of the gastric residence system.

In some embodiments, a vibratory bowl feeder and a pick and place tool can be used in conjunction for receiving, sorting, and orienting gastric residence systems. For example, the vibratory bowl feeder may be primarily used for separating entangled gastric residence systems from a bulk and providing separate individual units to the pick and place system, which can then subsequently handle orientation and placement of the gastric residence systems into a compacting fixture.

Multiple different embodiments of compacting systems and fixtures are disclosed in the present disclosure. In general, the illustrated compacting systems are configured to fold the gastric residence systems into a compacted form that can fit within a container such as a capsule. For gastric residence systems having elongate members mutually connected at a single linking member (e.g., as described in FIGS. 2-3 below), force can be applied to each of the elongate members (sometimes referred to as arms) to bring distal ends of the respective arms closer together. In some embodiments, the folding can be accomplished by pressing the gastric residence system by its central linking member through an aperture. In some embodiments, a tapered tube can be used to gradually folder the arms as the tapered tube narrows to an aperture slightly smaller than the opening size of the capsule that will ultimately acts as a container for the gastric residence system. In some embodiments, a mechanically variable aperture can gradually apply pressure to the arms of the gastric residence system while a force is applied to the linking member by a piston. In some examples, force can be applied in two stages as the piston can prevent the arms of the gastric residence system from completely folding when force is applied to the middle at the linking member of the gastric residence system. In some examples, once the arms can no longer fold from force applied to the linking member, a second larger piston can be used to apply force to the distal ends of the gastric residence system to complete the folding and compacting process. In some embodiments, groups of arms can be grouped in proximity in two groups and then a hinging mechanism can be used to bring the two groups close together to achieve the final compacted form. In some embodiments, rotatable hinges can individually engage with each arm of the gastric residence system and simultaneously bring the arms close together into a compacted form. In some embodiments, a flexible runner system interconnecting arms of the gastric residence system can be gripped and used to apply a compacting force to the arms of the gastric residence system.

In general, it is preferable to immediately insert the compacted gastric residence systems into a container after they are placed in the compacted form. In some embodiments, a piston can be used to press the compacted gastric residence systems into a capsule while the compacting force is still being applied to prevent the gastric residence system from opening into the uncompacted form. In some embodiments, compacted or partially compacted gastric residence systems can be loaded into a magazine or cartridge. In some embodiments, the contents of the cartridge can be rapidly loaded into capsules by applying force to a stack of the compacted residence systems and sequentially ejecting the compacted residence systems into capsules without needing to pause for a compacting step between successive encapsulations.

In some embodiments, prior to encapsulation, the gastric residence system can be secured in the compacted form by a band or cap that secures the arms of the gastric residence system together. In some embodiments, a retaining band can be slipped over the distal ends of the arms of the gastric residence system and secure the arms of the gastric residence system around a circumference of the compacted form. In some embodiments a retaining cap can engage directly with the distal ends of the arms to secure the gastric residence system in the compacted form. The retaining band or retaining cap can be can be made of materials well-known in the art, such as gelatin or hydroxypropyl methylcellulose. In some embodiments, the retaining band or cap can be made of a material that dissolves in the gastric environment, but not in the oral or esophageal environment, which prevents premature release of the system prior to reaching the stomach. Furthermore, that cap or band can create a gap between the gastric residence system and the inner walls of a capsule during the insertion process, which can reduce friction on coatings on the outer surface of the compacted gastric residence system.

In some embodiments, the compactible gastric residence systems can have coatings that can include therapeutic agents or coatings that can be used to control the deployment of the gastric residence system or the rate of release of the therapeutic agents contained within the gastric residence system. Accordingly, steps can be taken in the various steps of the encapsulation process. For example, surfaces that come in contact with the gastric residence system can be coated with low friction agents such as biocompatible fluoropolymers to minimize friction. Furthermore, the systems and apparatus can be designed to physically contact the gastric residence systems in positions specifically designed for the encapsulation process that may optionally omit the coatings. Furthermore, surfaces of the receiving, orienting, sorting, compacting, securing, and packaging systems can be constructed from smoothly milled and/or highly polished materials (e.g., highly polished stainless steel) free of burrs and sharp edges to avoid damaging the gastric residence systems and their coatings.

Before further discussing the encapsulation systems and methods of the disclosure in connection to the FIGURES, particularly FIGS. 4-14 of the disclosure, additional information regarding the structure, function, and purpose of gastric residence systems are disclosed below. The encapsulation systems herein are designed to accommodate physical characteristics of compactable gastric residence systems. Furthermore, care must to taken such that the encapsulation process does not interfere with the proper function of the gastric residence systems and their delivery of therapeutic agents to patients. Accordingly, operational and physical details of several embodiments of gastric residence systems are disclosed below. It should be understood that the explicitly disclosed embodiments are not limiting, and that the encapsulation methods and systems described herein can be adapted to encapsulation of other physical forms of gastric residence systems.

General Principles of Gastric Residence Systems

Gastric residence systems can be designed to be administered to the stomach of a patient, either by swallowing or other method of administration (for example, feeding tube or gastric tube). Once a gastric residence system is in place in the stomach, the system can remain in the stomach for the desired residence time (such as three days, seven days, two weeks, etc.), which thus entails resistance to passage through the pyloric valve separating the stomach and the small intestine. It releases therapeutic agent over the period of residence, with minimal burst release. While resident in the stomach, the system does not interfere with the normal passage of food or other gastric contents. The system passes out of the stomach at the end of the desired residence time, and is readily eliminated from the patient. If the system prematurely passes from the stomach into the small intestine, it does not cause intestinal obstruction, and again is readily eliminated from the patient.

Administration

The gastric residence system is contained in a capsule or other container which can be swallowed by the patient, or which is otherwise able to be administered to the stomach for patients unable to swallow (e.g., via gastrostomy tube, feeding tube, gastric tube, or other route of administration to the stomach). Accordingly, the gastric residence system is capable of being compacted or compressed into a form small enough to be swallowed or otherwise administered, and is preferably placed inside a container such as a capsule. Thus, the system is configured to have a compacted form in a container (by folding, compression, or other method of reducing the size of the system). Examples of the disclosure related to encapsulating these gastric residence systems will be discussed in further detail below in connection with the various embodiments of the disclosure.

Figure 2:
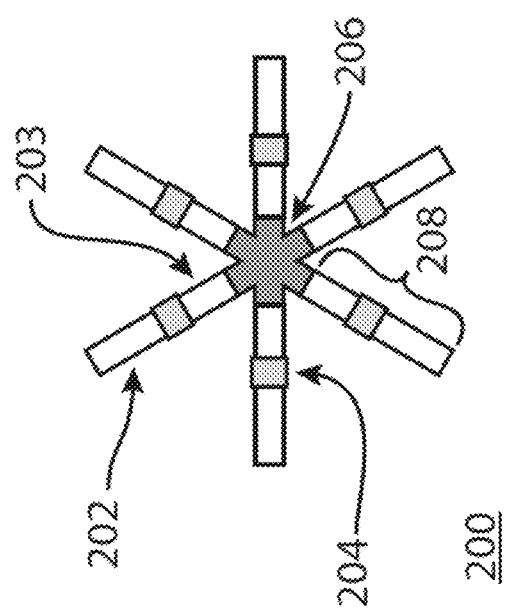
FIG. 2 shows another embodiment of a gastric residence system of the invention.
Figure 2A:
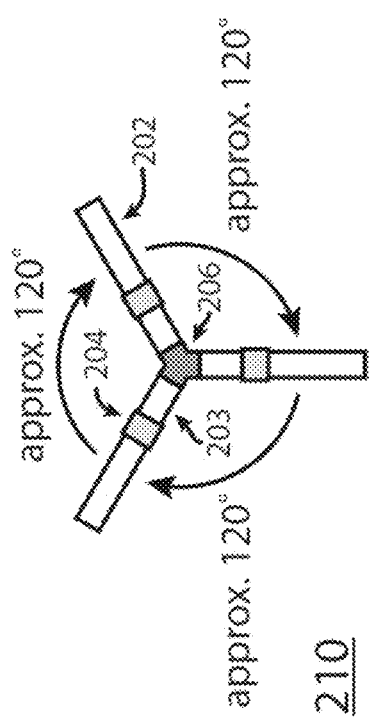
FIG. 2A shows another embodiment of a gastric residence system of the invention.

Such compressible or compactable systems are shown in FIG. 1, FIG. 2, and FIG. 2A. The ring-shaped design for a gastric residence system shown in FIG. 1 can be twisted into a double helix, which compresses the structure to a roughly cylindrical shape which can be placed in a capsule. The star-shaped (stellate) design for a gastric residence system shown in FIG. 2 and FIG. 2A can be folded at its central portion, which can then be placed into a capsule. The system is administered to a patient by swallowing the capsule or by gastric tube.

Deployment of the System in the Stomach

Once the capsule or other container arrives in the stomach of the patient, the capsule dissolves and releases the compacted gastric residence system. Upon release, the system returns to its original shape, such as a ring shape or a star shape. The dimensions of the uncompressed/uncompacted system are suitable to prevent passage of the system through the pyloric sphincter for the period of time during which the system is to reside in the stomach. In some embodiments, the compacted gastric residence system can further be secured by a dissolvable retaining band or cap that can prevent inadvertent premature deployment of the gastric residence system in case of a failure of the capsule, for example.

While in the stomach, the gastric residence system is compatible with digestion and other normal functioning of the stomach or gastrointestinal tract. The gastric residence system does not interfere with or impede the passage of chyme (partially digested food) or other gastric contents which exit the stomach through the pyloric sphincter into the duodenum.

Elution of Therapeutic Agent from the System while Resident in the Stomach

The gastric residence system comprises a plurality of carrier polymer-agent components. The carrier polymer-agent components comprise a carrier polymer, a dispersant, and a therapeutic agent (or a salt thereof). The plurality of carrier polymer-agent components are linked together by one or more coupling polymer components. Agent is eluted from the carrier polymer-agent components into the gastric fluid of the patient over the desired residence time of the system. Release of the therapeutic agent is controlled by appropriate formulation of the carrier polymer-agent components, including by the use of the dispersant in formulation of the carrier polymer-agent components, and by milling of the therapeutic agent to particles of desired size prior to blending the agent with the carrier polymer and dispersant. In additional, coatings can be applied to outer surfaces of the gastric residence system. The coatings can include additional therapeutic agents or agents that can affect the release of therapeutic agents or the residence duration of the gastric residence system. As discussed above and below in the disclosure, care must be taken during the encapsulation of the gastric residence systems to avoid damage that may change the elution of therapeutic agents by the gastric residence system.

Passage of the System from the Stomach

The gastric residence system passes out of in the stomach at an appropriate time point, that is, once the useful therapeutic agent delivery lifetime of the system has been reached, or at a reasonable fraction of the useful therapeutic agent delivery lifetime of the system. This is accomplished by suitable choice of the coupling polymer components and the dimensions of the system. In its intact, uncompressed form, the gastric residence system is designed to resist passage through the pyloric sphincter. The coupling polymer components are chosen such that they gradually degrade over the residence period in the stomach. When the coupling polymer components are sufficiently weakened by degradation, the gastric residence system breaks apart into smaller pieces, which are able to pass through the pyloric sphincter. The system then passes through the intestines and is eliminated from the patient.

Safety Elements

In its desired mode of operation, the gastric residence systems have their intact uncompressed form while resident in the stomach, and do not pass through the pylorus until they break apart after the desired residence time. If a gastric residence system passes intact into the intestine, it has the potential to result in intestinal blockage. Thus, the gastric residence systems are designed to uncouple rapidly in the intestinal environment by dissolution of the coupling polymer, within 48 hours, preferably within 24 hours, more preferably within 12 hours, yet more preferably within 1-2 hours, so as to avoid potential intestinal blockage. This is readily accomplished by using enteric polymers as the coupling polymers. Enteric polymers are relatively resistant to the acidic pH levels encountered in the stomach, but dissolve rapidly at the higher pH levels found in the duodenum. Use of enteric coupling polymers as safety elements protects against undesired passage of the intact gastric residence system into the small intestine. The use of enteric coupling polymers also provides a manner of removing the gastric residence system prior to its designed residence time; should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric coupling polymers. The gastric residence system will then break apart and be eliminated from the patient.

Definitions

A "carrier polymer" is a polymer suitable for blending with a therapeutic agent, such as a drug, for use in the invention.

A "hydrophilic therapeutic agent," "hydrophilic agent," or "hydrophilic drug" is an agent which readily dissolves in water. A hydrophilic agent is defined as an agent which has a solubility in water of 1 mg/ml or greater. Alternatively, a hydrophilic agent can be defined as an agent which has a log P (log partition coefficient P, where P=(concentration in 1-octanol)/(concentration in $H_2O$)) in a 1-octanol/water system of less than 0.5. The pH at which solubility or log P is measured is 1.6, approximating the gastric environment.

A "hydrophobic therapeutic agent," "hydrophobic agent," or "hydrophobic drug" is an agent which does not readily dissolve in water. A hydrophobic agent is defined as an agent which has a solubility in water of less than 1 mg/ml. Alternatively, a hydrophobic agent can be defined as an agent which has a log P (log partition coefficient) in a 1-octanol/water system of greater than 1. Alternatively, a hydrophobic therapeutic agent can be defined as an agent which has a higher solubility in ethanol than in water. Alternatively, a hydrophobic therapeutic agent can be defined as an agent which has a higher solubility in 40% ethanol/60% simulated gastric fluid than in 100% simulated gastric fluid.

A "dispersant" is defined as a substance which aids in the minimization of therapeutic agent particle size and the dispersal of therapeutic agent particles in the carrier polymer matrix. That is, the dispersant helps minimize or prevent aggregation or flocculation of particles during fabrication of the systems. Thus, the dispersant has anti-aggregant activity and anti-flocculant activity, and helps maintain an even distribution of therapeutic agent particles in the carrier polymer matrix.

An "excipient" is any substance added to a formulation of therapeutic agent that is not the therapeutic agent itself. Excipients include, but are not limited to, binders, coatings, diluents, disintegrants, emulsifiers, flavorings, glidants, lubricants, and preservatives. The specific category of dispersant falls within the more general category of excipient.

An "elastic polymer" or "elastomer" (also referred to as a "tensile polymer") is a polymer that is capable of being deformed by an applied force from its original shape for a period of time, and which then substantially returns to its original shape once the applied force is removed.

A "coupling polymer" is a polymer suitable for coupling any other polymers together, such as coupling a first carrier polymer-agent component to a second carrier polymer-agent component.

"Substantially constant plasma level" refers to a plasma level that remains within plus-or-minus 25% of the average plasma level measured over the period that the gastric residence system is resident in the stomach.

"Biocompatible," when used to describe a material or system, indicates that the material or system does not provoke an adverse reaction, or causes only minimal, tolerable adverse reactions, when in contact with an organism, such as a human. In the context of the gastric residence systems, biocompatibility is assessed in the environment of the gastrointestinal tract.

As used herein, the singular forms "a", "an", and "the" include plural references unless indicated otherwise or the context clearly dictates otherwise.

A "patient," "individual," or "subject" refers to a mammal, preferably a human or a domestic animal such as a dog or cat. In a preferred embodiment, a patient, individual, or subject is a human.

The "diameter" of a particle as used herein refers to the longest dimension of a particle.

"Treating" a disease or disorder with the systems and methods disclosed herein is defined as administering one or more of the systems disclosed herein to a patient in need thereof, with or without additional therapeutic agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the systems and methods disclosed herein is defined as administering one or more of the systems disclosed herein to a patient in need thereof, with or without additional therapeutic agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The systems and methods of the invention can then be used to treat asymptomatic patients at risk of developing the clinical symptoms of the disease or disorder, in order to suppress the appearance of any adverse symptoms.

"Therapeutic use" of the systems disclosed herein is defined as using one or more of the systems disclosed herein to treat a disease or disorder, as defined above. A "therapeutically effective amount" of a therapeutic agent is an amount of the therapeutic agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the systems disclosed herein is defined as using one or more of the systems disclosed herein to suppress a disease or disorder, as defined above. A "prophylactically effective amount" of a therapeutic agent is an amount of the therapeutic agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition or system is described as "consisting essentially of" the listed elements, the composition or system contains the elements expressly listed, and may contain other elements which do not materially affect the condition being treated (for compositions for treating conditions), or the properties of the described system (for compositions comprising a system). However, the composition or system either does not contain any other elements which do materially affect the condition being treated other than those elements expressly listed (for compositions for treating systems) or does not contain any other elements which do materially affect the properties of the system (for compositions comprising a system); or, if the composition or system does contain extra elements other than those listed which may materially affect the condition being treated or the properties of the system, the composition or system does not contain a sufficient concentration or amount of those extra elements to materially affect the condition being treated or the properties of the system. When a method is described as "consisting essentially of" the listed steps, the method contains the steps listed, and may contain other steps that do not materially affect the condition being treated by the method or the properties of the system produced by the method, but the method does not contain any other steps which materially affect the condition being treated or the system produced other than those steps expressly listed.

This disclosure provides several embodiments. It is contemplated that any features from any embodiment can be combined with any features from any other embodiment where possible. In this fashion, hybrid configurations of the disclosed features are within the scope of the present invention.

System Geometry

A variety of geometrical configurations can be used for the gastric residence systems. One such configuration is shown in FIG. 1, which adopts the shape of a ring in its uncompacted form. Gastric residence system 100 is constructed from carrier polymer-agent components 102 and couplings 104 comprising coupling polymer. The system can be folded at the coupling polymer joints, or twisted into a helix for packaging into a capsule in its compacted form. Once the capsule dissolves in the stomach, system 100 unfolds to the circular shape of its uncompacted form, preventing passage through the pyloric sphincter. In this embodiment, the coupling polymer serves also as an elastomer. The carrier polymer-agent components 102 and couplings 104 are not necessarily drawn to scale; the dimensions (such as length or diameter) of the "arms" 102 and couplings 104 can vary from those shown in the FIGURE.

Another configuration which is star-shaped (stellate) is shown in FIG. 2. Gastric residence system 200 is constructed around a central elastomer 206 which has elongate members, or "arms," projecting radially; one such arm is labeled as 208 in the FIGURE. The arms are formed by outer carrier polymer-agent components 202, inner carrier polymer-agent components 203, and couplings 204 comprising coupling polymer. Components 202, 204, and 203 together comprise an "arm" of this "star-shaped" configuration. Elastomer 206 enables the system to be folded for packaging into a capsule. Again, the components are not necessarily drawn to scale.

FIG. 2A shows another embodiment of the system, with three arms. For the star-shaped configurations of FIG. 2 or FIG. 2A, it will be appreciated that the arms can be spaced substantially evenly around the circumference of the connecting elastomer 206. Thus, for a star-shaped device having N arms, the arms will be spaced apart by (360/N) degrees. For example, the three arms in the device of FIG. 2A are spaced apart by about 120 degrees. As for FIG. 1 and FIG. 2, the components are not necessarily drawn to scale.

FIG. 3 shows the folded state of the system of FIG. 2 or of FIG. 2A, as it would be folded for packaging into a capsule (not shown in the FIGURE), with arms 308 comprising outer carrier polymer-agent components 302, inner carrier polymer-agent components 303, couplings 304 comprising coupling polymer, and elastomer 306, where the elastomer has been deformed from its configuration in FIG. 2 or FIG. 2A. For the sake of clarity, only two "arms" formed by outer carrier polymer-agent components 302, couplings 304, and inner carrier polymer-agent components 303 are shown in FIG. 3; additional arms may be present such as shown in the systems in FIG. 2 and FIG. 2A. Upon dissolution of the retaining capsule in the stomach, system 300 unfolds to the star-shaped configuration depicted in FIG. 2 or FIG. 2A, preventing passage through the pyloric sphincter over the residence time of the system. The carrier polymer-agent components, couplings, and elastomer are not necessarily drawn to scale; the dimensions (such as length or diameter) of the carrier polymer-agent components, couplings, and elastomer can vary from those shown in the FIGURE.

As will be discussed in further detail below, the encapsulation systems can be designed to accommodate the varying system geometries that can be used to provide compactable gastric residence systems including the various geometries described above as well as additional embodiments described below as well as geometries suitable for compactable gastric residence systems that are not explicitly described herein.

System Dimensions

The system must be able to adopt a compacted state with dimensions that enable the patient to swallow the system (or for the system to be introduced into the stomach by alternate means, such as a feeding tube or gastrostomy tube). Typically, the system is held in the compacted state by a container such as a capsule. In some embodiments, the system may further be held in the compacted state by a dissolvable retaining band or retaining cap. Upon entry into the stomach, the system is then released from the container and adopts an uncompacted state, that is, an expanded conformation, with dimensions that prevent passage of the system through the pyloric sphincter, thus permitting retention of the system in the stomach.

Accordingly, the system should be capable of being placed inside a standard-sized capsule of the type commonly used in pharmacy. Standard capsule sizes in use in the United States are provided below in Table 1 (see "Draft Guidance for Industry on Size, Shape, and Other Physical Attributes of Generic Tablets and Capsules" at URL https://www.regulations.gov/document?D=FDA-2013-N-1434-0002). As these are the outer dimensions of the capsule, and as dimensions will vary slightly between capsule manufacturers, the system should be capable of adopting a configuration which is about 0.5 to 1 mm smaller than the outer diameter shown, and about 1 to 2 mm shorter than the length shown in Table 1.

TABLE 1

| Capsule Size | Outer Diameter (mm) | Length (mm) |
| --- | --- | --- |
| 000 | 9.9 | 26.1 |
| 00 | 8.5 | 23.3 |
| 0 | 7.6 | 21.7 |
| 1 | 6.9 | 19.4 |
| 2 | 6.3 | 18.0 |
| 3 | 5.8 | 15.9 |
| 4 | 5.3 | 14.3 |
| 5 | 4.9 | 11.1 |

Capsules can be made of materials well-known in the art, such as gelatin or hydroxypropyl methylcellulose. In one embodiment, the capsule is made of a material that dissolves in the gastric environment, but not in the oral or esophageal environment, which prevents premature release of the system prior to reaching the stomach.

In one embodiment, the system will be folded or compressed into a compacted state in order to fit into the capsule, for example, in a manner such as that shown in FIG. 3. Once the capsule dissolves in the stomach, the system will adopt a configuration suitable for gastric retention, for example, in a manner such as that shown in FIG. 2 or FIG. 2A. Preferred capsule sizes are 00 and 00el (a 00el-size capsule has the approximate length of a 000 capsule and the approximate width of a 00 capsule), which then places constraints on the length and diameter of the folded system.

Once released from the container, the system adopts an uncompacted state with dimensions suitable to prevent passage of the gastric residence system through the pyloric sphincter. In one embodiment, the system has at least two perpendicular dimensions, each of at least 2 cm in length; that is, the gastric residence system measures at least about 2 cm in length over at least two perpendicular directions. In another embodiment, the perimeter of the system in its uncompacted state, when projected onto a plane, has two perpendicular dimensions, each of at least 2 cm in length. The two perpendicular dimensions can independently have lengths of from about 2 cm to about 7 cm, about 2 cm to about 6 cm, about 2 cm to about 5 cm, about 2 cm to about 4 cm, about 2 cm to about 3 cm, about 3 cm to about 7 cm, about 3 cm to about 6 cm, about 3 cm to about 5 cm, about 3 cm to about 4 cm, about 4 cm to about 7 cm, about 4 cm to about 6 cm, about 4 cm to about 5 cm, or about 4 cm to about 4 cm. These dimensions prevent passage of the gastric residence system through the pyloric sphincter.

It should be understood that references to capsules used for encapsulation in the descriptions below can include any of the above described capsule dimensions and ranges.

Figure 2B:
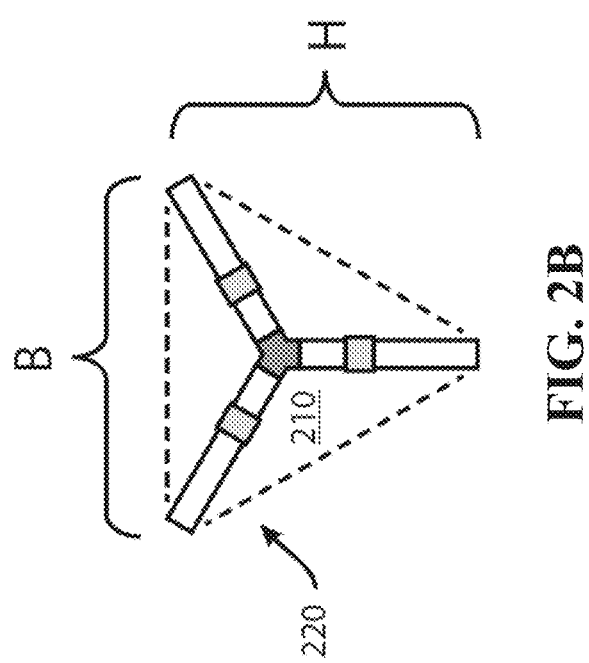
FIG. 2B shows certain dimensions of the gastric residence system of FIG. 2B.

For star-shaped polymers with N arms (where N is greater than or equal to three), the arms can have dimensions such that the system has at least two perpendicular dimensions, each of length as noted above. For example, the system of FIG. 2A can be circumscribed by a triangle, as shown in FIG. 2B, where the triangle is described by the length of its base B and height H, where B and H are perpendicular, and which comprise the two perpendicular dimensions of length as noted above. These two perpendicular dimensions are chosen as noted above in order to promote retention of the gastric residence system.

The system is designed to eventually break apart in the stomach at the end of the desired residence time. Once the coupling polymers break, the remaining components of the system are of dimensions that permit passage of the system through the pyloric sphincter, small intestine, and large intestine. Finally, the system is eliminated from the body by defecation, or by eventual complete dissolution of the system in the small and large intestines.

System Polymeric Composition

The choice of the individual polymers for the carrier polymer, coupling polymer, and elastomer influence many properties of the system, such as therapeutic agent elution rate (dependent on the carrier polymer, as well as other factors), the residence time of the system (dependent on the degradation of any of the polymers, principally the coupling polymers), the uncoupling time of the system if it passes into the intestine (dependent primarily on the enteric degradation rate of the coupling polymer, as discussed herein), and the shelf life of the system in its compressed form (dependent primarily on properties of the elastomer). As the systems will be administered to the gastrointestinal tract, all of the system components should be biocompatible with the gastrointestinal environment.

The rate of elution of therapeutic agent from the carrier polymer-agent component is affected by numerous factors, including the composition and properties of the carrier polymer, which may itself be a mixture of several polymeric and non-polymeric components; the properties of the therapeutic agent such as hydrophilicity/hydrophobicity, charge state, pKa, and hydrogen bonding capacity; and the properties of the gastric environment. In the aqueous environment of the stomach, avoiding burst release of a therapeutic agent (where burst release refers to a high initial delivery of active pharmaceutical ingredient upon initial deployment of the system in the stomach), particularly a hydrophilic agent, and maintaining sustained release of the agent over a period of time of days to weeks is challenging. In some embodiments, coatings may also be applied to an external surface of the gastric residence system to aid in avoiding burst release of a therapeutic agent. Accordingly, the encapsulation systems and methods below can be adapted to minimize damage (e.g., by friction) to the gastric residence system and its coatings.

The residence time of the systems in the stomach is adjusted by the choice of coupling polymers. The systems will eventually break down in the stomach, despite the use of enteric coupling polymers, as the mechanical action of the stomach and fluctuating pH will eventually weaken the enteric coupling polymers. Coupling polymers which degrade in a time-dependent manner in the stomach can also be used to adjust the time until the system breaks apart, and hence adjust the residence time. Once the system breaks apart, it passes into the intestines and is then eliminated.

The elastomer used in the systems is central to the shelf life of the systems. When the systems are compressed, the elastomer is subjected to mechanical stress. The stress in turn can cause polymer creep, which, if extensive enough, can prevent the systems from returning to their uncompacted configurations when released from the capsules or other container; this in turn would lead to premature passage of the system from the stomach. Polymer creep can also be temperature dependent, and therefore the expected storage conditions of the systems also need to be considered when choosing the elastomer and other polymer components.

The system components and polymers should not swell, or should have minimal swelling, in the gastric environment. The components should swell no more than about 20%, no more than about 10%, or preferably no more than about 5% when in the gastric environment over the period of residence.

Carrier Polymers for Carrier Polymer-Agent Component

The carrier polymer-agent component contains the therapeutic agent to be eluted from the gastric residence system in the gastric environment. Therapeutic agent is blended into the carrier polymer to form a carrier polymer-agent mixture. This mixture can be formed into the desired shape or shapes for use as carrier polymer-agent components in the systems, such as rods for the systems depicted in FIG. 1, FIG. 2, and FIG. 3. Exemplary carrier polymers suitable for use in this invention include, but are not limited to, hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly(vinyl pyrrolidone), ethylene/vinyl alcohol copolymer, poly(vinyl alcohol), carboxyvinyl polymer (Carbomer), Carbopol® acidic carboxy polymer, polycarbophil, poly(ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arabinogalactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), poly(methacrylic acid), polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly(ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. Polycaprolactone (PCL) is a preferred carrier polymer.

Other excipients can be added to the carrier polymers to modulate the release of therapeutic agent. Such excipients can be added in amounts from about 1% to 15%, preferably from about 5% to 10%, more preferably about 5% or about 10%. Examples of such excipients include Poloxamer 407 (available as Kolliphor P407, Sigma Cat #62035); Pluronic P407; Eudragit EPO (available from Evonik); hypromellose (available from Sigma, Cat #H3785), Kolliphor RH40 (available from Sigma, Cat #07076), polyvinyl caprolactam, polyvinyl acetate, polyethylene glycol, and Soluplus (available from BASF; a copolymer of polyvinyl caprolactam, polyvinyl acetate, and polyethylene glycol)

Methods of Manufacture of Carrier Polymer-Agent Components

Blending temperatures for incorporation of the therapeutic agent into polymeric matrices typically range from about 80° C. to about 120° C., although higher or lower temperatures can be used for polymers which are best blended at temperatures outside that range. When using free crystals of therapeutic agent, blending temperatures are preferably from about 80° C. to about 100° C., so as not to melt the agent particles or crystals.

Hot melt extrusion can be used to prepare the carrier polymer-agent components. Single-screw or, preferably, twin-screw systems can be used. As noted, carrier polymers should be used which can be melted at temperatures which do not melt the agent particles blended into the polymer, since melting the particles of therapeutic agent would dramatically change the size distribution characteristics of the particles.

Melting and casting can also be used to prepare the carrier polymer-agent components. The carrier polymer and therapeutic agent, and any other desired components, are mixed together. The carrier polymer is melted (again, at temperatures which do not melt the particles of therapeutic agent), and the melt is mixed so that the agent particles are evenly distributed in the melt, poured into a mold, and allowed to cool.

Solvent casting can also be used to prepare the carrier polymer-agent components. The polymer is dissolved in a solvent, and particles of therapeutic agent are added. A solvent should be used which does not dissolve the agent particles, so as to avoid altering the size characteristics of the particles. The solvent-carrier polymer-agent particle mixture is then mixed to evenly distribute the particles, poured into a mold, and the solvent is evaporated.

Coupling Polymers

The coupling polymer is used to link one or more carrier polymer-agent components to one or more carrier polymer-agent components, to link one or more carrier polymer-agent components to one or more elastomer components, or to link one or more elastomer components to one or more elastomer components. Enteric polymers are preferred for use as coupling polymers. Enteric polymers are relatively insoluble under acidic conditions, such as the conditions encountered in the stomach, but are soluble under the less acidic to basic conditions encountered in the small intestine. Enteric polymers which dissolve at about pH 5 or above can be used as coupling polymers, as the pH of the initial portion of the small intestine, the duodenum, ranges from about 5.4 to 6.1. If the gastric residence system passes intact through the pyloric valve, the enteric coupling polymer will dissolve and the components linked by the coupling polymer will break apart, allowing passage of the residence system through the small and large intestines. If, during treatment, the gastric residence system must be removed quickly for any reason, the patient can drink a mildly basic aqueous solution (such as a bicarbonate solution) in order to induce immediate de-coupling of the gastric residence system.

Exemplary coupling polymers include, but are not limited to, cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic monoester copolymer, methacrylic acid methylmethacrylate copolymer, methyl acrylate-methacrylic acid copolymer, methacrylate-methacrylic acid-octyl acrylate copolymer, and copolymers, mixtures, blends and combinations thereof. Some of the enteric polymers that can be used in the invention are listed in Table 2, along with their dissolution pH. (See Mukherji, Gour and Clive G. Wilson, "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences Volume 126, New York: Marcel Dekker, 2002.) Preferably, enteric polymers that dissolve at a pH of no greater than about 5 or about 5.5 are used. Poly(methacrylic acid-co-ethyl acrylate) (sold under the trade name EUDRAGIT L 100-55; EUDRAGIT is a registered trademark of Evonik Rohm GmbH, Darmstadt, Germany) is a preferred enteric polymer. Cellulose acetate phthalate, cellulose acetate succinate, and hydroxypropyl methylcellulose phthalate are also suitable enteric polymers.

In one embodiment, the enteric polymers used in the gastric residence system dissolve at a pH above about 4. In another embodiment, the enteric polymers used in the gastric residence system dissolve at a pH above about 5. In another embodiment, the enteric polymers used in the gastric residence system dissolve at a pH above about 6. In another embodiment, the enteric polymers used in the gastric residence system dissolve at a pH above about 7. In another embodiment, the enteric polymers used in the gastric residence system dissolve at a pH above about 7.5. In another embodiment, the enteric polymers used in the gastric residence system dissolve at a pH between about 4 and about 5. In another embodiment, the enteric polymers used in the gastric residence system dissolve at a pH between about 4 and about 6. In another embodiment, the enteric polymers used in the gastric residence system dissolve at a pH between about 4 and about 7. In another embodiment, the enteric polymers used in the gastric residence system dissolve at a pH between about 4 and about 7.5. In another embodiment, the enteric polymers used in the gastric residence system dissolve at a pH between about 5 and about 6. In another embodiment, the enteric polymers used in the gastric residence system dissolve at a pH between about 5 and about 7. In another embodiment, the enteric polymers used in the gastric residence system dissolve at a pH between about 5 and about 7.5. In another embodiment, the enteric polymers used in the gastric residence system dissolve at a pH between about 6 and about 7. In another embodiment, the enteric polymers used in the gastric residence system dissolve at a pH between about 6 and about 7.5.

TABLE 2

| Polymer | Dissolution pH |
| --- | --- |
| Cellulose acetate phthalate | 6.0-6.4 |
| Hydroxypropyl methylcellulose phthalate 50 | 4.8 |
| Hydroxypropyl methylcellulose phthalate 55 | 5.2 |

TABLE 2-continued

| Polymer | Dissolution pH |
| --- | --- |
| Polyvinylacetate phthalate | 5.0 |
| Methacrylic acid-methyl methacrylate copolymer (1:1) | 6.0 |
| Methacrylic acid-methyl methacrylate copolymer (2:1) | 6.5-7.5 |
| Methacrylic acid-ethyl acrylate copolymer (2:1) | 5.5 |
| Shellac | 7.0 |
| Hydroxypropyl methylcellulose acetate succinate | 7.0 |
| Poly (methyl vinyl ether/maleic acid) monoethyl ester | 4.5-5.0 |
| Poly (methyl vinyl ether/maleic acid) n-butyl ester | 5.4 |

Additional preferred polymers for use as coupling polymers are polymers that degrade in a time-dependent manner in the gastric environment. Triacetin degrades in a time-dependent manner over seven days in simulated gastric fluid, while Plastoid B retains its strength over a seven-day period in simulated gastric fluid. Thus, a polymer that degrades in a time-dependent manner can be readily prepared by mixing Plastoid B and triacetin; the degradation time of the Plastoid B-triacetin mixture can be extended by increasing the amount of Plastoid B used in the mixture, while the degradation time can be decreased by decreasing the amount of Plastoid B used in the mixture.

In some embodiments, the carrier polymer-agent components are elongate members (also referred to as "arms" in some embodiments herein) comprised of segments attached by enteric polymers. In some embodiments, the carrier polymer-agent components are attached to the elastomer component of the system by enteric polymers. In any of these embodiments, when enteric polymers are used for both segment-to-segment attachments and for attachment of the elongate members to the elastomeric component, the enteric polymer used for segment-segment attachments can be the same enteric polymer as the enteric polymer used for attachment of the elongate members to the elastomeric component, or the enteric polymer used for segment-segment attachments can be a different enteric polymer than the enteric polymer used for attachment of the elongate members to the elastomeric component. The enteric polymers used for the segment-segment attachments can all be the same enteric polymer, or can all be different enteric polymers, or some enteric polymers in the segment-segment attachments can be the same and some enteric polymers in the segment-segment attachments can be different. That is, the enteric polymer(s) used for each segment-segment attachment and the enteric polymer used for attachment of the elongate members to the elastomeric component can be independently chosen.

Flexible Coupling Polymers

Flexible coupling polymers, i.e., elastomeric coupling polymers or elastomers, are preferred for use as the central polymer in the star-shaped or stellate design of the gastric residence systems. Crosslinked polycaprolactone, such as the elastomer prepared in Example 10B, is a preferred flexible coupling polymer.

Elastomers

Elastomers (also referred to as elastic polymers or tensile polymers) enable the gastric residence system to be compacted, such as by being folded or compressed, into a form suitable for administration to the stomach by swallowing a container or capsule containing the compacted system. Upon dissolution of the capsule in the stomach, the gastric residence system expands into a shape which prevents passage of the system through the pyloric sphincter of the patient for the desired residence time of the system. Thus, the elastomer must be capable of being stored in a compacted configuration in a capsule for a reasonable shelf life, and of expanding to its original shape, or approximately its original shape, upon release from the capsule. In a preferred embodiment, the elastomer is an enteric polymer, such as those listed in Table 2. In another preferred embodiment, the coupling polymer(s) used in the system are also elastomers. FIG. 1 shows an example of a system where the coupling polymers are also elastomers, in that the circular ring is folded at the joints formed by the coupling polymers for packaging into, for example, a capsule.

In one preferred embodiment, both the coupling polymer and elastomer are enteric polymers, which provides for more complete breakage of the system into the carrier polymer-agent pieces if the system enters the intestine, or if the patient drinks a mildly basic solution in order to induce passage of the system.

Examples of elastomers which can be used include urethane-cross-linked polycaprolactones (see Example 10, section B), poly(acryloyl 6-aminocaproic acid) (PA6ACA), poly(methacrylic acid-co-ethyl acrylate) (EUDRAGIT L 100-55), and mixtures of poly(acryloyl 6-aminocaproic acid) (PA6ACA) and poly(methacrylic acid-co-ethyl acrylate) (EUDRAGIT L 100-55) (see Example 11).

Residence Time

The residence time of the gastric residence system is defined as the time between administration of the system to the stomach and exit of the system from the stomach. In one embodiment, the gastric residence system has a residence time of about 24 hours, or up to about 24 hours. In one embodiment, the gastric residence system has a residence time of about 48 hours, or up to about 48 hours. In one embodiment, the gastric residence system has a residence time of about 72 hours, or up to about 72 hours. In one embodiment, the gastric residence system has a residence time of about 96 hours, or up to about 96 hours. In one embodiment, the gastric residence system has a residence time of about 5 days, or up to about 5 days. In one embodiment, the gastric residence system has a residence time of about 6 days, or up to about 6 days. In one embodiment, the gastric residence system has a residence time of about 7 days, or up to about 7 days. In one embodiment, the gastric residence system has a residence time of about 10 days, or up to about 10 days. In one embodiment, the gastric residence system has a residence time of about 14 days, or up to about 14 days. In one embodiment, the gastric residence system has a residence time of about 3 weeks, or up to about 3 weeks. In one embodiment, the gastric residence system has a residence time of about 4 weeks, or up to about 4 weeks. In one embodiment, the gastric residence system has a residence time of about one month, or up to about one month.

In one embodiment, the gastric residence system has a residence time between about 24 hours and about 7 days. In one embodiment, the gastric residence system has a residence time between about 48 hours and about 7 days. In one embodiment, the gastric residence system has a residence time between about 72 hours and about 7 days. In one embodiment, the gastric residence system has a residence time between about 96 hours and about 7 days. In one embodiment, the gastric residence system has a residence time between about 5 days and about 7 days. In one embodiment, the gastric residence system has a residence time between about 6 days and about 7 days.

In one embodiment, the gastric residence system has a residence time between about 24 hours and about 10 days. In one embodiment, the gastric residence system has a residence time between about 48 hours and about 10 days. In one embodiment, the gastric residence system has a residence time between about 72 hours and about 10 days. In one embodiment, the gastric residence system has a residence time between about 96 hours and about 10 days. In one embodiment, the gastric residence system has a residence time between about 5 days and about 10 days. In one embodiment, the gastric residence system has a residence time between about 6 days and about 10 days. In one embodiment, the gastric residence system has a residence time between about 7 days and about 10 days.

In one embodiment, the gastric residence system has a residence time between about 24 hours and about 14 days. In one embodiment, the gastric residence system has a residence time between about 48 hours and about 14 days. In one embodiment, the gastric residence system has a residence time between about 72 hours and about 14 days. In one embodiment, the gastric residence system has a residence time between about 96 hours and about 14 days. In one embodiment, the gastric residence system has a residence time between about 5 days and about 14 days. In one embodiment, the gastric residence system has a residence time between about 6 days and about 14 days. In one embodiment, the gastric residence system has a residence time between about 7 days and about 14 days. In one embodiment, the gastric residence system has a residence time between about 10 days and about 14 days.

In one embodiment, the gastric residence system has a residence time between about 24 hours and about three weeks. In one embodiment, the gastric residence system has a residence time between about 48 hours and about three weeks. In one embodiment, the gastric residence system has a residence time between about 72 hours and about three weeks. In one embodiment, the gastric residence system has a residence time between about 96 hours and about three weeks. In one embodiment, the gastric residence system has a residence time between about 5 days and about three weeks. In one embodiment, the gastric residence system has a residence time between about 6 days and about three weeks. In one embodiment, the gastric residence system has a residence time between about 7 days and about three weeks. In one embodiment, the gastric residence system has a residence time between about 10 days and about three weeks. In one embodiment, the gastric residence system has a residence time between about 14 days and about three weeks.

In one embodiment, the gastric residence system has a residence time between about 24 hours and about four weeks. In one embodiment, the gastric residence system has a residence time between about 48 hours and about four weeks. In one embodiment, the gastric residence system has a residence time between about 72 hours and about four weeks. In one embodiment, the gastric residence system has a residence time between about 96 hours and about four weeks. In one embodiment, the gastric residence system has a residence time between about 5 days and about four weeks.

In one embodiment, the gastric residence system has a residence time between about 6 days and about four weeks. In one embodiment, the gastric residence system has a residence time between about 7 days and about four weeks. In one embodiment, the gastric residence system has a residence time between about 10 days and about four weeks. In one embodiment, the gastric residence system has a residence time between about 14 days and about four weeks. In one embodiment, the gastric residence system has a residence time between about three weeks and about four weeks.

In one embodiment, the gastric residence system has a residence time between about 24 hours and about one month. In one embodiment, the gastric residence system has a residence time between about 48 hours and about one month. In one embodiment, the gastric residence system has a residence time between about 72 hours and about one month. In one embodiment, the gastric residence system has a residence time between about 96 hours and about one month. In one embodiment, the gastric residence system has a residence time between about 5 days and about one month. In one embodiment, the gastric residence system has a residence time between about 6 days and about one month. In one embodiment, the gastric residence system has a residence time between about 7 days and about one month. In one embodiment, the gastric residence system has a residence time between about 10 days and about one month. In one embodiment, the gastric residence system has a residence time between about 14 days and about one month. In one embodiment, the gastric residence system has a residence time between about three weeks and about one month.

The gastric residence system releases a therapeutically effective amount of therapeutic agent during at least a portion of the residence time or residence period during which the system resides in the stomach. In one embodiment, the system releases a therapeutically effective amount of therapeutic agent during at least about 25% of the residence time. In one embodiment, the system releases a therapeutically effective amount of therapeutic agent during at least about 50% of the residence time. In one embodiment, the system releases a therapeutically effective amount of therapeutic agent during at least about 60% of the residence time. In one embodiment, the system releases a therapeutically effective amount of therapeutic agent during at least about 70% of the residence time. In one embodiment, the system releases a therapeutically effective amount of therapeutic agent during at least about 75% of the residence time. In one embodiment, the system releases a therapeutically effective amount of therapeutic agent during at least about 80% of the residence time. In one embodiment, the system releases a therapeutically effective amount of therapeutic agent during at least about 85% of the residence time. In one embodiment, the system releases a therapeutically effective amount of therapeutic agent during at least about 90% of the residence time. In one embodiment, the system releases a therapeutically effective amount of therapeutic agent during at least about 95% of the residence time. In one embodiment, the system releases a therapeutically effective amount of therapeutic agent during at least about 98% of the residence time. In one embodiment, the system releases a therapeutically effective amount of therapeutic agent during at least about 99% of the residence time.

Methods of Treatment Using the Gastric Residence Systems

The gastric residence systems can be used to treat conditions requiring administration of a therapeutic agent over an extended period of time. For long-term administration of a therapeutic agent, which may be taken for months, years, or indefinitely, administration of a gastric residence system once weekly, once every two weeks, or once a month can provide substantial advantages in patient compliance and convenience.

Once a gastric residence system has been administered to a patient, the system provides sustained release of therapeutic agent over the period of gastric retention. After the period of gastric retention, the system degrades and passes out of the stomach. Thus, for a system with a gastric retention period of one week, the patient will swallow (or have administered to the stomach via other means) a new system every week. Accordingly, in one embodiment, a method of treatment of a patient with a gastric retention system of the invention having a gastric residence period of a number of days D (where D-days is the gastric residence period in days), over a total desired treatment period T-total (where T-total is the desired length of treatment in days) with the therapeutic agent in the system, comprises introducing a new gastric residence system every D-days into the stomach of the patient, by oral administration or other means, over the total desired treatment period. The number of gastric residence systems administered to the patient will be (T-total) divided by (D-days). For example, if treatment of a patient for a year (T-total=365 days) is desired, and the gastric residence period of the system is 7 days (D-days=7 days), approximately 52 gastric residence systems will be administered to the patient over the 365 days, as a new system will be administered once every seven days.

Kits and Articles of Manufacture

Also provided herein are kits for treatment of patients with the gastric residence systems of the invention. The kit may contain, for example, a sufficient number of gastric residence systems for periodic administration to a patient over a desired total treatment time period. If the total treatment time in days is (T-total), and the gastric residence systems have a residence time of (D-days), then the kit will contain a number of gastric residence systems equal to ((T-total) divided by (D-days)) (rounded to an integral number), for administration every D-days. The kit may contain, for example, several gastric residence systems in containers (where the containers may be capsules) and may optionally also contain printed or computer readable instructions for dosing regimens, duration of treatment, or other information pertinent to the use of the gastric residence systems and/or the therapeutic agent contained in the gastric residence systems. For example, if the total treatment period prescribed for the patient is one year, and the gastric residence system has a residence time of one week, the kit may contain 52 capsules, each capsule containing one gastric residence system, with instructions to swallow one capsule once a week on the same day (e.g., every Saturday).

Articles of manufacture, comprising a sufficient number of gastric residence systems for periodic administration to a patient over a desired total treatment time period, and optionally comprising instructions for dosing regimens, duration of treatment, or other information pertinent to the use of the gastric residence systems and/or the therapeutic agent contained in the gastric residence systems, are also included in the invention. The articles of manufacture may be supplied in appropriate packaging, such as dispensers, trays, or other packaging that assists the patient in administration of the gastric residence systems at the prescribed interval.

Manufacture/Assembly of Exemplary System

A stellate or star-shaped design embodiment of the gastric residence system can be assembled by preparing carrier polymer-agent components as "arms" in the shape of elongate members, where the arms are attached to a central elastomer. When the arms are prepared in the shape of a cylinder, they comprise a flat proximal end (one base of the cylinder, the first base), a distal end (the other base of the cylinder, a second base), and a curved outer surface therebetween enclosing the volume of the cylinder. The arms can also be prepared in the shape of triangular prisms, rectangular prisms, or other shapes.

Figure 2C:
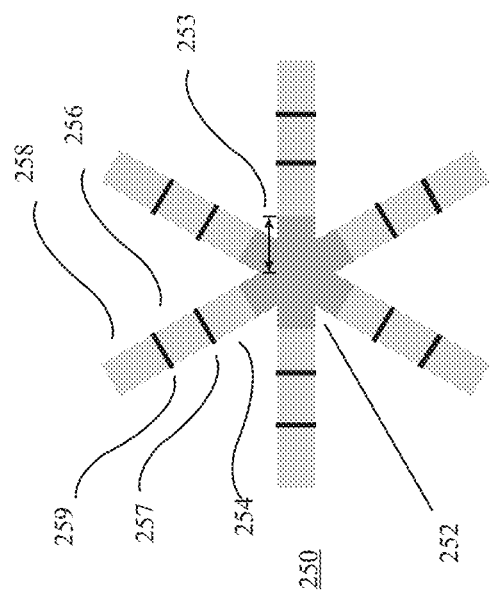
FIG. 2C shows another embodiment of a gastric residence system of the invention.

The central elastomer of the gastric residence system can be prepared in the shape of an "asterisk," such as element 252 of one embodiment of the gastric residence system 250 shown in FIG. 2C. In FIG. 2C, central elastomer 252 is asterisk-shaped; the branches of the asterisk are attached to carrier polymer-agent segment 254; segment 254 is attached to carrier polymer-agent segment 256 via enteric linker 257; segment 256 is attached to carrier polymer-agent segment 258 via enteric linker 259; and the assembly of 254-257-256-259-258 forms one arm of the system 250. The elongate members (arms) comprised of segments of carrier polymer-agent components, shown as 254-257-256-259-258 in FIG. 2C, can then be attached to the ends of each branch of the asterisk by melt interfacing, adhesives, solvent welding, or other methods.

Example 10 describes preparation of carrier polymer-agent component "arms" (Section A) and central elastomer (Section B).

Manufacture of gastric residence systems of the invention can be performed by a method comprising:

A. Forming a flexible coupling polymer component. In some embodiments, the flexible coupling polymer component is asterisk-shaped with a plurality of at least three branches.

B. Forming a plurality of at least three carrier polymer-agent components, which are elongate members comprising a proximal end and a distal end.

Note that forming step A and forming step B can be performed in any order, or simultaneously.

C. Attaching the elongate members to the flexible coupling polymer component. When the elongate members are attached, and in the absence of any external constraining forces, the resulting assembly is the gastric residence system in its uncompacted form. The elongate members are attached to the flexible coupling polymer component such that, in its uncompacted form, the gastric residence system has at least two perpendicular dimensions, each dimension of at least two centimeters, that is, the gastric residence system measures at least about 2 cm in length over at least two perpendicular directions; or the perimeter of the gastric residence system in its uncompacted state, when projected onto a plane, has two perpendicular dimensions, each of at least 2 cm in length. (Further possible values for the lengths of the perpendicular dimensions are provided in the section describing System Dimensions.)

In order to place the gastric residence system into a capsule or other container for administration to a patient, a further step can be performed, comprising:

D. Compacting the gastric residence system and inserting the system into a container, such as a capsule, suitable for oral administration or administration through a gastric tube or feeding tube.

As explained above and as will be described in further detail below, the primary focus of the present disclosure relates to systems and methods for encapsulation of the gastric residence system.

Step A, the formation of a flexible coupling polymer, can be performed by any method suitable for preparing a shaped polymer, such as by injection molding, gravity molding, compression molding, extrusion, or three-dimensional printing. The flexible coupling polymer can be formed in the shape of a ring, a torus, a sphere, an oblate ellipsoid (also called an oblate spheroid, an ellipsoid, or an oblate sphere), or any other shape which has at least one axis of rotational symmetry, such as a cube or a rectangular cuboid. Optionally, the shape of the flexible coupling polymer can have branches, protrusions, or convexities where the carrier polymer-agent components which are elongate members can be attached. Optionally, the shape of the flexible coupling polymer can have indentations, concavities, dimples, or recesses where the carrier polymer-agent components which are elongate members can be attached.

Step B, the formation of the plurality of at least three carrier polymer-agent components, in the shape of elongate members, can likewise be performed by any suitable method for making shaped polymers, such as injection molding, gravity molding, compression molding, extrusion, or three-dimensional printing using the carrier polymer-agent mixture. Prior to formation, the therapeutic agent is milled as described herein, and then mixed with the appropriate carrier polymer, dispersant, and other ingredients as described herein. The elongate members can be formed in the shape of solid rectangular prisms, solid triangular prisms, or solid cylinders; solid cylinders are preferred. Additionally, as noted herein, the elongate members can be formed from two, three, or more segments which are coupled by coupling polymers, preferably coupled by enteric polymers. Elongate members can be formed by joining together segments using butt joints (that is, the end of one segment can be joined to the end of another segment by adhesion, such as by a film of enteric polymer between and adhering to the ends of both of the segments), or by melting segments together, or can be formed by joining together segments using collar joints (that is, a film of an enteric polymer can be wrapped around the ends of two segments, joining them together).

Step C, attaching the carrier polymer-agent component elongate members to the flexible coupling polymer component, can be performed by various methods, such as melt interfacing, adhesives, solvent welding, or any other method suitable for attachment of polymers. If the flexible coupling polymer has branches, collar joints can be used for attaching the carrier polymer-agent component elongate members to the flexible coupling polymer component. The attachments of the carrier polymer-agent component elongate members to the flexible coupling polymer component can be formed using enteric polymers. Once the carrier polymer-agent components are attached to the flexible coupling polymer component, the gastric residence system will be in its uncompacted form in the absence of any external constraining forces.

Step D, compacting the gastric residence system and inserting the system into a container, can be performed either manually or mechanically, by compacting, folding, or compressing the gastric residence system into its compacted configuration, and insertion of the system into a capsule or other container of appropriate size. Techniques for compacting the gastric residence system and encapsulating the system into a container will be discussed in more detail below.

Compacting and Encapsulation of System

Following are the details of embodiments for systems and methods of compacting and encapsulating a compactable gastric residence systems. In some embodiments, the compactable gastric residence systems can include a linking member linking one or more segments.

In some embodiments, the methods can include one or more of the following:

A. Receiving the compactable gastric residence system in an uncompacted form. In some embodiments, the compactable gastric residence system can be received, for example, at a vibratory bowl feeder or a pick and place conveyor.

B. Orienting the compactable gastric residence system into a compacting position.

C. Compacting the compactable gastric residence system into a compacted form.

D. Inserting the compactable gastric residence system in the compacted form into an opening of a container. In some embodiments, the compactable gastric residence system can be secured in the compacted form by a retaining element such as a band or a cap prior to insertion into the container to minimize pressure on the capsule and/or prevent expansion of the compactible gastric system if the capsule is damaged or in case of early deployment.

Figure 4B:
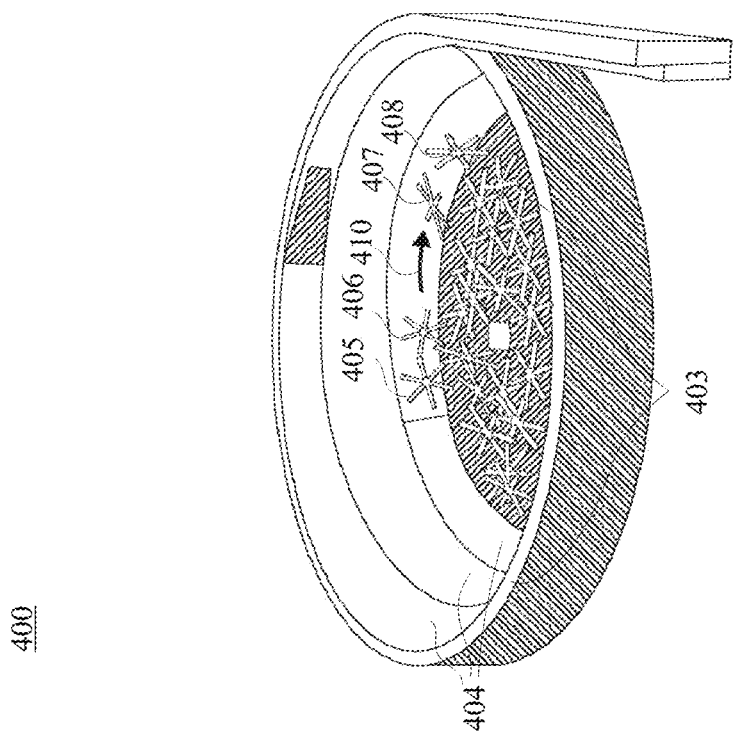
FIGS. 4A-4D show an exemplary vibratory bowl feeder for aligning and propagating gastric residence systems toward a sorting system.
Figure 4A:
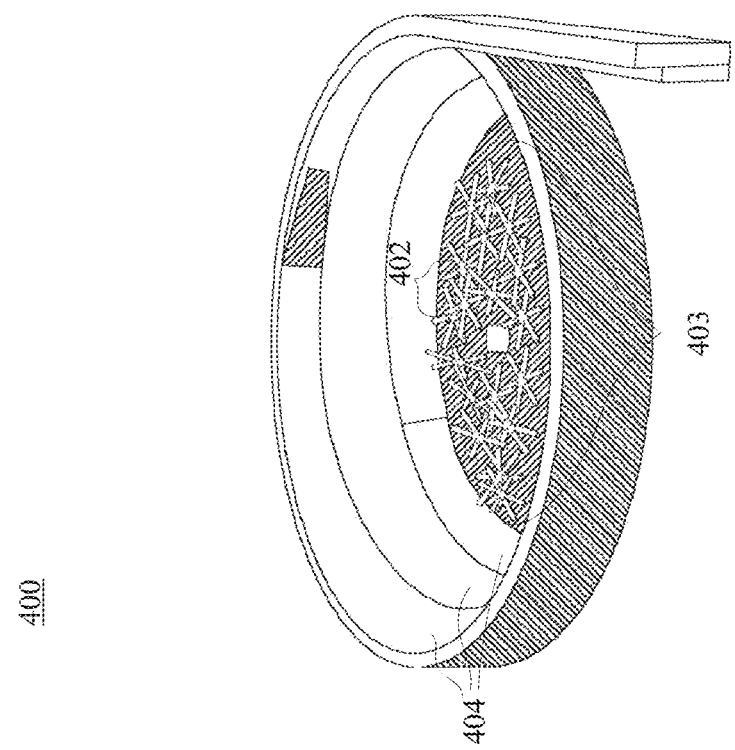

FIGS. 4A-4D show an exemplary vibratory bowl feeder 400 for aligning and propagating gastric residence systems 402 toward a sorting fixture (not shown). In FIG. 4A, a bulk deposit 403 of gastric residence systems 402 can be deposited into the vibratory bowl feeder 400 with the individual gastric residence systems being oriented in different directions. In some embodiments, the extended arms of stellate form gastric residence systems 402 can become entangled together. In this situation, it can become difficult to grab and/or pick individual gastric residence systems for placing into position for compacting and encapsulation. In should be understood that other forms of gastric residence systems besides the stellate form can similarly become entangled resulting in the same difficulties. In some embodiments, vibrations of the vibratory bowl feeder 400 can cause the gastric residence systems to shift position and disengage from one another. FIG. 4B shows a small number individual gastric residence systems 405, 406, 407, and 408 that may separate from the bulk deposit near the center of the vibratory bowl feeder and begin to ascend along a spiraling track 404 of the feeder as the gastric residence systems are propelled by the vibration. As shown, the gastric residence systems can ascend with different orientations such as the orientation of gastric residence systems 405 and 406 as compared to gastric residence system 407. As exemplary direction of motion of the gastric residence systems as they are moved by the vibration of the bowl feeder is shown by the arrow showing 410.

Figure 4D:
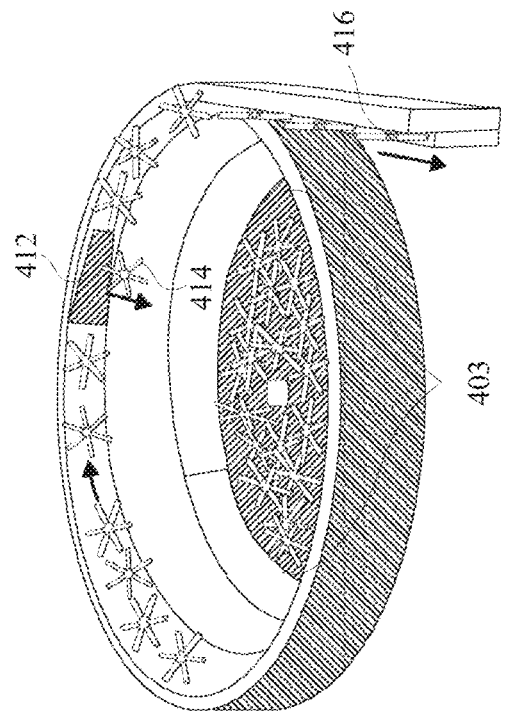
Figure 4C:
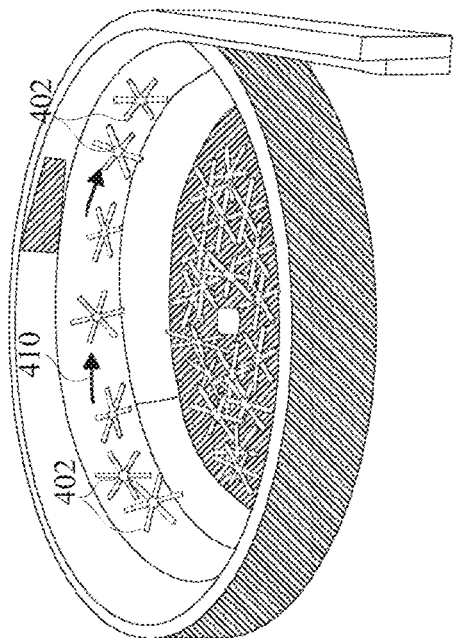

FIG. 4C shows gastric resident systems further ascending up the spiraling track of the vibratory bowl feeder. In some embodiments, the shape and material properties spiral track can be designed to cause the gastric residence systems to orient themselves into a favorable orientation for delivery to downstream equipment. The gastric residence systems can continue generally in the same direction of motion shown by arrows 410 as previously shown in FIG. 4B. While gastric residence systems 402 are only shown occupying one level of the ascending spiral track in FIG. 4C, it should be understood that gastric residence systems from the bulk 403 at the bottom of the vibratory bowl feeder 400 will continue to separate from the bulk and move upward along the lower levels of the spiral as shown in FIG. 4B while the shown gastric residence systems continue to ascend up higher levels of the ascending spiral track. FIG. 4D shows the gastric residence systems reaching the top of the ascending spiral track and reaching an orientation filter 412, the orientation fixture can be a mechanical structure that prevents gastric residence systems that are not in the desired orientation (e.g., 414) from passing to the end of the ascending spiral track. In some embodiments, gastric residence systems reaching the orientation filter 412 in the incorrect orientation can be ejected back into the bulk 403 at the bottom of the vibratory bowl feeder 400. In some embodiments, the orientation fixture can also be used to realign gastric residence systems that are not in the desired orientation that reach the fixture rather than ejecting those gastric residence systems back to the bulk. Gastric residence systems that are ejected in this manner can return to the bulk deposit at the bottom of the vibratory bowl feeder where the process can be repeated from beginning until a particular gastric residence system reaches the filter in the prior orientation.

FIGS. 4A-4D show an embodiment of a vibratory bowl feed for gastric residence systems of the stellate configuration, e.g., as shown in FIGS. 2A-2C above. However, it should be understood that other forms of gastric residence systems (e.g., a ring shaped design as shown in FIG. 1) can be used without departing from the scope of the present disclosure. Further, although stellate configurations with six arms are shown, it should be understood that the vibratory bowl feeder can be used with stellate configurations with N arms (where N is greater than or equal to three) such that the system can have at least two perpendicular dimensions as described above in regards to FIG. 2B.

FIGS. 5A-5D show an embodiment of a pick and place system 500 for placing gastric residence systems into position for compacting into a compacted for by a compacting fixture. FIG. 5A shows a robotic arm 502 including tooling tip 504 that is configured to engage with a portion of the gastric residence system. In one embodiment, the tooling tip can be a vacuum cup that has a surface shape that is configured to mate with a surface shape of a gripping portion of the gastric residence system 506. In some embodiments, the gripping portion of the gastric residence system 506 can be a concave surface, a convex surface, or a smooth and flat surface. A corresponding vacuum tooling tip can be convex, concave or smooth and flat respectively to maximize suction between the tooling tip and the gastric residence system gripping portion. In some embodiments, the tooling tip 504 can be a pneumatic gripping arm. In some embodiments, the tooling tip can be a needle that stabs the gripping portion of the gastric residence system.

In some embodiments, the gripping portion of the gastric residence system can be a protrusion that is formed on the gripping portion 508 of the gastric residence system. In some embodiments, the protrusion can be shaped like a handle and the gripping portion of the pneumatic gripping arm can engaged with the handle. In some embodiments the pneumatic gripping arm can engaged directly with an outer surface of the gripping portion 508 of the gastric residence system. In some embodiments, the robotic arm 502 can utilize optical recognition techniques to recognize the presence and orientation of a gastric residence system. The gastric residence system 506 can be positioned on a surface 510. In some embodiments, the surface 510 can be a conveyor belt for bringing the gastric residence system into proximity with the robot arm for picking and placing into position for compacting. In some embodiments, the surface 510 can be any surface that is relatively flat.

FIG. 5B shows the robotic arm 502 positioning into a contact position with the gastric residence system 506 to engage with the gripping portion of the gastric residence system. FIG. 5C shows the robotic arm 502 lifting the gastric residence system 506 away from the surface 510 and FIG. 5D shows the gastric residence system placed onto a fixture 512 for compacting the gastric residence system and preparing the gastric residence system for encapsulation in a container.

Figure 6A:
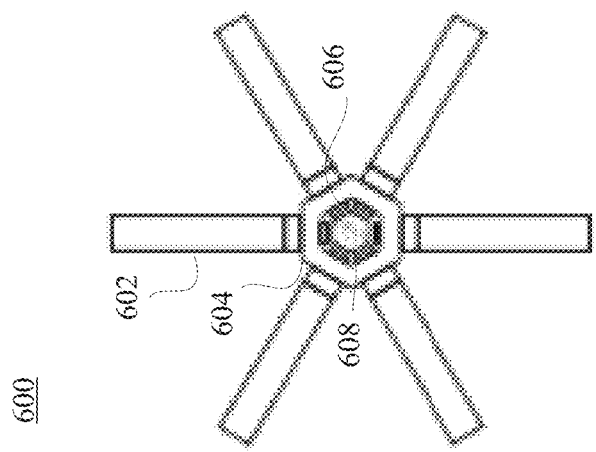
Figure 6B:
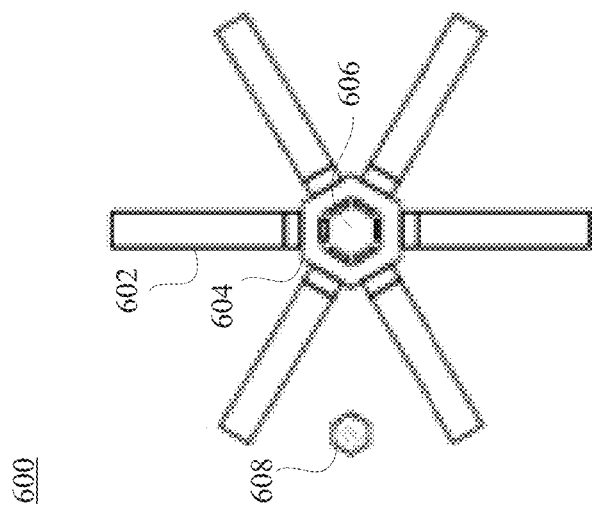

FIGS. 6A-6D show an additional embodiment of a pick and place system 600 for placing gastric residence systems into position for compacting into a compacted for by a compacting fixture. FIG. 6A shows a top view of a gastric residence system 602 having a stellate form with six extended arms extending from a flexible linking member 604 with an aperture 606 through the center of the linking member. In some embodiments, the geometry of the linking member opening can be a torus shape. The linking member can be made of a flexible material such as an elastomer as described above. A tooling tip 608 for a robotic arm (e.g., as described above regarding FIGS. 5A-5D can be an expandable hexagonal head that can fit within the aperture in the linking member 604 of the gastric residence system 602. FIG. 6B shows the expandable hexagonal head tool tip 608 positioned within the aperture 606 in the linking member 604 prior to expansion of the head.

FIG. 6C shows the expandable hexagonal head tooling tip 608 after expansion of the head within the aperture 606 of the linking member 604. The flexible linking member 604 can deform slightly from the outward force provided by the expandable hexagonal head tooling tip 608, thus gripping the gastric residence system through friction. FIG. 6D shows the positioning of the gastric residence system as gripped by the expandable hexagonal head tool tip 608 onto a fixture 612 for compacting and encapsulation in a container. It should be recognized that the embodiment described in FIGS. 6A-6D provides an additional variation of the tooling tip attached to a robotic arm as described above.

Figure 7C:
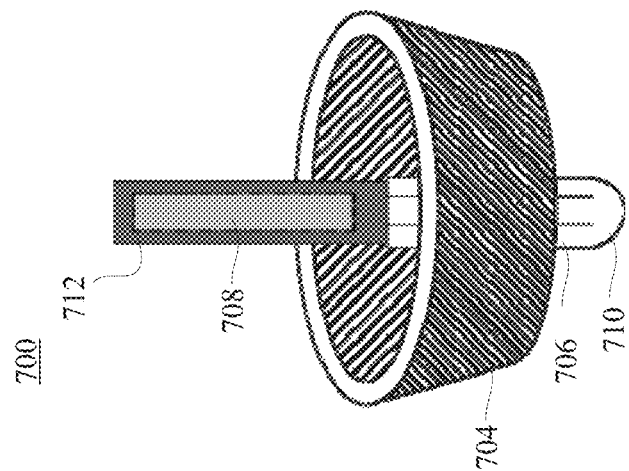
FIGS. 7A-7C show a first exemplary compacting system for compacting gastric residence systems and inserting the gastric residence systems into a container.
Figure 7B:
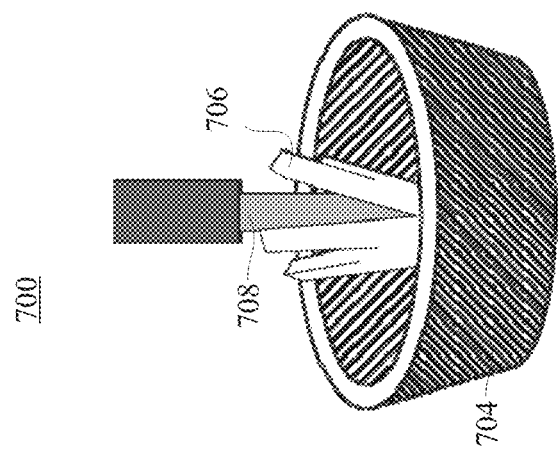
Figure 7A:
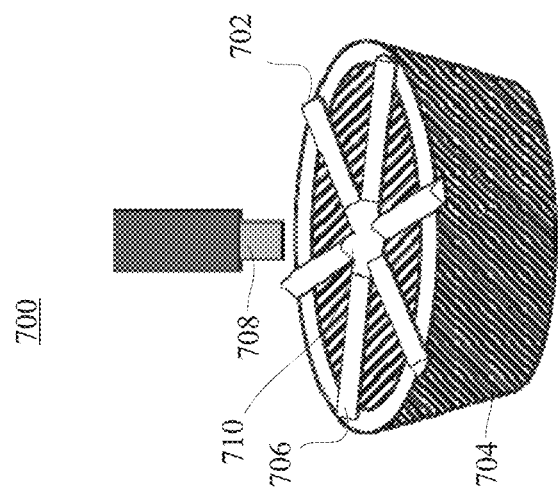

FIGS. 7A-7C show a first exemplary compacting system 700 for compacting gastric residence systems 702 and inserting the gastric residence systems into a container such as a pill capsule. In some embodiments, the tapered tube can correspond to the fixtures 512 and 612 described above. In some embodiments, the gastric residence system can be placed on top of a tapered tube 704 sized such that arms of the gastric residence system can sit flush on the surface of the tube. In some embodiments, the diameter of the opening of the tube can be sized such that distal ends of the arms 706 rest on the edge of the opening in the tapered tube 704. In some embodiments, a primary piston 708 can be configured to apply a force to a linking member 710 of the gastric residence system 702. The force applied by the primary piston to the linking member 710 of the gastric residence system can cause the arms 706 to fold. The initial force can be applied to the distal ends 706 of the arms of the gastric residence system 702, thus providing maximum leverage to overcome the minimum bending force of the gastric residence system.

In some of the embodiments of the gastric residence systems described herein, a bending force of the gastric residence system is at least about 0.1 newtons in the position when the arms are not bent by any bending force (such as shown in FIG. 7A). In some of the embodiments of the gastric residence systems described herein, the gastric residence system has a bending force of at least about 0.2 newtons when the arms are bent more than about 5 degrees from the position occupied when not subjected to a bending force. In some of the embodiments of the gastric residence systems described herein, the gastric residence system has a bending force of at least about 0.4 newtons when the arms are bent more than about 5 degrees from the position occupied when not subjected to a bending force. In some of the embodiments of the gastric residence systems described herein, the gastric residence system has a bending force of at least about 0.2 newtons when the arms are bent more than about 10 degrees from the position occupied when not subjected to a bending force. In some of the embodiments of the gastric residence systems described herein, the gastric residence system has a bending force of at least about 0.6 newtons when the arms are bent more than about 10 degrees from the position occupied when not subjected to a bending force. In some of the embodiments of the gastric residence systems described herein, the gastric residence system has a bending force of at least about 0.2 newtons when the arms are bent more than about 45 degrees from the position occupied when not subjected to a bending force (e.g., as illustrated in FIG. 7C). In some of the embodiments of the gastric residence systems described herein, the gastric residence system has a bending force of at least about 1.5 newtons when the arms are bent more than about 45 degrees from the position occupied when not subjected to a bending force. In some embodiments, the gastric residence system has a bending force of at most about 6.5 newtons. In some embodiments, the gastric residence system has a bending force of at most about 4.0 newtons. In some embodiments, the gastric residence system has a bending force of at most about 2.0 newtons.

FIG. 7B shows the gastric residence system 702 has been partially folded or compacted application of force by the primary piston 708. As the force is applied to the gastric residence system 702 by the primary piston 708, the walls of the tapered tube 704 can gradually press the arms 706 inward toward the piston, gradually bringing the arms closer together as the gastric residence system is pressed through the tapered tube. In some embodiments, the surfaces of the tapered tube 704 that come in contact with the gastric residence system 702 can be polished to reduce roughness and sharp edges that may cause damage to the gastric residence system. In some embodiments, surfaces of the tube that come in contact with the gastric residence system 702 can be coated with a low friction coating such as biocompatible fluoropolymers. Further, by decreasing friction between the gastric residence system and the tapered tube, any coatings or pharmaceutical agents applied to the exterior of the gastric residence system can be preserved. FIG. 7B further shows that after some point in the tapered tube 704 and depending on the thickness of the primary piston 708, the piston can become trapped between the arms 706 and the piston can prevent further folding of the gastric residence system into a compacted form. One solution to this problem is to reduce the thickness of the piston to allow the gastric residence system to close sufficiently to be pressed into a container. However, if the thickness of the piston because too small, the force applied by the primary piston 708 to the linking member 710 of the gastric residence system 702 may puncture or otherwise damage the structure of the gastric residence system.

In some embodiments, a minimum contact surface area of the piston is preferably about 15 square millimeters. In some embodiments, a minimum contact surface area of the piston is preferably about 28 square millimeters. In some embodiments, a minimum contact surface area of the piston is preferably about 35 square millimeters. In some embodiments, an overly large primary piston 708 may prevent the gastric residence system from sufficiently folding for the folding and compacting process to be completed with additional processing steps as described below in FIG. 7C. The contact surface area of the primary piston 708 can be the limiting factor again because the arms will be closest together at the ends attached to the linking member 710 of the gastric residence system. Accordingly, the maximum contact surface area of the primary piston is preferably about 20 square millimeters. In some embodiments, the maximum contact surface area of the primary piston is preferably about 33 square millimeters. In some embodiments, the maximum contact surface area of the primary piston is preferably about 40 square millimeters. In some embodiments, the maximum contact surface area of the primary piston is preferably about 80 square millimeters.

FIG. 7C shows a second stage of the exemplary compacting system during a second stage. In some embodiments, the primary piston 708 can retract while a secondary piston having a larger contact area 712 can engage with the distal ends of the arms 706 of the gastric residence system 702 to continue pressing the gastric residence system through the tapered funnel 704 until the gastric residence system is fully folded into a compacted state. In some embodiments, the fully compacted state will result in adjacent arms 706 of the gastric residence system being in contact with one another. In some embodiments, the fully compacted state will allow the arms to have a minimum space gap from a nearest adjacent arm. The opening at the bottom of the tapered tube 704 can be slightly larger than an opening of a container (not shown) that will receive the compacted gastric residence system. In some embodiments, the container can be a half-capsule. After the gastric residence system 702 is fully inserted to the half-capsule, the full encapsulation of the gastric residence system in a capsule can be completed. As will be discussed below regarding FIGS. 8A-8B, a tapered tube 704 may also be used to compact the gastric residence system 702 for insertion into containers other than a capsule or half-capsule.

In some embodiments, the diameter of the top opening of the tapered tube 704 can be at least about 30 millimeters. In some embodiments, the diameter of the top opening of the tapered tube 704 can be at least about 40 millimeters. In some embodiments, the diameter of the top opening of the tapered tube 704 can be at least about 45 millimeters.

In some embodiments, the diameter of the top opening of the tapered tube 704 can be at most about 35 millimeters. In some embodiments, the diameter of the top opening of the tapered tube 704 can be at most about 45 millimeters. In some embodiments, the diameter of the top opening of the tapered tube 704 can be at most about 50 millimeters.

In some embodiments, the diameter of the opening at the bottom of the tapered tube 704 can be at least about 8.2 millimeters. In some embodiments, the diameter of the opening at the bottom of the tapered tube 704 can be at least about 9.8 millimeters.

In some embodiments, the taper angle of the tapered tube can be at least about 5 degrees. In some embodiments, the taper angle of the tapered tube can be at least about 15 degrees. In some embodiments, the taper angle of the tapered tube can be at least about 30 degrees. In some embodiments, the taper angle of the tapered tube can be at least about 45 degrees. In some embodiments, the taper angle of the tapered tube can be at most about 15 degrees. In some embodiments, the taper angle of the tapered tube can be at most about 30 degrees. In some embodiments, the taper angle of the tapered tube can be at most about 45 degrees. In some embodiments, the taper angle of the tapered tube can be at most about 60 degrees.

In some embodiments there is a gap between the arms or the folded portions of the gastric residence system. In some embodiments, this gap can help prevent damage to the surfaces of the gastric residence system during storage. This gap can also prevent adhesions of the surfaces of the gastric residence system that contact each other. In some embodiments, the preferred minimum space gap between adjacent arms of the gastric residence system in the compacted state is preferably about 0.01 millimeters. In some embodiments, the preferred minimum space gap between adjacent arms of the gastric residence system in the compacted state is preferably about 0.05 millimeters. In some embodiments, the preferred minimum space gap between adjacent arms of the gastric residence system in the compacted state is preferably about 0.1 millimeters. In some embodiments, the preferred minimum space gap is preferably about 0.2 millimeters. It should be noted that an excessively large gap provided between the arms 706 can mean that that size of the capsule needs to be increased or the size of the gastric residence system needs to be decreased. Accordingly, in some embodiments the preferred maximum space gap between adjacent arms of the gastric residence system is about 0.07 millimeters. In some embodiments the preferred maximum space gap between adjacent arms of the gastric residence system is about 0.15 millimeters. In some embodiments the preferred maximum space gap between adjacent arms of the gastric residence system is about 0.25 millimeters.

Figure 8B:
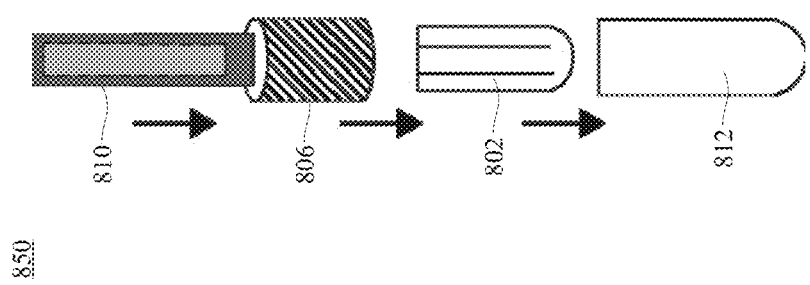
FIGS. 8A-8B show an exemplary compacting system configured to sequentially inserting gastric residence systems into a cartridge that can simultaneously hold multiple compacted gastric residence systems.
Figure 8A:
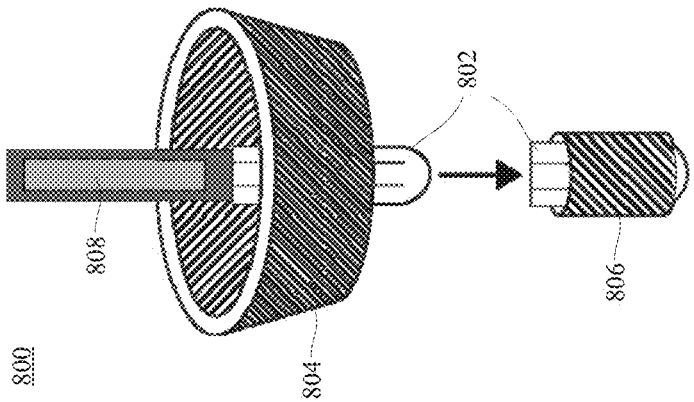

FIGS. 8A-8B show an exemplary compacting system 800 configured to sequentially inserting gastric residence systems 802 into a cartridge 806 that can simultaneously hold multiple compacted gastric residence systems. A compacting system 804 is shown as a tapered tube, however it should be understood that any suitable compacting system capable of compacting a gastric residence system 802 as disclosed throughout the present disclosure could be used without departing from the scope of the present disclosure. As described above, one or more pistons 808 can be used to press the gastric residence system 802 into the compacted form and pass it through an aperture. In some embodiments, rather than inserting the compacted gastric residence system 802 into a capsule, the gastric residence system can be placed into a cartridge 806 that is configured to hold multiple gastric residence systems. As a gastric residence system passes through the aperture of the compacting system 800, the piston can push the gastric residence system against the contents of the cartridge 806 until the gastric residence system is completely inserted into the cartridge. This process can be repeated until a desired number of gastric residence systems 802 are inserted into the cartridge. In some embodiments, a filled cartridge 806 can immediately be moved to a separate system for inserting into a container. In some embodiments, a filled cartridge 806 can be moved into storage until insertion in a container is desired.

FIG. 8B shows an exemplary insertion system 850 according to examples of the disclosure. As shown, a cartridge 806 containing compacted gastric residence systems 802 can be positioned between a container (e.g., a half-capsule) and a piston 810. In some embodiments, the piston 810 can apply force to a gastric residence system at one end of the cartridge 806 and a different gastric residence system can emerge from the opposite end of the cartridge to be inserted into the container 812. It should be noted that although a large space is shown between the cartridge 806 and the container 812 in FIG. 8B, it is desirable to minimize the gap between the cartridge 806 and the container 812 so that the gastric residence system does not have an opportunity to open itself from the compacted position. The insertion system can continue to press the piston 810 through the cartridge 806 providing a separate container for each gastric residence system 802 until the cartridge contents are exhausted. The piston 810 can then be removed from the cartridge 806 and another loaded cartridge replace the exhausted cartridge, allowing the process to be repeated quickly. Because the gastric residence systems 802 in the cartridge 806 do not need to be individually compacted, the process of inserting the residence systems into capsules can be performed very quickly. In some embodiments, a maximum time between sequentially inserting gastric residence systems from a cartridge into individual containers can preferably be less than about 15 seconds. In some embodiments, a maximum time between sequentially inserting gastric residence systems from a cartridge into individual containers can preferably be less than about 5 seconds. In some embodiments, a maximum time between sequentially inserting gastric residence systems from a cartridge into individual containers can preferably be less than about 0.5 seconds. In some embodiments, a maximum time between sequentially inserting gastric residence systems from a cartridge into individual containers can preferably be less than about 0.02 seconds.

FIGS. 9A-9C show a second exemplary compacting system 900 for compacting gastric residence systems 902 and inserting the gastric residence system into a container. In the exemplary compacting system 900, a gastric residence system can be placed on top of a mechanical aperture 904. In some examples, the mechanical aperture 904 can correspond to the fixtures 512 and 612 described above. In some embodiments, the initial size of the opening 910 in then mechanical aperture 904 can be selected such that distal ends of the arms 906 contact the edge of the opening in the mechanical aperture. In some embodiments, piston 908 can be configured to apply a force to a linking member 912 of the gastric residence system 902. The force applied by the primary piston to the linking member 912 of the gastric residence system can cause the arms 906 to fold. The initial force can be applied to the distal ends 906 of the arms of the gastric residence system 902, thus providing maximum leverage to overcome the minimum bending force of the gastric residence system. In some embodiments of the gastric residence systems described herein, the gastric residence system has a bending force of at least about 0.1 newtons. In some embodiments of the gastric residence systems described herein, the gastric residence systems has a bending force within the minimum values, maximum values, and ranges associated with different bending angles as described above regarding FIGS. 7A-7D.

FIG. 9B shows the compacting system 900 after the gastric residence system 902 has been partially folded or compacted after an application of force by the primary piston 908. As the force is applied to the gastric residence system 902 by the primary piston 908, the opening 910 in the mechanical aperture 904 can gradually be reduced in size to press the arms 906 inward toward the piston, gradually bringing the arms closer together as the gastric residence system is pressed and the opening is reduced in size. In some embodiments, the surface area of the mechanical aperture that comes in contact with the gastric residence system 902 can be applied to a much smaller portion of the surface of the gastric residence system when compared to the compacting systems 700 and 800 described above. In particular, once the initial force is applied by the piston, the closing mechanical aperture 904 can be the primary source of force for further compacting the gastric residence system. In some embodiments, the mechanical aperture can be configured to mate with a notch or groove in the arms of the gastric residence system. In this way, the gastric residence system can be prevented from sliding while being compacted and prevent damage by friction to the exterior of the gastric residence system including coatings as previously described above. In some embodiments, the piston 908 can continue applying force only until an angle of at least about 75 degrees is formed between the initial position of the arms 906 and the partially compacted position of the arms. By decreasing the area on the surface of that gastric residence system that experiences friction, any coatings applied to the exterior of the gastric residence system can be preserved. FIG. 9B further shows that after some amount of closure of the opening 910 in the mechanical aperture 904, and depending on the thickness of the primary piston 908, the piston can become trapped between the arms 906 and the piston can prevent further folding of the gastric residence system into a compacted form. One solution to this problem is to reduce the thickness of the piston to allow the gastric residence system to close sufficiently to be pressed into a container. However, if the thickness of the piston because too small, the force applied by the primary piston 908 to the linking member 910 of the gastric residence system 902 may puncture or otherwise damage the structure of the gastric residence system.

In some embodiments, a minimum contact surface area of the piston is preferably about 15 square millimeters. In some embodiments, a minimum contact surface area of the piston is preferably about 28 square millimeters. In some embodiments, a minimum contact surface area of the piston is preferably about 35 square millimeters. In some embodiments, an overly large primary piston 908 may prevent the gastric residence system from sufficiently folding for the folding and compacting process to be completed with additional processing steps as described above in FIG. 7C. The contact surface area of the primary piston 908 can be the limiting factor again because the arms will be closest together at the ends attached to the linking member 912 of the gastric residence system. Accordingly, the maximum contact surface area of the primary piston is preferably about 20 square millimeters. In some embodiments, the maximum contact surface area of the primary piston is preferably about 33 square millimeters. In some embodiments, the maximum contact surface area of the primary piston is preferably about 40 square millimeters. In some embodiments, the maximum contact surface area of the primary piston is preferably about 80 square millimeters.

FIG. 9C shows a second stage of the exemplary compacting system during a second stage. In some embodiments, the primary piston 908 can retract while a secondary piston having a larger contact area 912 can engage with the distal ends of the arms 906 of the gastric residence system 902 to continue pressing the gastric residence system through the tapered funnel 904 until the gastric residence system is fully folded into a compacted state. In some embodiments, the fully compacted state will result in adjacent arms 906 of the gastric residence system being in contact with one another. In some embodiments, the fully compacted state will allow the arms to have a minimum space gap from a nearest adjacent arm. The opening at the bottom of the tapered tube 904 can be slightly larger than an opening of a container (not shown) that will receive the compacted gastric residence system. In some embodiments, the container can be a half-capsule. After the gastric residence system 902 is fully inserted to the half-capsule, the full encapsulation of the gastric residence system in a capsule can be completed. As discussed above regarding FIGS. 8A-8B, a mechanical aperture 904 may also be used to compact the gastric residence system 902 for insertion into containers other than a capsule or half-capsule.

In some embodiments, the preferred minimum space gap between adjacent arms of the gastric residence system in the compacted state is preferably about 0.01 millimeters. In some embodiments, the preferred minimum space gap between adjacent arms of the gastric residence system in the compacted state is preferably about 0.05 millimeters. In some embodiments, the preferred minimum space gap between adjacent arms of the gastric residence system in the compacted state is preferably about 0.1 millimeters. In some embodiments, the preferred minimum space gap is preferably about 0.2 millimeters. It should be noted that an excessively large gap provided between the arms 906 can mean that that the amount of therapeutic agent available to be delivered by the gastric residence system may not be maximized for a given available volume of the container. Accordingly, in some embodiments the preferred maximum space gap between adjacent arms of the gastric residence system is about 0.07 millimeters. In some embodiments the preferred maximum space gap between adjacent arms of the gastric residence system is about 0.15 millimeters. In some embodiments the preferred maximum space gap between adjacent arms of the gastric residence system is about 0.25 millimeters.

Figure 10B:
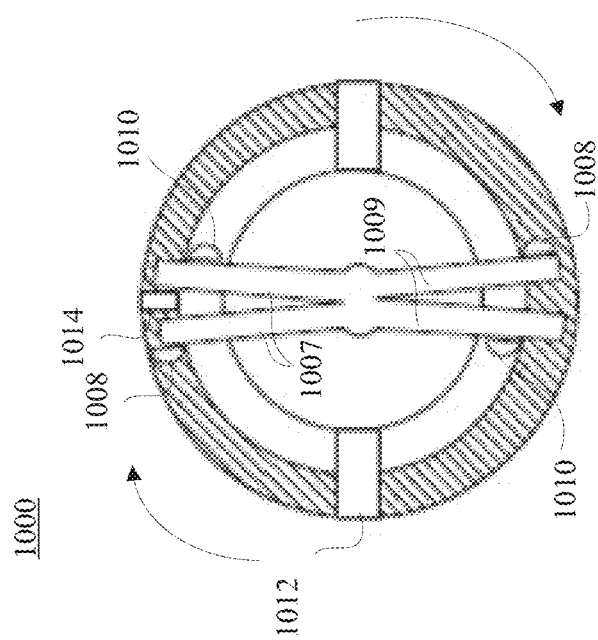
Figure 10A:
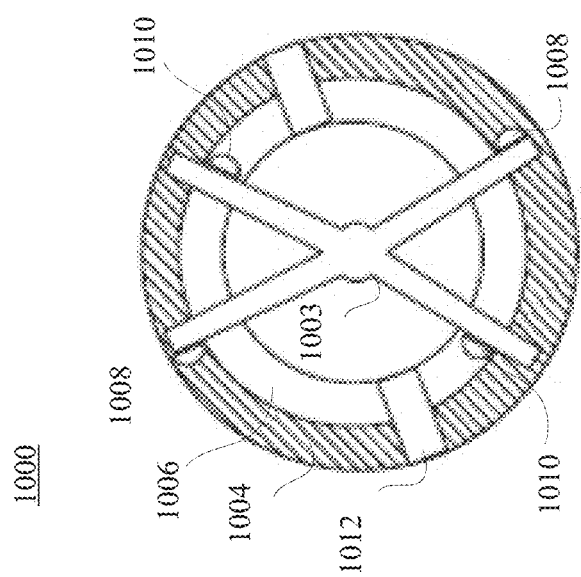

FIGS. 10A-10D show a third exemplary compacting system 1000 according to examples of the disclosure. FIG. 10A illustrates a gastric residence system 1002 having four arms extending from a linking member 1003 and placed upon a dual rotational plate in an initial position. In some embodiments, the dual rotational plate can include an external rotational plate 1004 and an internal rotational plate 1006. In some embodiments, external mounting blocks 1008 and internal mounting blocks 1010 can be positioned on the respective rotational plates to engage with the arms of the gastric residence system 1002 in an uncompacted form. The gastric residence system can be placed directly into the position and orientation shown in FIG. 10A by a pick and place system such as the embodiments described in FIGS. 5A-5D and 6A-6D above and the dual rotational plate can correspond to fixtures 512 and 612 respectively. In some embodiments, the external rotational plate 1004 can include flexible hinge sections 1012 that can allow the external rotational plate to fold in half along the hinge. FIG. 10B illustrates the dual rotational plate in a final position where the top pair of arms 1007 and the bottom pair of arms 1009 of the gastric residence system 1002 are each respectively brought closer to each other by a clockwise rotation of the external rotational plate 1004 and a counterclockwise rotation of the internal rotational plate 1006. In some embodiments, a stop 1014 can be included to prevent the pairs of arms from being pressed together an possibly becoming fused. In some embodiments, the stop can also prevent any coatings on the surface of the gastric residence system 1002 from being rubbed by individual arms being pressed together. FIG. 10C shows a side view of the compacting system 1000, with the gastric residence system resting on top of the dual rotational plate and the hinge 1012 shown aligned with the linking member 1003 of the gastric residence system 1002. With the arms of the gastric residence system 1002 brought together by the dual rotational plate, the compacting system can fold along the hinge 1012 into the folded configuration shown in FIG. 10D. The folding can bring the top arms 1007 and bottom arms 1009 together to place the gastric residence system 1002 into the a fully compacted form. Once the gastric residence system 1002 has been placed in the compacted form, the gastric residence system can be pressed out of the folded dual rotational block (e.g., by a piston) into a container. It should be understood that although the example of FIGS. 10A-10D is shown with a gastric residence system having four arms, an analogous system could be used for grouping arms and compacting gastric residence systems having three or more arms without departing from the scope of the present disclosure.

Figure 11A:
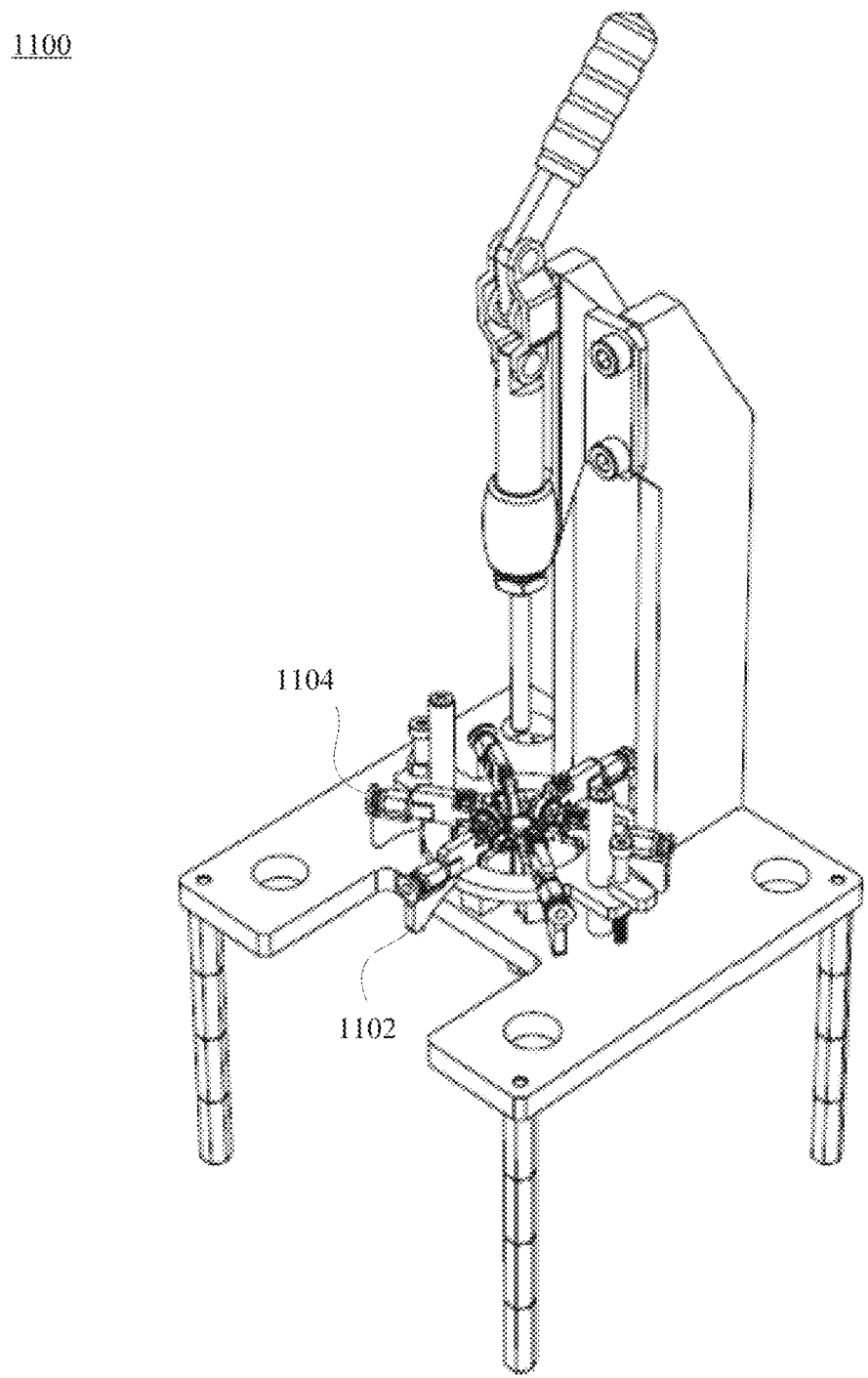
FIGS. 11A-11D show a fourth exemplary compacting system according to examples of the disclosure.
Figure 11B:
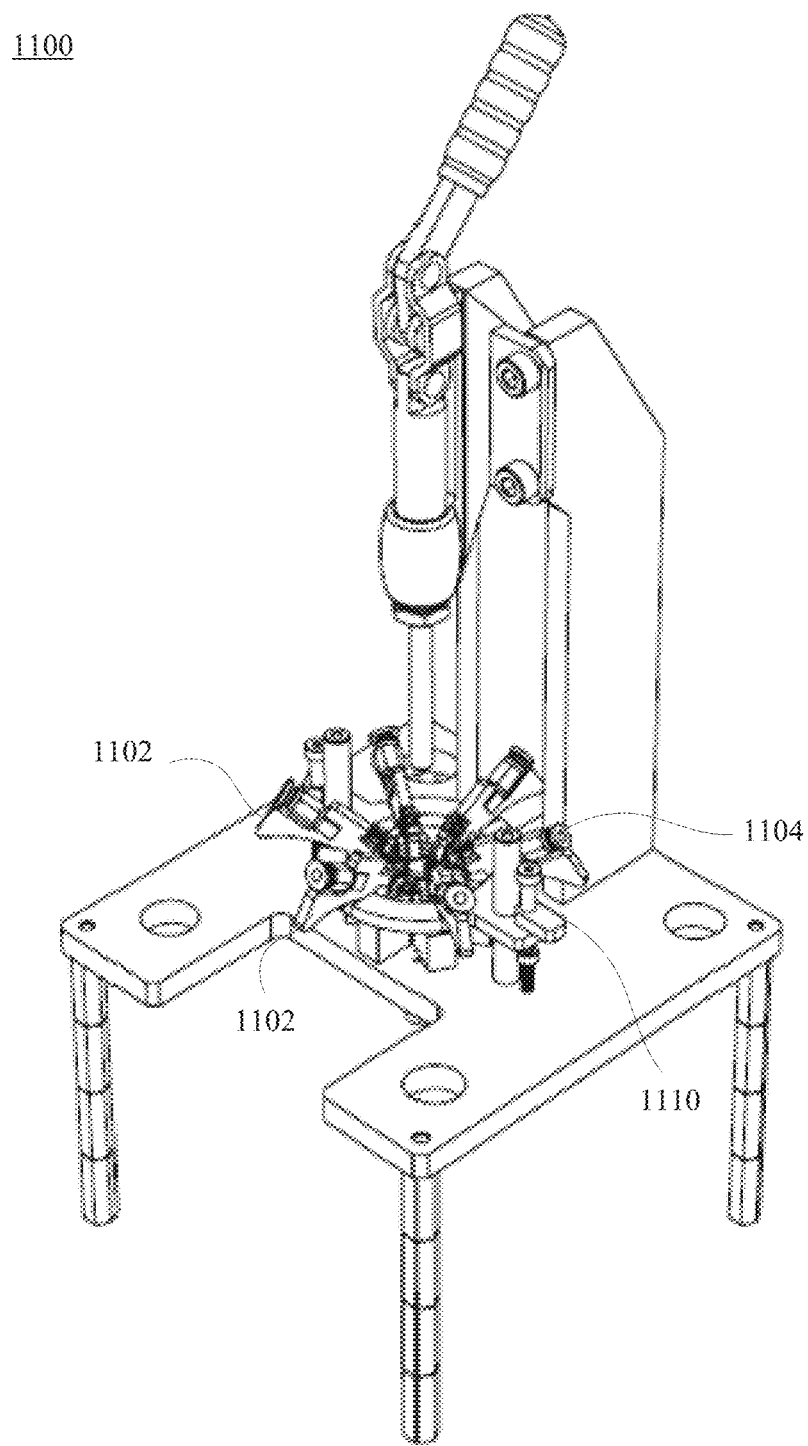
Figure 11C:
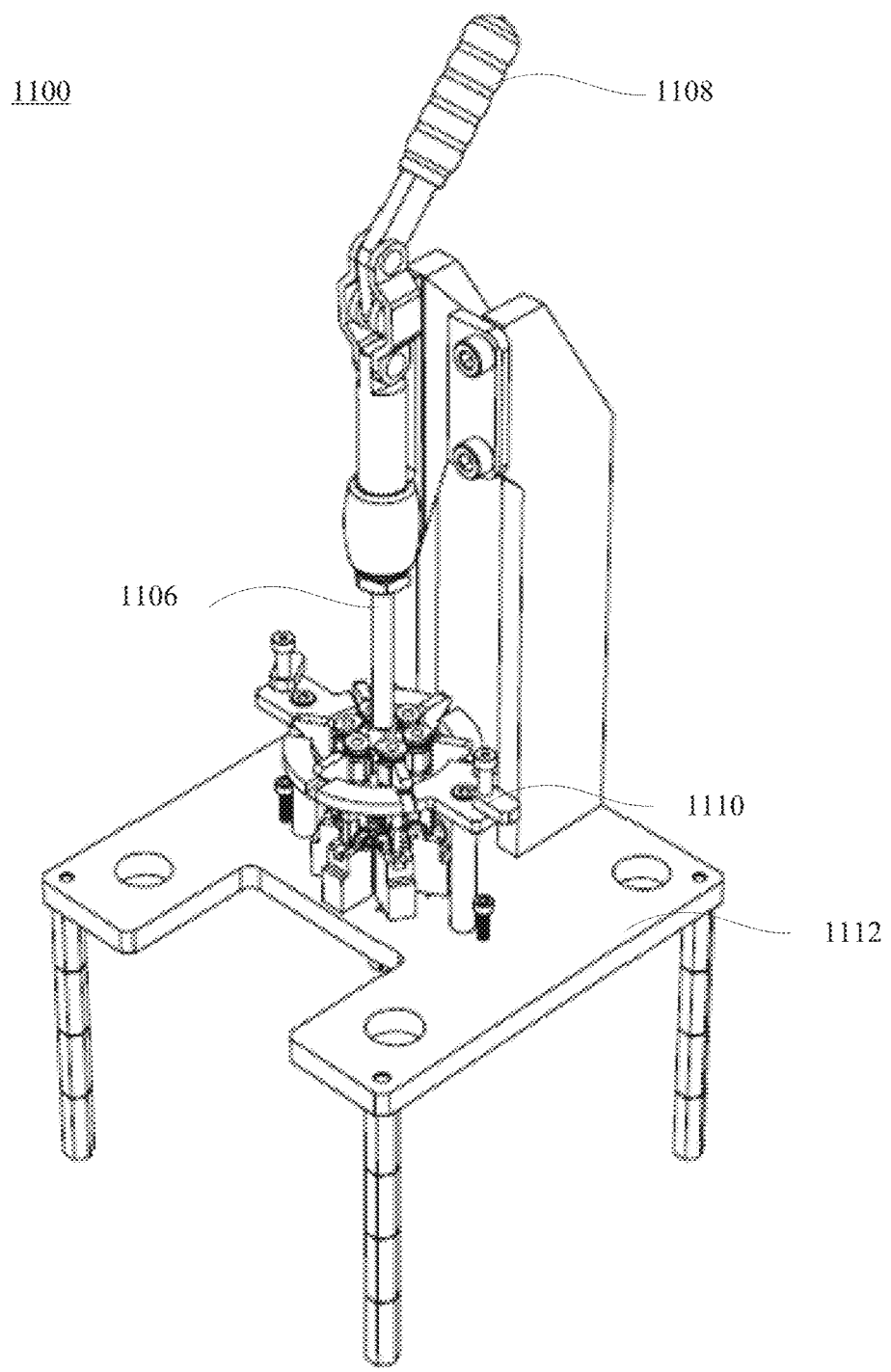
Figure 11D:
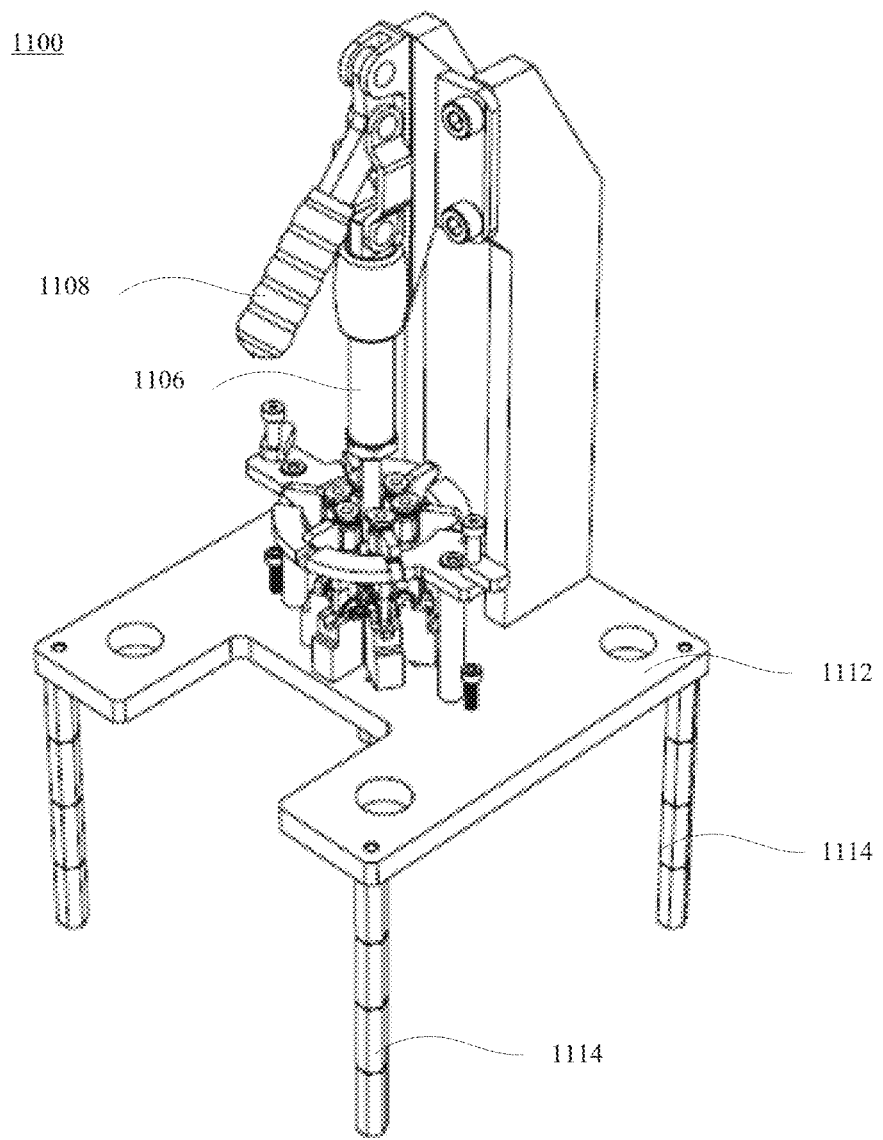

FIGS. 11A-11D show a fourth exemplary compacting system 1100 according to examples of the disclosure. The compacting system 1102 can include a number of rotatable hinges 1102 corresponding to a position and number of arms of a gastric residence system (not shown) to be compacted and inserted into a container. In the illustrated FIGURE, six rotatable hinges 1102 are shown corresponding to a gastric residence system with six arms. A gastric residence system can be placed directly into a position and orientation with arms aligned with the rotatable hinges 1102 by a pick and place system such as the embodiments described in FIGS. 5A-5D and 6A-6D above. At the tip of each of the rotatable hinges 1102 there can be vacuum line connections 1104 for creating suction at vacuum cups on the rotatable hinges 1102. The vacuum cups can pull the arms of the gastric residence system securely onto the rotatable hinges 1102 as they are rotated. FIG. 11B illustrates the rotatable hinges 1102 in a partially rotated position which can correspond to a partially compacted gastric residence system as shown in FIGS. 7B and 9B above. The rotatable hinges can be pushed up by a pushing fixture 1110 that pushes up on all six of the rotatable hinges 1102 simultaneously and evenly such that each of the arms of the gastric residence system can close at the same rate. FIG. 11C illustrates the rotatable hinges 1102 in a position corresponding to a fully compacted gastric residence system as shown in FIGS. 7C and 9C above. In FIG. 11C the pushing fixture 1110 can more clearly be seen elevated from the base platform of the compacting system 1100. As further shown, a piston 1106 can be positioned directly above the final position of the compacted gastric residence system. In some embodiments, the piston can be operable by a lever 1008 that can be controlled manually or by a robotic arm. In some embodiments, the piston itself can be controlled to rise up and down without the need for a lever 1008. FIG. 11D illustrates the piston 1006 and level 1008 in a lowered position. When the piston 1006 is lowered, the gastric residence system can be pressed out of the compacting system through an opening in the base plate 1112. In some embodiments, actuation of the piston 1006 can interrupt the suction of the vacuum cups to prevent damage to the gastric residence system as it is being pushed out from the compacting system. In some embodiments, the base plate 1112 can be elevated by legs 1114 to allow space for containers to pass beneath the structure of the compacting system 1100 and receive the gastric residence systems.

Figure 12A:
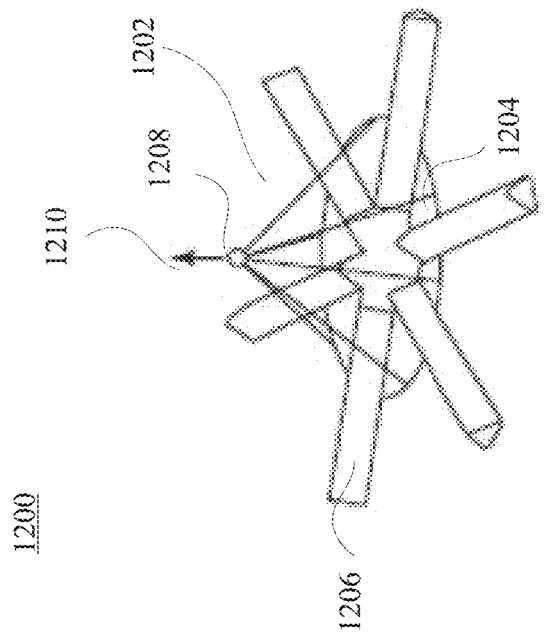
FIGS. 12A-12D show an exemplary compacting system for compacting a gastric residence system using a flexible runner that can interconnect extended portions of the gastric residence system.
Figure 12B:
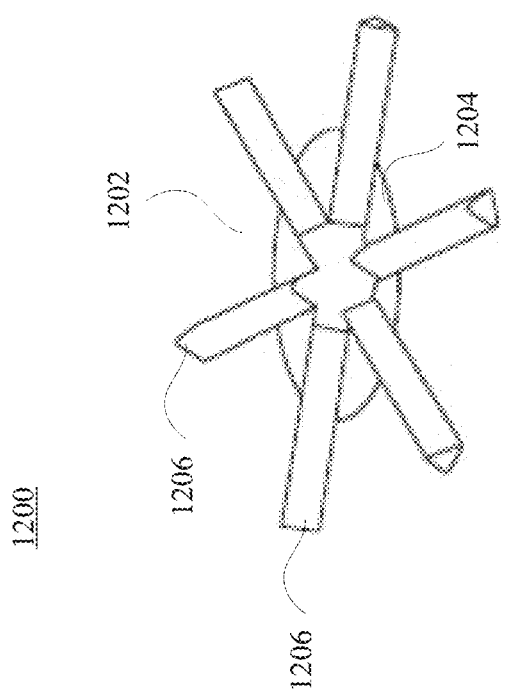
Figures 12C, 12D:
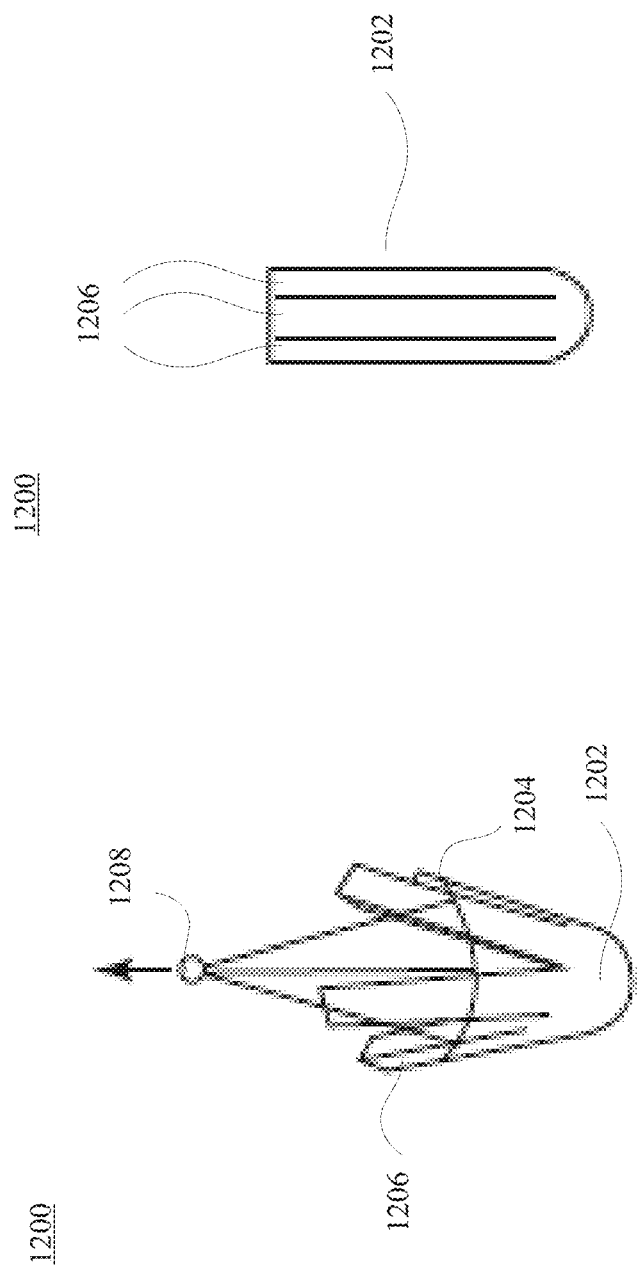

FIGS. 12A-12D show an exemplary compacting system 1200 for compacting a gastric residence system 1202 using a flexible runner 1204 that can interconnect extended portions 1206 of the gastric residence system. In some embodiments, during formation of the gastric residence system 1202, a flexible runner system can interconnect adjacent arms 1206 of the gastric residence system 1202 as shown in FIG. 12A. In some embodiments, the flexible runner system 1204 can be formed by an injection molding process simultaneously to the formation of the gastric residence system. FIG. 12B shows an anchor system 1208 that can be used to grip the flexible runner 408 between the arms. An upward force in the direction of arrow 1210 can be applied to the anchor system, which can subsequently cause the runner system 1204 to pull on the arms 1206. FIG. 12C shows the gastric residence system 1202 partially folded or compacted as a result of the upward force applied by the anchor system

1208. In some embodiments, upward force can continue to be applied until the gastric residence system 1202 is fully compacted as shown in FIG. 12D. In some embodiments, the flexible runner 1204 can placed inside of the arms 1206 (and thus not visible in the drawing). In some embodiments, the flexible runner can be removed. As will be discussed in further detail below regarding FIGS. 13A-13B and FIG. 14 below, a retaining fixture can be added to the gastric residence system 1202 to maintain the structure in the compacted form prior to insertion into a container. In some embodiments, the anchor system 1208 can be used in conjunction with a secondary compacting system as described above to provide a partial folding of the gastric residence system 1202 that can be completed along with the insertion of the gastric residence system into a container. For example, the partially compacted gastric residence system 1202 shown in FIG. 12C could be placed into the mechanical aperture of FIGS. 9A-9D with a partially closed opening, replacing the function of the initial pressing by a first piston. Once the partially compacted gastric residence system 1202 of FIG. 12C is placed into the mechanical aperture 904 above, the closure of the aperture could complete the compacting of the gastric residence system, for example.

Figures 13A, 13B:
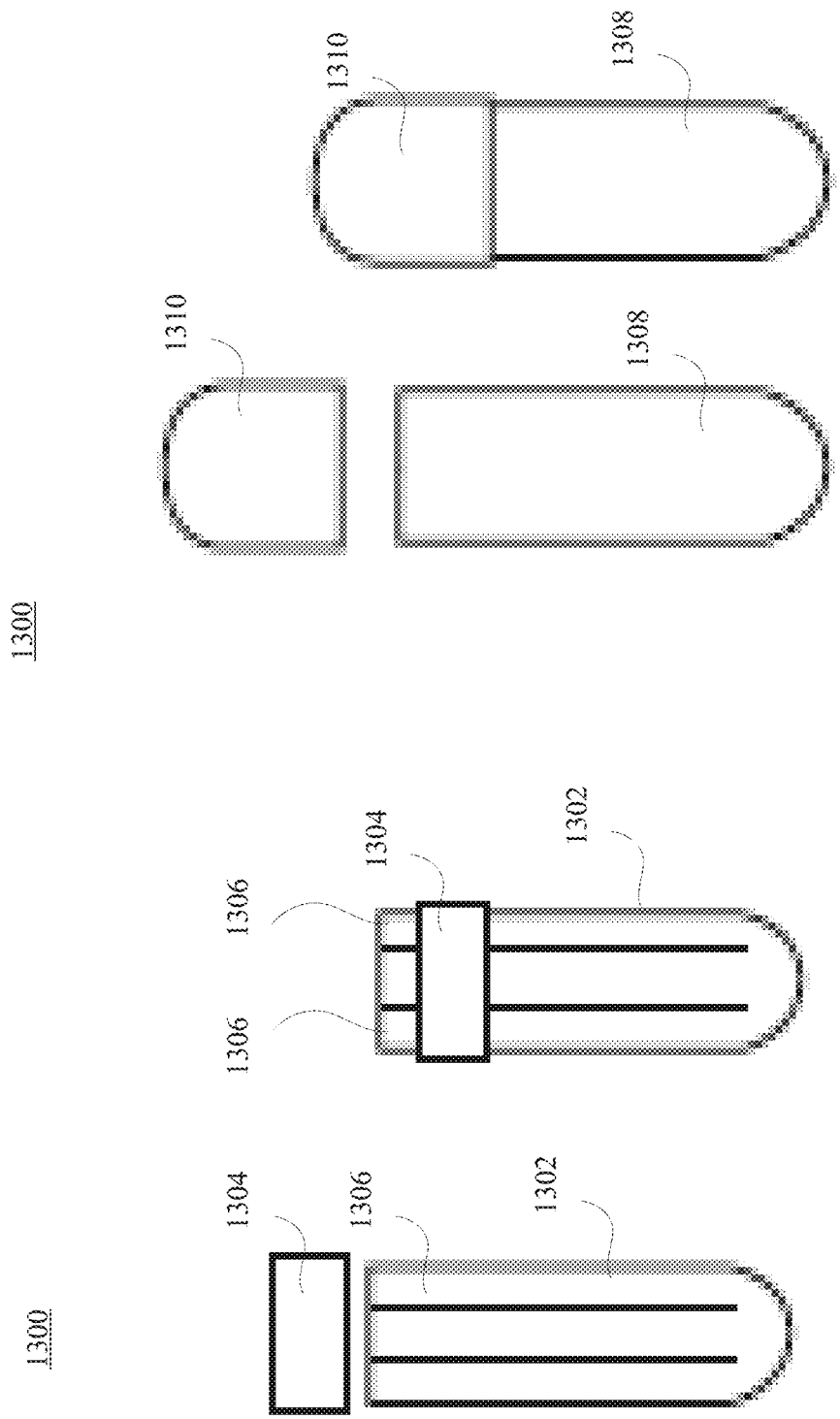
FIGS. 13A and 13B show a retaining band for maintaining a gastric residence system in a compacted form.

FIGS. 13A and 13B show a retaining band 1304 for maintaining a gastric residence system in a compacted form. FIG. 13A shows a retaining band 1304 can be placed over one end of the gastric residence system 1302 in a compacted form. The retaining band 1304 can slide over the end of the gastric residence system 1402 and be placed near the distal ends of the arms 1306 of the gastric residence system to prevent the gastric residence system from prematurely expanding in the case of an early deployment of the gastric residence system. In some examples, the retaining band can be made of materials well-known in the art, such as gelatin or hydroxypropyl methylcellulose. In one embodiment, the retaining band 1304 is made of a material that dissolves in the gastric environment, but not in the oral or esophageal environment, which prevents premature release of the system prior to reaching the stomach. FIG. 13B shows a capsule container for the gastric residence system 1302 after that band has been applied. In some embodiments, the thickness of the band can provide spacing between the interior surface of the capsule and the gastric residence system. In some embodiments, the spacing between the interior surface of the capsule and the gastric residence system can be determined by the thickness of the retaining band 1304. In some embodiments, a preferred minimum thickness for the retaining band 1304 can be at least about 0.01 millimeters. In some embodiments, a preferred minimum thickness for the retaining band 1304 can be at least about 0.05 millimeters. In some embodiments, a preferred minimum thickness for the retaining band 1304 can be at least about 0.1 millimeters. In some embodiments, a preferred minimum thickness for the retaining band 1304 can be at least about 0.2 millimeters. Alternatively, an excessively thick retaining band 1304 can result in significant wasted space within the container. In some embodiments, a preferred maximum thickness of the retaining band 1304 can be at most about 0.1 millimeters. In some embodiments, a preferred maximum thickness of the retaining band 1304 can be at most about 0.2 millimeters. In some embodiments, a preferred maximum thickness of the retaining band 1304 can be at most about 0.5 millimeters.

Figure 14:
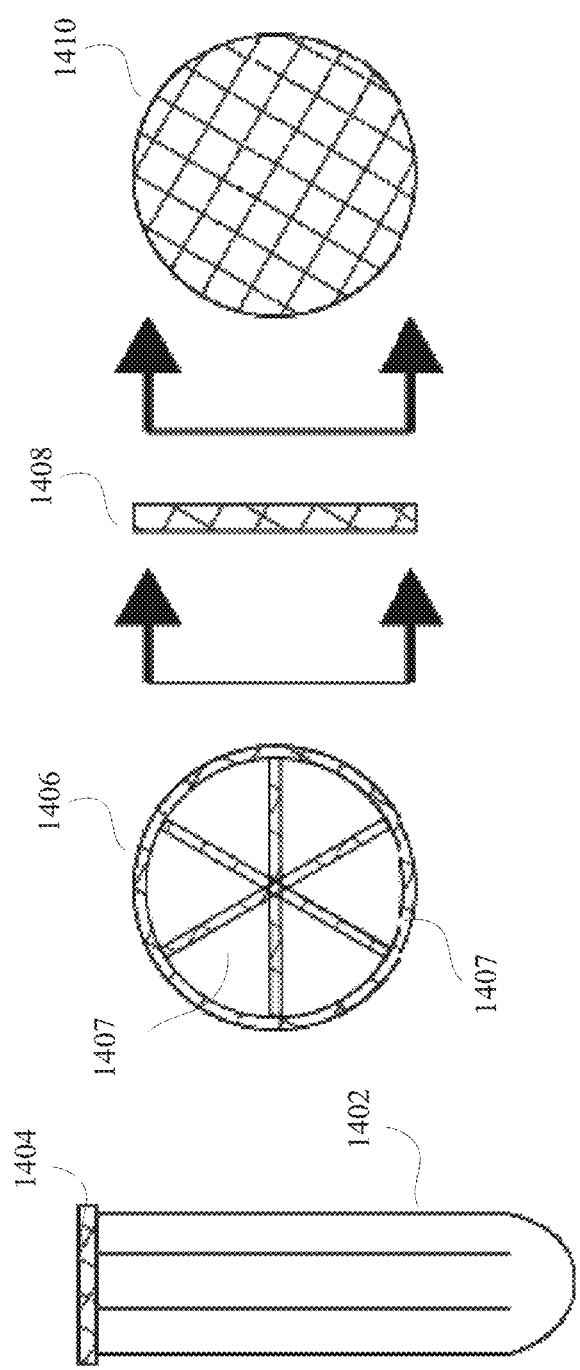
FIG. 14. shows a retaining cap for maintaining a gastric residence system in a compacted form.

FIG. 14. shows a retaining cap 1404 for maintaining a gastric residence system 1402 in a compacted form. Similar to the concept of the retaining band above, a retaining cap 1404 can be used to maintain a gastric residence system 1402 in a compacted form. FIG. 14 provides multiple views of the retaining cap 1404 including a bottom view 1406, a side view 1408, and a top view 1410. The bottom view 1406 of the retaining cap 1406 shows small cavities 1407 that can be configured to have the same overall shape as the cross-section of arms of the gastric residence system 1402. By matching the shapes of the cavities 1407 and the cross section of the arms of the gastric residence system 1402, the retaining cap can engage with the arms in the compacted form of the gastric residence system to hold the arms in place. The retaining cap 1404 can be configured to engage with a small surface area of the gastric residence system 1402, and because of the cavities 1407 that engage with the arms of the gastric residence system, the cap also does not require sliding into place beyond the distal ends of the arms. Thus, interference with coatings on the gastric residence system 1402 by the retaining cap 1404 can be minimized while still preventing the gastric residence system from prematurely expanding in the case of an early deployment of the gastric residence system. In some examples, the retaining cap 1404 can be made of materials well-known in the art, such as gelatin or hydroxypropyl methylcellulose. In one embodiment, the retaining cap 1404 is made of a material that dissolves in the gastric environment, but not in the oral or esophageal environment, which prevents premature release of the system prior to reaching the stomach. As with the description of FIG. 13B above, the gastric residence system 1402 secured by the retaining cap 1404 can be inserted into a container capsule. In some embodiments, a thickness of an outer rim 1409 of the retaining band can provide spacing between the interior surface of the capsule and the gastric residence system. In some embodiments, the spacing between the interior surface of the capsule and the gastric residence system can be determined by the thickness of the retaining cap rim 1409. In some embodiments, a preferred minimum thickness of the retaining cap rim 1409 can be at least about 0.01 millimeters. In some embodiments, a preferred minimum thickness of the retaining cap rim 1409 can be at least about 0.05 millimeters. In some embodiments, a preferred minimum thickness for the retaining cap rim 1409 can be at least about 0.1 millimeters. In some embodiments, a preferred minimum thickness for the retaining cap rim 1409 can be at least about 0.2 millimeters. In some embodiments, a preferred minimum thickness for the retaining cap 1409 can be at least about 0.5 millimeters. Alternatively, an excessively thick retaining cap rim 1409 can result in significant wasted space within the container. In some embodiments, a preferred maximum thickness of the retaining cap rim 1409 can be at most 0.1 millimeters. In some embodiments, a preferred maximum thickness of the retaining cap rim 1409 can be at most 0.2 millimeters. In some embodiments, a preferred maximum thickness of the retaining cap rim 1409 can be at most 0.5 millimeters. In some embodiments, a preferred maximum thickness of the retaining cap rim 1409 can be at most 0.2 millimeters. In some embodiments, a preferred maximum thickness of the retaining cap rim 1409 can be at most 1 millimeter. In some embodiments, a preferred maximum thickness of the retaining cap rim 1409 can be at most 1.25 millimeters.

FIGS. 15A-19D show techniques for mechanical constraining the gastric residence systems as described throughout the disclosure for the additional of additional mechanical stability and safety of delivery of the gastric residence systems.

Figure 15A:
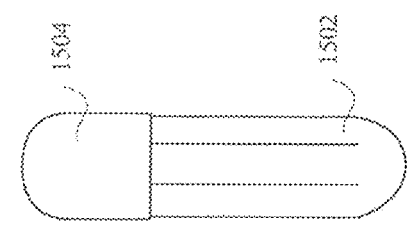
FIGS. 15A-15D show an exemplary technique for mechanically securing a gastric residence system using a cap.
Figure 15B:
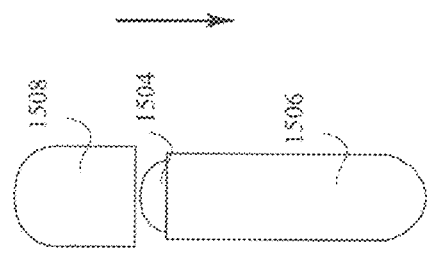
Figure 15C:
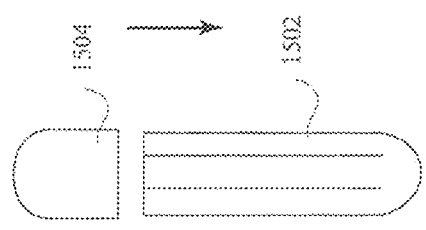
Figure 15D:
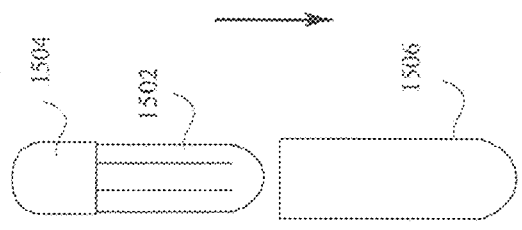

FIGS. 15A-15D show a technique for mechanically securing a gastric residence system 1502 using a cap 1504 (otherwise referred to as a half-capsule herein) of a capsule that is smaller than the final container of the gastric residence system. FIG. 15A shows that the cap 1504 can be secured over the extended portions of the gastric residence system prior to actually securing the cap over the extended portions of the gastric residence system, and FIG. 15B shows the cap 1504 secured over the end of the extended portions of the gastric residence system. FIG. 15C shows the gastric residence system 1502 with cap 1504 can be inserted into container 1506 having a larger size than the cap 1504. FIG. 15D shows a slight protrusion of the cap 1504 after insertion into the capsule body 1506. In some embodiments, the length of the gastric residence system 1502 can be such that there is no protrusion of the cap 1504 beyond the opening of the capsule body 1506 without departing from the scope of the present disclosure. Furthermore, in some embodiments, the end of the gastric residence system 1502 that is secured by the cap 1504 can be inserted into the capsule body 1506 with the non-secured end of the gastric residence system facing toward the opening in the capsule body without departing from the scope of the present disclosure. Finally, FIG. 15D illustrates that a cap 1508 corresponding to the size of the capsule body 1506 can be used to form a closed container containing the gastric residence system 1502. In this configuration, the cap 1504 can continue to provide mechanical security for the gastric residence system 1502 within the larger container formed by capsule body 1506 and cap 1508. In some embodiments, the thickness of the cap can provide spacing between the interior surface of the capsule and the gastric residence system. In some embodiments, the spacing between the interior surface of the capsule and the gastric residence system can be determined by the thickness of the cap 1504. In some embodiments, a preferred minimum thickness for the cap 1504 can be at least about 0.01 millimeters. In some embodiments, a preferred minimum thickness for the cap 1504 can be at least about 0.05 millimeters. In some embodiments, a preferred minimum thickness for the cap 1504 can be at least about 0.1 millimeters. In some embodiments, a preferred minimum thickness for the cap 1504 can be at least about 0.2 millimeters. Alternatively, an excessively thick cap 1504 can result in significant wasted space within the container. In some embodiments, a preferred maximum thickness of the cap 1504 can be at most 0.1 millimeters. In some embodiments, a preferred maximum thickness of the cap 1504 can be at most 0.2 millimeters. In some embodiments, a preferred maximum thickness of the cap 1504 can be at most 0.5 millimeters.

Figure 16B:
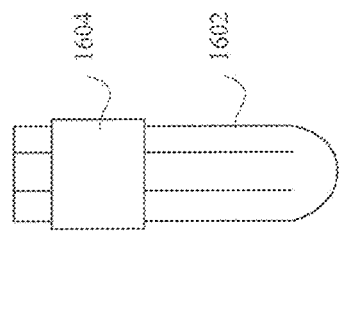
FIGS. 16A-16D show an exemplary technique for mechanically securing a gastric residence system using a small diameter capsule sleeve fitting over the gastric residence form.
Figure 16D:
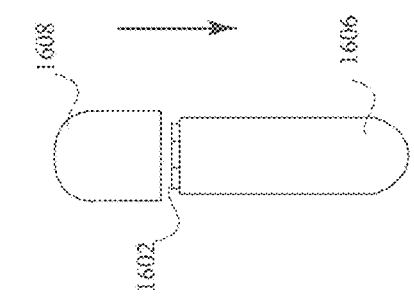
Figure 16A:
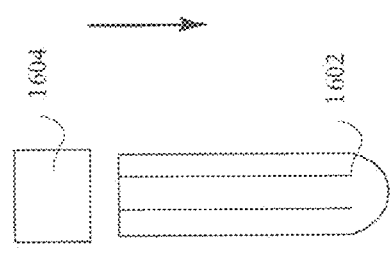
Figure 16C:
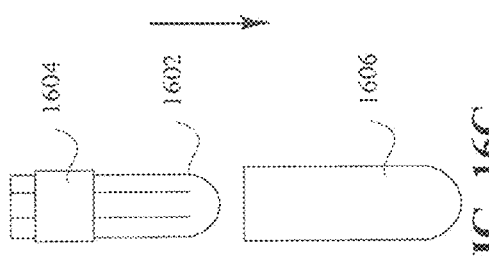

FIGS. 16A-16D show a technique for mechanically securing a gastric residence system 1602 using a small diameter capsule sleeve 1604 fitting over the gastric residence form. FIG. 16A shows that the sleeve 1604 can be secured over the extended portions of the gastric residence system but prior to actually securing the cap over the extended portions of the gastric residence system, and FIG. 16B shows the sleeve 1604 secured over the end of the gastric residence system. FIG. 16C shows the gastric residence system 1602 with capsule sleeve 1604 can be inserted into capsule body 1606 having a larger size than the sleeve 1604. In some embodiments, the end of the gastric residence system 1602 secured by sleeve 1604 can be oriented toward the opening in capsule body 1606 as illustrated. In some embodiments, the end of gastric residence system 1602 secured by sleeve 1604 can be inserted first into the opening of capsule body 1606 without departing from the scope of the present disclosure. FIG. 16D shows a slight protrusion of the gastric residence system 1602 after insertion into the capsule body 1606. In some embodiments, the length of the gastric residence system 1602 can be such that there is no protrusion of the gastric residence system beyond the opening of the capsule body 1606 without departing from the scope of the present disclosure. Finally, FIG. 16D illustrates that a cap 1608 corresponding to the size of the capsule body 1606 can be used to form a closed container containing the gastric residence system 1602. In this configuration, the sleeve 1604 can continue to provide mechanical security for the gastric residence system 1602 within the larger container formed by capsule body 1606 and cap 1608. In some embodiments, the thickness of the sleeve 1604 can provide spacing between the interior surface of the capsule and the gastric residence system. In some embodiments, the spacing between the interior surface of the capsule and the gastric residence system can be determined by the thickness of the sleeve 1604. In some embodiments, a preferred minimum thickness for the sleeve 1604 can be at least about 0.01 millimeters. In some embodiments, a preferred minimum thickness for the sleeve 1604 can be at least about 0.05 millimeters. In some embodiments, a preferred minimum thickness for the sleeve 1604 can be at least about 0.1 millimeters. In some embodiments, a preferred minimum thickness for the sleeve 1604 can be at least about 0.2 millimeters. Alternatively, an excessively thick sleeve 1604 can result in significant wasted space within the container. In some embodiments, a preferred maximum thickness of the sleeve 1604 can be at most 0.1 millimeters. In some embodiments, a preferred maximum thickness of the sleeve 1604 can be at most 0.2 millimeters. In some embodiments, a preferred maximum thickness of the sleeve 1604 can be at most 0.5 millimeters.

As stated above regarding FIGS. 13A-16D, in addition to encapsulation, a sleeve, band, or cap, according to examples of the disclosure can be used to assist in preventing premature release of the gastric residence in a user's esophagus prior to reaching the user's stomach. One aspect of preventing premature release of the gastric residence system in the user's esophagus is mechanical support provided by the sleeve, band, or cap against the forces exerted by a folded gastric residence system pressing outwardly to return to a non-folded configuration. Another aspect of preventing premature release of the gastric residence system in the user's esophagus is that the sleeve, band, or ring must still allow the gastric residence system to deploy once the gastric environment is reached, and thus must dissolved before the gastric residence system exits the stomach in an folded or compacted form. As described above, the thickness of a sleeve (e.g., as described with regard to FIGS. 16A-16D above), band (e.g., as described with regard to FIG. 13A-13B above), or cap (e.g., as described with regard to FIGS. 14 and 15A-15D above), can be varied to achieve desired mechanical and/or dissolution characteristics. Other physical dimensions of the cap, band, or sleeve can also be varied to achieve desired mechanical and/or dissolution characteristics, such as the length of the cap, band or sleeve. In addition, sleeves, bands, or caps comprised of different materials can be used to achieve desired mechanical and dissolution characteristics.

One aspect of assisting in preventing premature release of the gastric residence system is withstanding mechanical forces exerted by the gastric residence system on the sleeve, band, or cap. In order to be able to maintain the gastric residence system in a folded position, the sleeve, band, or cap must be able to withstand a circumferential stress (e.g., a hoop stress or cylinder stress) from a folded gastric residence system that is equal to or in excess (e.g., by about 50% or about 100%) of the bending force used to place the gastric residence system into the folded position. By being able to withstand the amount of circumferential stress exerted by the folded gastric residence system, the sleeve, band, or cap can assist in preventing premature release of the gastric residence system in a user's esophagus. In some embodiments, the sleeve, band, or cap can preferably withstand a circumferential stress from a folded gastric residence system of at least about 0.1 newtons. In some embodiments, the sleeve, band, or cap can preferably withstand a circumferential stress from a folded gastric residence system of at least about 0.15 newtons. In some embodiments, the sleeve, band, or cap can preferably withstand a circumferential stress from a folded gastric residence system of at least about 0.2 newtons. In some embodiments, the sleeve, band, or cap can preferably withstand a circumferential stress from a folded gastric residence system of at least about 0.3 newtons. In some embodiments, the sleeve, band, or cap can preferably withstand a circumferential stress from a folded gastric residence system of at least about 0.4 newtons. In some embodiments, the sleeve, band, or cap can preferably withstand a circumferential stress from a folded gastric residence system of at least about 0.6 newtons. In some embodiments, the sleeve, band, or cap can preferably withstand a circumferential stress from a folded gastric residence system of at least about 1.5 newtons. In some embodiments, the sleeve, band, or cap can preferably withstand a circumferential stress from a folded gastric residence system of at least about 2.25 newtons. In some embodiments, the sleeve, band, or cap can preferably withstand a circumferential stress from a folded gastric residence system of at least about 3 newtons. In some embodiments, the sleeve, band, or cap can preferably withstand a circumferential stress from a folded gastric residence system of at most about 2 newtons. In some embodiments, the sleeve, band, or cap can preferably withstand a circumferential stress from a folded gastric residence system of at most about 3 newtons. In some embodiments, the sleeve, band, or cap can preferably withstand a circumferential stress from a folded gastric residence system of at most about 4 newtons. In some embodiments, the sleeve, band, or cap can preferably withstand a circumferential stress from a folded gastric residence system of at most about 6.5 newtons. In some embodiments, the sleeve, band, or cap can preferably withstand a circumferential stress from a folded gastric residence system of at most about 10 newtons. In some embodiments, the sleeve, band, or cap can preferably withstand a circumferential stress from a folded gastric residence system of at most about 20 newtons. In some embodiments, the sleeve, band, or cap can preferably withstand a circumferential stress from a folded gastric residence system of at most about 40 newtons. In some embodiments, the sleeve, band, or cap can preferably withstand a circumferential stress from a folded gastric residence system of at most about 100 newtons.

While the sleeve, band, or cap can assist in preventing release of the gastric residence system in a user's esophagus prior to reaching the gastric environment, the sleeve, cap, band, or retaining sleeve can also affect the total amount of time for the gastric residence system to deploy once the environment of the gastric environment is reached. At the same time, the sleeve, band, or cap should allow the release of the gastric residence system once it reaches the gastric environment and should not hold the gastric residence system in the compacted form long enough to be able to exist the stomach. Accordingly, the sleeve, band, or cap can be designed to prevent release of the gastric residence system in the user's esophagus while also allowing the gastric residence system to release and unfold once the gastric environment is reached. In some embodiments, a cap, band, sleeve, or retaining cap can be designed to allow deployment of the gastric residence system within a specified amount of time in a gastric environment. The deployment time for the gastric residence system can be designed in terms of a combined deployment time of the outer capsule and the cap, band, sleeve, or retaining cap in combination. In some embodiments, the amount of time designed for the cap, band, sleeve, or retaining cap to allow deployment (e.g., as a result of the band, cap, or sleeve being dissolved by the acidic gastric environment) of the gastric residence system can be an amount of time for the gastric residence system to deploy from the folded position in a gastric environment while being held only by the cap, band, sleeve or retaining cap without an outer capsule present (e.g., after the outer capsule has completely dissolved in the gastric environment).

In some embodiments, the sleeve, band, or cap can be designed such that the gastric residence system does not deploy before reaching the gastric environment, but releases relatively quickly once reaching the gastric environment. In some embodiments, the sleeve, band, or cap can preferably allow deployment of the gastric residence system in a gastric environment within at most about 5 seconds. In some embodiments, the sleeve, band, or cap can preferably allow deployment of the gastric residence system in a gastric environment within at most about 10 seconds. In some embodiments, the sleeve, band, or cap can preferably allow deployment of the gastric residence system in a gastric environment within at most about 30 seconds. In some embodiments, the sleeve, band, or cap can preferably allow deployment of the gastric residence system in a gastric environment within at most about 1 minute. In some embodiments, the sleeve, band, or cap can preferably allow deployment of the gastric residence system in a gastric environment within at most about 2 minutes. In some embodiments, the sleeve, band, or cap can preferably allow deployment of the gastric residence system in a gastric environment within at most about 4 minutes. In some embodiments, the sleeve, band, or cap can preferably allow deployment of the gastric residence system in a gastric environment within at most about 8 minutes. In some embodiments, the sleeve, band, or cap can preferably allow deployment of the gastric residence system in a gastric environment within at most about 12 minutes.

In some embodiments, the sleeve, band, or cap can be designed such that it does not release immediately after reaching the gastric environment in order to further ensure that the gastric residence system does not release prior to entering the gastric environment. In some embodiments, the sleeve, band, or cap can preferably allow deployment of the gastric residence system in a gastric environment after at least about 5 seconds. In some embodiments, the sleeve, band, or cap can preferably allow deployment of the gastric residence system in a gastric environment after at least about 10 seconds. In some embodiments, the sleeve, band, or cap can preferably allow deployment of the gastric residence system in a gastric environment after at least about 30 seconds. In some embodiments, the sleeve, band, or cap can preferably allow deployment of the gastric residence system in a gastric environment after at least about 1 minute. In some embodiments, the sleeve, band, or cap can preferably allow deployment of the gastric residence system in a gastric environment after at least about 2 minutes. In some embodiments, the sleeve, band, or cap can preferably allow deployment of the gastric residence system in a gastric environment after at least about 4 minutes. In some embodiments, the sleeve, band, or cap can preferably allow deployment of the gastric residence system in a gastric environment after at least about 8 minutes.

In some embodiments, the amounts of time described directly above for deployment of the gastric residence system in the gastric environment can be based on the retention of the gastric residence system by a sleeve, band, or cap alone. In such embodiments, an outer capsule enclosing the gastric residence system retained by the sleeve, band, or cap would add additional time to the total deployment time of the gastric residence system in the gastric environment. In some embodiments, the deployment time can be designed with a consideration of the amount of time to dissolve both the outer capsule (e.g., the container as described herein) and the sleeve, band, or cap in the gastric environment.

In some embodiments, the sleeve, band, or cap can be designed such that the gastric residence system does not deploy before reaching the gastric environment, but releases relatively quickly once reaching the gastric environment. In some embodiments, the outer capsule in combination with the sleeve, band, or cap can preferably allow deployment of the gastric residence system in a gastric environment within at most about 5 seconds. In some embodiments, the outer capsule in combination with the sleeve, band, or cap can preferably allow deployment of the gastric residence system in a gastric environment within at most about 10 seconds. In some embodiments, the outer capsule in combination with the sleeve, band, or cap can preferably allow deployment of the gastric residence system in a gastric environment within at most about 30 seconds. In some embodiments, the outer capsule in combination with the sleeve, band, or cap can preferably allow deployment of the gastric residence system in a gastric environment within at most about 1 minute. In some embodiments, the outer capsule in combination with the sleeve, band, or cap can preferably allow deployment of the gastric residence system in a gastric environment within at most about 2 minutes. In some embodiments, the outer capsule in combination with the sleeve, band, or cap can preferably allow deployment of the gastric residence system in a gastric environment within at most about 4 minutes. In some embodiments, the outer capsule in combination with the sleeve, band, or cap can preferably allow deployment of the gastric residence system in a gastric environment within at most about 8 minutes. In some embodiments, the outer capsule in combination with the sleeve, band, or cap can preferably allow deployment of the gastric residence system in a gastric environment within at most about 12 minutes.

In some embodiments, the outer capsule in combination with the sleeve, band, or cap can be designed such that it does not release immediately after reaching the gastric environment in order to further ensure that the gastric residence system does not release prior to entering the gastric environment. In some embodiments, the outer capsule in combination with the sleeve, band, or cap can preferably allow deployment of the gastric residence system in a gastric environment after at least about 5 seconds. In some embodiments, the outer capsule in combination with the sleeve, band, or cap can preferably allow deployment of the gastric residence system in a gastric environment after at least about 10 seconds. In some embodiments, the outer capsule in combination with the sleeve, band, or cap can preferably allow deployment of the gastric residence system in a gastric environment after at least about 30 seconds. In some embodiments, the outer capsule in combination with the sleeve, band, or cap can preferably allow deployment of the gastric residence system in a gastric environment after at least about 1 minute. In some embodiments, the outer capsule in combination with the sleeve, band, or cap can preferably allow deployment of the gastric residence system in a gastric environment after at least about 2 minutes. In some embodiments, the outer capsule in combination with the sleeve, band, or cap can preferably allow deployment of the gastric residence system in a gastric environment after at least about 4 minutes. In some embodiments, the outer capsule in combination with the sleeve, band, or cap can preferably allow deployment of the gastric residence system in a gastric environment after at least about 8 minutes.

Figure 17B:
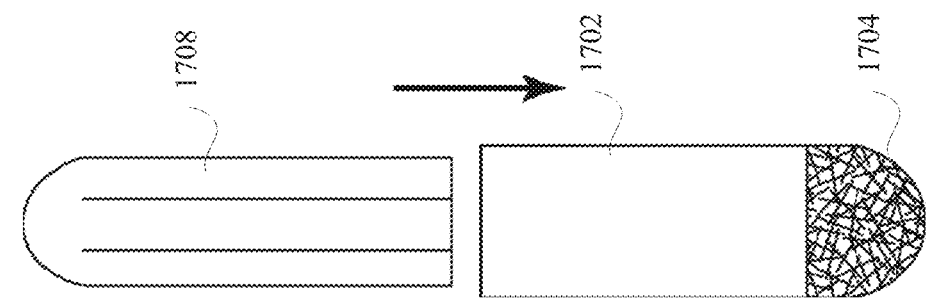
FIGS. 17A-17D show an exemplary technique for mechanically securing a gastric residence system using a non-aqueous gel loaded into a capsule body prior to insertion of the gastric residence system into the capsule body.
Figure 17A:
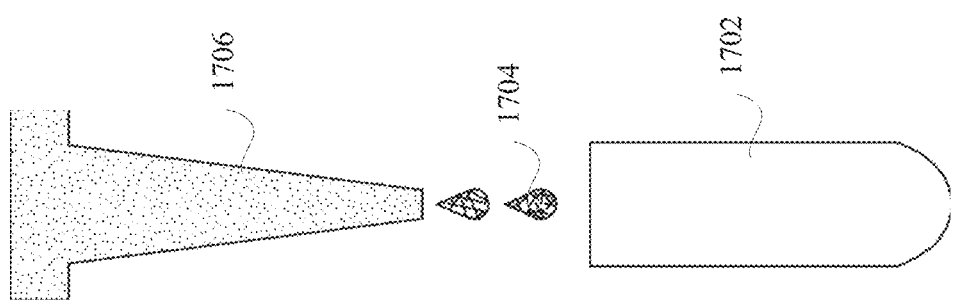
Figure 17D:
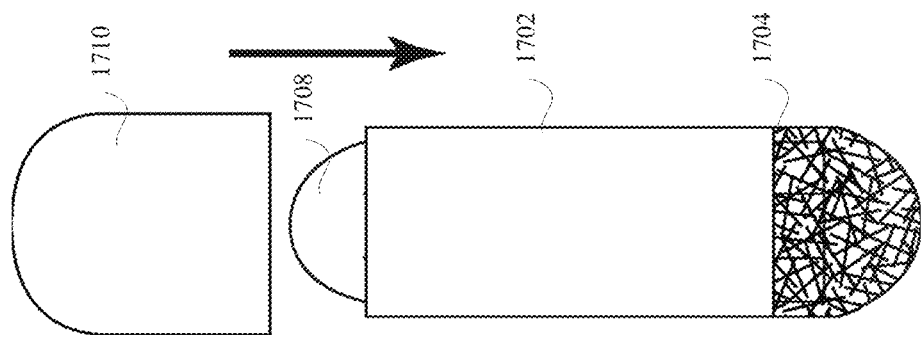
Figure 17C:
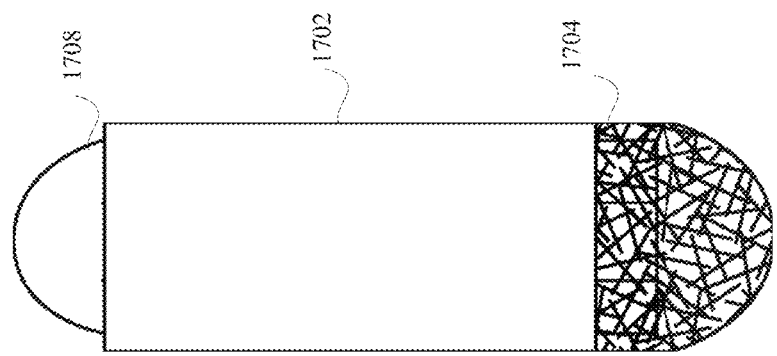

FIGS. 17A-17D show a technique for mechanically securing a gastric residence system 1708 using a non-aqueous gel 1704 loaded into a capsule body 1702 prior to insertion of the gastric residence system into the capsule body. FIG. 17A shows a dispenser 1706 for dispensing the non-aqueous gel 1704 into the capsule body 1702 prior to insertion of a gastric residence system into the capsule body. The non-aqueous gel 1704 can be selected so that it does not disturb or dissolve the capsule material 1702. Further, the non-aqueous gel 1704 can be selected so that it dissolves at a controlled rate in the stomach environment to allow for deployment of the gastric residence system into the uncompacted form at the proper time. FIG. 17B illustrates the gastric residence system 1708 being inserted into the capsule body 1702 in the compacted form. FIG. 17C shows the gastric residence system 1708 after insertion into the capsule body 1702, where the extended portions of the gastric residence system can be inserted into a small pool of the of the non-aqueous gel 1704 at the bottom of the capsule body. The non-aqueous gel 1704 can thereafter set and act as a non-permanent glue for securing the extended portions of the gastric residence system 1708 together to mechanically constrain the gastric residence system in the compacted form. FIG. 17D shows a cap 1710 installed on the capsule body 1702 to form a completed contain for the gastric residence system.

Figure 18B:
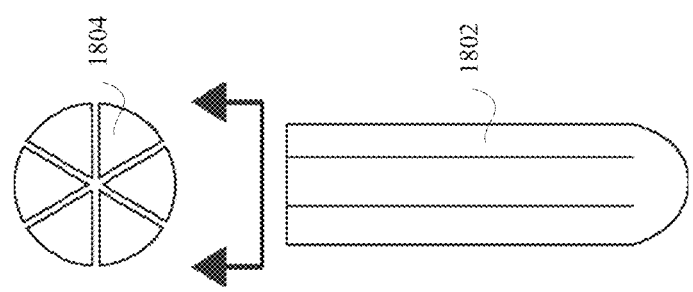
Figure 18A:
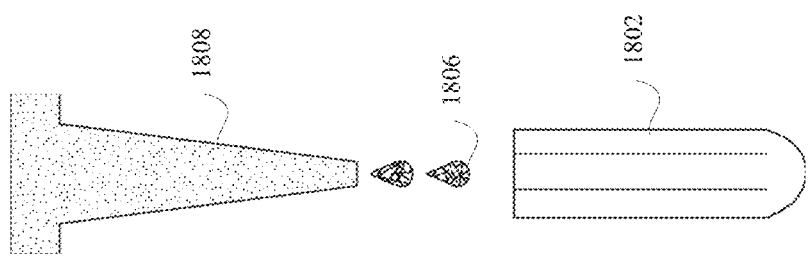

FIGS. 18A-18E show a technique for mechanically securing a gastric residence system 1802 using a non-aqueous gel 1806 applied to extended portions 1804 of the gastric residence system prior to insertion of the gastric residence system in a capsule body 1810. FIG. 18A illustrates two views of a gastric residence system according to examples of the disclosure. The first view of gastric residence system 1802 illustrates a side view of a compacted gastric residence system where the extended portions have been brought in close proximity together. The second view of gastric residence system 1802 shows distal ends of extended portions 1804 from a top-down view relative to the orientation shown in the first view. As shown, there can be gaps between the extended portions 1804 in the compacted form. In some embodiments, a preferred minimum spacing for the gaps can be at least about 0.01 millimeters In some embodiments, a preferred minimum spacing for the gaps can be at least about 0.05 millimeters. In some embodiments, a preferred minimum spacing for the gaps can be at least about 0.1 millimeters. In some embodiments, a preferred maximum spacing for the gaps can be at most about 0.5 millimeters. In some embodiments, a preferred maximum spacing for the gaps can be at most about 0.25 millimeters. FIG. 18B shows that a non-aqueous gel 1806 can be dispensed onto the distal ends of extended portions 1804 by a dispenser 1808 such that the non-aqueous gel can penetrate into the spaces between extended portions 1804 of the gastric residence system 1802. FIG. 18C shows the non-aqueous gel 1806 after application that has penetrated into the gaps between the extended portions 1804. FIG. 18D shows the insertion of the gastric residence system into capsule body 1810. FIG. 18E shows side and top views of the inserted gastric residence system 1802 into the capsule body 1810. As can be seen from the top view, the gaps between distal ends of the extended portions 1804 can be filled with the non-aqueous gel 1806 for mechanically securing the extended portions of the gastric residence system. A cap can thereafter be attached to the capsule body 1810 to form a completed container (not shown).

Figure 19B:
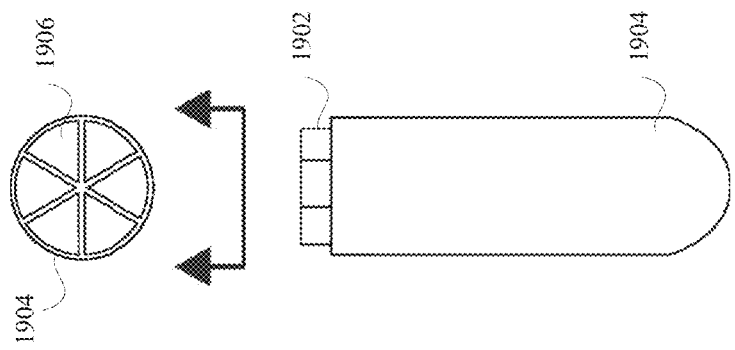
Figure 19A:
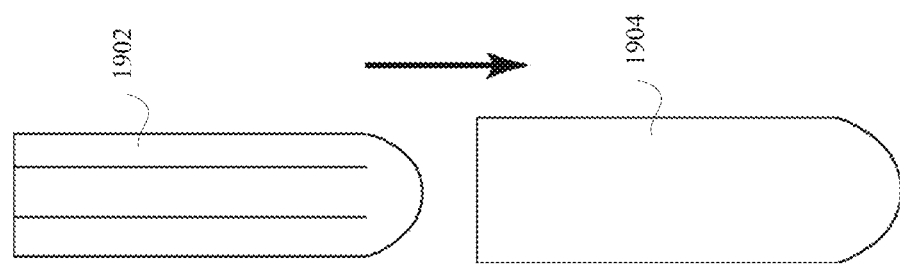

FIGS. 19A-19D show a technique for mechanically securing a gastric residence system 1902 using a non-aqueous gel 1908 applied to extended portions 1904 of the gastric residence system after insertion of the gastric residence system in a capsule body 1910. The technique is generally analogous to the process shown in FIGS. 18A-18E, except that the step of inserting the gastric residence system 1902 into the capsule body 1904 occurs prior to application of the non-aqueous gel as shown in FIGS. 19A-19B. FIG. 19C shows application of the non-aqueous gel to the distal ends of extended portions of gastric residence system 1902 after insertion into the capsule body 1904. FIG. 19D shows that the end result can be appear generally the same as the end result as shown in FIG. 18E, where the non-aqueous gel 1908 occupies the gaps between extended portions of the gastric residence system contained within the capsule body 1904. A cap can thereafter be attached to the capsule body 1904 to form a completed container (not shown).

EXAMPLES

In an experimental test to determine the effects of a cap, band, or sleeve on deployment time of a stellate gastric residence system in an aqueous environment, the deployment time of encapsulated stellate gastric residence system according to examples of the disclosure was measured in a pH 3.0 phosphate buffered saline solution. The buffer was prepared by dissolving 1.36 grams of monobasic potassium phosphate, anhydrous, and 8.41 grams of sodium chloride in water and adjusting to pH 3.0 with hydrochloric acid, before making to 1 liter. Three configurations were tested in the experiment, and each configuration had three samples tested. In each of the three configurations, the gastric residence system was enclosed within capsugel's VCaps Plus HPMC 00EL outer capsule. The three configurations were as follows: 1) a size 0EL cap from Capsugel's VCaps Plus 0EL capsule was placed over the folded legs of the stellate gastric residence system before insertion into the body of the 00EL capsule with the capped end of the stellate gastric residence system inserted first into the opening of the 00EL capsule and subsequently capped with a 00EL cap to form a completely container, 2) a sleeve formed by cutting a bottom ⅓ portion of a cap from Capsugel's VCaps Plus 0EL capsule was placed over the folded legs of the stellate gastric residence system before insertion into the body of the 00EL capsule and subsequently capped with a 00EL cap to form a complete container, 3) an uncapped folded stellate gastric residence system was inserted into the body of the 00EL capsule and subsequently capped with a 00EL cap to form a complete container. The size 00EL capsules containing a stellate gastric residence system encapsulated in one of the three configurations was placed in a 450 mL glass jar with 35 mL of the pH 3.0 solution. The glass jars measured 80 millimeters in diameter by 94 millimeters in height and had a PTFE-lined lid. The dosage forms were placed in the jars and the jars were sealed, inverted, and immediately placed on a laboratory rocker set at 30 cycles per minute. The measurement time was started when the capsule was inserted into the pH 3 solution. The jars were observed visually and the timer was stopped when the dosage form deployed. The three examples below describe the results of three trials each for each of the three configurations described above.

Example 1: Encapsulated Gastric Residence System with a Cap Retaining Element

The contents of the 00EL outer capsule in the first configuration a stellate gastric residence system with a cap from Capsugel's VCaps Plus 0EL cap (e.g., such as cap 1504 in FIG. 15A-15D above) over the end of the extended folded legs of a stellate gastric residence system (e.g., as illustrated by cap 1504 in FIGS. 15A-15D above). In the first configuration, the capped stellate was inserted with the capped end first into the outer 00EL capsule before the 00EL cap was used to close the 00EL capsule to form a complete container. Table 3 below lists the deployment times for three trials where timing began when the 00EL capsule was placed into the pH 3 solution and timing ended when the legs of the stellate gastric residence system deployed.

TABLE 3

| Group | Sleeve | Sample ID | Deployment (min) | Average Time (min) |
|---|---|---|---|---|
| Capsule + Cap | 0EL Cap | 1 | 7.4 | 7.4 |
|  |  | 2 | 10.2 |  |
|  |  | 3 | 4.53 |  |

For the three trials, the average time for deployment of the stellate gastric residence system from the combination of the 00EL capsule and the additional 0EL cap was 7.4 minutes.

Example 2: Encapsulated Gastric Residence System with a Sleeve Retaining Element The contents of the 00EL outer capsule in the second configuration was a stellate gastric residence system with a sleeve surrounding the extended folded legs of the gastric residence system and positioned near distal ends of the stellate gastric residence system legs (e.g., as illustrated by retaining band 1304 in FIG. 13A and sleeve 1604 in FIGS. 16A-16D above). In the second configuration, the distal end of the stellate surrounded by the sleeve was inserted into the 00EL outer capsule before the 00EL capsule cap was installed to form a complete container. In the second configuration, the sleeve was made by cutting a bottom ¼-⅓ portion (approximately 3 millimeters in height) of a same type of size 0EL cap (approximately 11 millimeters in height) used as the cap in the first configuration. Table 4 below lists the deployment times for three trials where timing began when the 00EL capsule was placed into the pH 3 solution and timing ended when the legs of the stellate gastric residence system deployed.

TABLE 4

| Group | Sleeve | Sample ID | Deployment (min) | Average Time (min) |
|---|---|---|---|---|
| Capsule + Sleeve | Cut Ring from 0EL Cap | 4 | 5.22 | 5.9 |
|  |  | 5 | 6.07 |  |
|  |  | 6 | 6.30 |  |

For the second configuration, the average time for deployment of the stellate gastric residence system from the combination of the 00EL capsule and the additional 0EL sleeve formed from a bottom ⅓ portion of a 0EL cap was 5.9 minutes.

Example 3: Encapsulated Gastric Residence System with No Additional Retaining Element The contents of the 00EL outer capsule in the third configuration was an uncapped/unsleeved gastric residence system inserted directly into the 00EL outer capsule (e.g., as shown in FIG. 8B). Table 5 below illustrates the results of the three experiments in the third configuration.

TABLE 5

| Group | Sleeve | Sample ID | Deployment (min) | Average Time (min) |
|---|---|---|---|---|
| Capsule only | None | 7 | 2.28 | 2.6 |
| | | 8 | 2.63 | |
| | | 9 | 2.87 | |

In the example of Table 5, the average time for deployment of the gastric residence system was 2.6 minutes in the third configuration without a sleeve or cap. The 2.6 minute average deployment time was lower than the average times for both the first and second configurations which utilized a cap and a sleeve, respectively. In addition, the second configuration that utilized a sleeve had a lower average time for deployment of the gastric residence system of 5.6 minutes compared with the first configuration using a full cap over the extended portions of the gastric residence system.

The invention is further illustrated by the following non-limiting examples.

Some examples of the disclosure are directed to a method for encapsulating a compactable gastric residence system including a linking member linking one or more segments comprising: receiving the compactable gastric residence system in an uncompacted form; orienting the compactable gastric residence system into a compacting position; compacting the compactable gastric residence system into a compacted form; and inserting the compactable gastric residence system in the compacted form into an opening of a container. Additionally or alternatively to one or more of the examples disclosed above, in some examples, the compactable gastric residence system the one or more segments comprise a plurality of elongate members, each elongate member having its proximal end attached to the linking member and each elongate member having its distal end not attached to the linking member and located at a larger radial distance from the linking component than the proximal end.

Additionally or alternatively to one or more of the examples disclosed above, in some examples, compacting the compactable gastric residence system into the compacted form comprises reducing a distance between the distal ends of each elongate member. Additionally or alternatively to one or more of the examples disclosed above, in some examples, compacting the compactable gastric residence system into the compacted form comprises causing the distal ends of each elongate member to come together. Additionally or alternatively to one or more of the examples disclosed above, in some examples, the compactable gastric residence system has an elastic characteristic that causes the compactable gastric residence system to configure in the uncompacted form when no external force is applied to the compactable gastric residence system.

Additionally or alternatively to one or more of the examples disclosed above, in some examples, orienting the compactable gastric residence system includes securing a portion of the linking member with a vacuum cup. Additionally or alternatively to one or more of the examples disclosed above, in some examples, a shape of at least a portion of the linking member is configured to mate with the vacuum cup. Additionally or alternatively to one or more of the examples disclosed above, in some examples, orienting the compactable gastric residence system comprises securing the compactable gastric residence system with a pneumatic clamp. Additionally or alternatively to one or more of the examples disclosed above, in some examples, reducing a distance between the distal ends of each elongate member comprises applying a force to the linking member and causing the linking member and plurality of elongate members to pass through an aperture. Additionally or alternatively to one or more of the examples disclosed above, in some examples, the aperture has a radius smaller than a radius of an opening of the container.

Additionally or alternatively to one or more of the examples disclosed above, in some examples, the aperture is located at an end of a tapered enclosure, wherein a force applied by the tapered enclosure causes the extended members of the compactable gastric residence system to compress into the compacted form. Additionally or alternatively to one or more of the examples disclosed above, in some examples, inserting the compactable gastric residence system in the compacted form into the container comprises aligning the container with the aperture and receiving the compactable gastric residence system as it is pressed through the aperture. Additionally or alternatively to one or more of the examples disclosed above, in some examples, applying the force to the linking member causes the compactable gastric residence system to partially enter the container and the method further comprises applying a second force to the distal ends of the elongate members of the compactable gastric residence system until the entire compactable gastric residence system passes through the aperture. Additionally or alternatively to one or more of the examples disclosed above, in some examples, the force is applied by a first object, and the second first is applied by a second object larger than the first object. Additionally or alternatively to one or more of the examples disclosed above, in some examples, reducing a distance between the distal ends of each elongate member comprises: reducing a distance between distal ends of elongate members belonging to a first group of the plurality of elongate members; reducing a distance between distal ends of elongate members belonging to a second group of the plurality of the elongate members; and thereafter reducing a distance between distal ends of elongate members belong to the first group and distal ends of the elongate members belong to the second group.

Additionally or alternatively to one or more of the examples disclosed above, in some examples, after passing through the aperture, a partial portion of the compactable gastric residence system extends beyond the opening of the container. Additionally or alternatively to one or more of the examples disclosed above, in some examples the method further comprises securing a retaining fixture to the compactable gastric residence system configured to resist expansion of the compactable gastric residence system from the compacted form to the uncompacted form. Additionally or alternatively to one or more of the examples disclosed above, in some examples, the retaining fixture couples to the distal ends of each of the elongate members of the compactable gastric residence system. Additionally or alternatively to one or more of the examples disclosed above, in some examples the method further comprises applying a cap to the container to create a sealed enclosure containing the compactable gastric residence system. Additionally or alternatively to one or more of the examples disclosed above, in some examples, an outer radius of the retaining fixture is smaller than an inner radius of the enclosed structure such that a gap is formed between the retaining fixture and the enclosed structure.

Additionally or alternatively to one or more of the examples disclosed above, in some examples, the gap between the outer radius of the retaining fixture and the inner radius of the enclosed structure has a minimum size of at least about 0.01 millimeters, at least about 0.05 millimeters, at least about 0.075 millimeters, or at least about 0.1 millimeters. Additionally or alternatively to one or more of the examples disclosed above, in some examples, the gap between the outer radius of the retaining fixture and the inner radius of the enclosed structure has a maximum size of about 0.15 millimeters, about 0.2 millimeters, or about 0.25 millimeters. Additionally or alternatively to one or more of the examples disclosed above, in some examples, the retaining fixture is configured to maintain a spacing between the elongate members of the compactable gastric residence system in the compressed form. Additionally or alternatively to one or more of the examples disclosed above, in some examples, the spacing between the elongate members of the compactable gastric residence system in the compressed form has a minimum size of about 0.01 millimeters, 0.05 millimeters, about 0.75 millimeters, or about 0.1 millimeters. Additionally or alternatively to one or more of the examples disclosed above, in some examples, the spacing between the elongate members of the compactable gastric residence system in the compressed form has a maximum size of about 0.15 millimeters, about 0.125 millimeters, about 0.1 millimeters, or about 0.05 millimeters. Additionally or alternatively to one or more of the examples disclosed above, in some examples, the linking member is an elastomer. Additionally or alternatively to one or more of the examples disclosed above, in some examples, the container is a half-capsule. Additionally or alternatively to one or more of the examples disclosed above, in some examples, the enclosed structure is a capsule. Additionally or alternatively to one or more of the examples disclosed above, in some examples, a force for maintaining the compactable gastric residence system in the compressed form is at least 0.2 newtons.

Some examples of the disclosure are directed to a system for encapsulating a compactable gastric residence system including a linking member linking one or more segments comprising: a compacting system; and an encapsulator configured to encapsulate the compacted gastric residence system, wherein the compacting system is mechanically linked to the encapsulator and configured to repetitively compact and encapsulate a plurality of compactable gastric residence systems. Additionally or alternatively to one or more of the examples disclosed above, in some examples, the compacting system includes a vibratory bowl feeder configured to convey the plurality of gastric residence systems toward the encapsulator. Additionally or alternatively to one or more of the examples disclosed above, in some examples, the vibratory bowl feeder orients a gastric residence system into a vertical orientation configured to be received by the encapsulator.

Additionally or alternatively to one or more of the examples disclosed above, in some examples, the compacting system includes a gripping arm configured to engage with the compactable gastric residence system and orient the gastric residence system in position for compacting and encapsulation. Additionally or alternatively to one or more of the examples disclosed above, in some examples, the compacting system includes a gripping arm configured to engage with the compactable gastric residence system and orient the gastric residence system in position for compacting and encapsulation. Additionally or alternatively to one or more of the examples disclosed above, in some examples, the gripping arm comprises a robotic arm having a vacuum cup at a first distal end, the vacuum cup configured to grip a portion of the compactible gastric residence system. Additionally or alternatively to one or more of the examples disclosed above, in some examples, the gripping arm comprises an expandable head configured to grip by expanding within a flexible opening of the gastric residence system.

Additionally or alternatively to one or more of the examples disclosed above, in some examples, the compacting system comprises: a plurality of rotating hinges, each hinge including a vacuum cup for engaging with an elongate member of the gastric residence system; and a folding mechanism for simultaneously rotating the hinges, thereby folding each of the elongate members into the compacted form of the gastric residence system. Additionally or alternatively to one or more of the examples disclosed above, in some examples, each vacuum cup for engaging with the elongate members secures a respective elongate member to the compacting system while the hinges are rotated. Additionally or alternatively to one or more of the examples disclosed above, in some examples, the encapsulator comprises a piston configured to press the compactible gastric residence in the compacted form into an opening of a container. Additionally or alternatively to one or more of the examples disclosed above, in some examples, the container is a half-capsule.

Some examples of the disclosure are directed to a compactable gastric residence system including a linking member linking one or more segments having a compacted form and an uncompacted form, wherein: the compactable gastric residence system has an elastic characteristic that causes the compactable gastric residence system to configure in the uncompacted form when no external force is applied to the compactable gastric residence system; the compactable gastric residence system is configured to be gripped at a first portion; the compactable gastric residence system is configured to be folded into the compacted form; the compacted form of the compacted device is configured to be inserted into an opening of a container; and the compactable gastric residence system is further secured in the compacted form by a retaining fixture coupled to a distal end of the compactable gastric residence system.

Some examples of the disclosure are directed to a method for encapsulating a plurality of compactable gastric residence system including a linking member linking one or more segments comprising: receiving a cartridge containing the plurality of gastric residence systems in a compacted form; and sequentially inserting the plurality of compactable gastric residence system in the compacted form into an opening of a respective container by a continuous application of force to one of the plurality of gastric residence systems in the container. Additionally or alternatively to one or more of the examples disclosed above, in some examples, a time between successive insertions in the sequential insertion of the plurality of gastric residence systems into a container is less than 15 seconds. Additionally or alternatively to one or more of the examples disclosed above, in some examples, a time between successive insertions in the sequential insertion of the plurality of gastric residence systems into a container is less than 5 seconds. Additionally or alternatively to one or more of the examples disclosed above, in some examples, a time between successive insertions in the sequential insertion of the plurality of gastric residence systems into a container is less than 0.5 seconds. Additionally or alternatively to one or more of the examples disclosed above, in some examples, a time between successive insertions in the sequential insertion of the plurality of gastric residence systems into a container is 0.1 seconds.

Some examples of the disclosure are directed to a system for encapsulating a compactible gastric residence system having a compacted form and an uncompacted form comprising: the compactible gastric residence system in the compacted form, a retaining element configured to resist an outward mechanical force from the compacted gastric residence system, and a container comprising a sealed enclosure that contains the compacted gastric residence and the retaining element within the sealed enclosure. Additionally or alternatively to one or more of the examples disclosed above, in some examples, the retaining element can withstand a circumferential stress of at least about 0.1 newtons, at least about 0.15 newtons, at least about 0.2 newtons, at least about 0.3 newtons, at least about 0.4 newtons, at least about 0.6 newtons, at least about 1.5 newtons, at least about 2.25 newtons, or at least about 3 newtons. Additionally or alternatively to one or more of the examples disclosed above, in some examples, the retaining element can withstand a circumferential stress of at most about 2 newtons, at most about 3 newtons, at most about 4 newtons, at most about 6.5 newtons, at most about 10 newtons, at most about 20 newtons, at most about 40 newtons, at most about 60 newtons, or at most about 100 newtons. Additionally or alternatively to one or more of the examples disclosed above, in some examples, the retaining element releases the compactible residence system from its compacted form in a gastric environment within at most about 5 seconds, within at most about 10 seconds, within at most about 30 seconds, within at most about 1 minute, within at most about 2 minutes, within at most about 4 minutes, within at most about 8 minutes, or within at most about 12 minutes. Additionally or alternatively to one or more of the examples disclosed above, in some examples, the retaining element releases the compactible residence system from its compacted form in a gastric environment after at least about 5 seconds, after at least about 10 seconds, after at least about 30 seconds, after at least about 1 minute, after at least about 2 minutes, after at least about 4 minutes, or after at least about 8 minutes. Additionally or alternatively to one or more of the examples disclosed above, in some examples, a thickness of the retaining element is at least about 0.05 millimeters, at least about 0.1 millimeters, or at least about 0.2 millimeters. Additionally or alternatively to one or more of the examples disclosed above, in some examples, a thickness of the retaining element is at most about 0.1 millimeters, at most about 0.2 millimeters, or at most about 0.5 millimeters. Additionally or alternatively to one or more of the examples disclosed above, in some examples, the compacted gastric residence system is a folded stellate. Additionally or alternatively to one or more of the examples disclosed above, in some examples, the retaining element is a cap, band, or sleeve. Additionally or alternatively to one or more of the examples disclosed above, in some examples, Some examples of the disclosure are directed to a method of preventing premature release of a gastric residence system comprising: receiving a gastric residence system in a compacted form, securing a retaining element to the gastric residence system, wherein the retaining element is configured to resist an outward mechanical force from the compacted gastric residence system, and enclosing the gastric residence system secured by the retaining element within a sealed enclosure of a container. Additionally or alternatively to one or more of the examples disclosed above, in some examples, the retaining element can withstand a circumferential stress of at least about 0.1 newtons, at least about 0.15 newtons, at least about 0.2 newtons, at least about 0.3 newtons, at least about 0.4 newtons, at least about 0.6 newtons, at least about 1.5 newtons, at least about 2.25 newtons, or at least about 3 newtons. Additionally or alternatively to one or more of the examples disclosed above, in some examples, the retaining element can withstand a circumferential stress of at most about 2 newtons, at most about 3 newtons, at most about 4 newtons, at most about 6.5 newtons, at most about 10 newtons, at most about 20 newtons, at most about 40 newtons, at most about 60 newtons, or at most about 100 newtons. Additionally or alternatively to one or more of the examples disclosed above, in some examples, the retaining element releases the compactible residence system from its compacted form in a gastric environment within at most about 5 seconds, within at most about 10 seconds, within at most about 30 seconds, within at most about 1 minute, within at most about 2 minutes, within at most about 4 minutes, within at most about 8 minutes, or within at most about 12 minutes. Additionally or alternatively to one or more of the examples disclosed above, in some examples, the retaining element releases the compactible residence system from its compacted form in a gastric environment after at least about 5 seconds, after at least about 10 seconds, after at least about 30 seconds, after at least about 1 minute, after at least about 2 minutes, after at least about 4 minutes, or after at least about 8 minutes. Additionally or alternatively to one or more of the examples disclosed above, in some examples, a thickness of the retaining element is at least about 0.05 millimeters, at least about 0.1 millimeters, or at least about 0.2 millimeters. Additionally or alternatively to one or more of the examples disclosed above, in some examples, a thickness of the retaining element is at most about 0.1 millimeters, at most about 0.2 millimeters, or at most about 0.5 millimeters. Additionally or alternatively to one or more of the examples disclosed above, in some examples, the compacted gastric residence system is a folded stellate. Additionally or alternatively to one or more of the examples disclosed above, in some examples, the retaining element is a cap, band, or sleeve. Additionally or alternatively to one or more of the examples disclosed above, in some examples, The disclosures of all publications, patents, patent applications and published patent applications referred to herein by an identifying citation are hereby incorporated herein by reference in their entirety. Web sites references using "World-Wide-Web" at the beginning of the Uniform Resource Locator (URL) can be accessed by replacing "World-Wide-Web" with www.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A compacting system for compacting a gastric residence system comprising:
   a tapered tube comprising an upper circular surface;
   a primary piston configured to advance into a center of the tapered tube and through the upper circular surface; and
   a secondary piston configured to receive the primary piston when in a retracted configuration,
   wherein the primary piston is configured to apply a first force to a linking member of the gastric residence system, and the upper circular surface of the tapered tube is configured to apply a second force to a plurality of arms of the gastric residence system, causing the gastric residence system to fold, wherein each arm of the plurality of arms is attached to the linking member at a proximal end of the arm.

2. The compacting system of claim 1, wherein the secondary piston is configured to engage with the distal ends of the arms of the gastric residence system to continue pressing the gastric residence system through the tapered tube until the gastric residence system is fully folded in a compacted configuration.

3. The compacting system of claim 2, wherein the secondary piston is configured to press the gastric residence system through the tapered tube and into a container.

4. The compacting system of claim 1, wherein the upper circular surface of the tapered tube is configured to come in contact with a distal end of each arm of the plurality of arms.

5. The compacting system of claim 1, wherein an edge of the distal end of each arm rests on the upper circular surface of the tapered tube.

6. The compacting system of claim 1, wherein a bending force of the gastric residence system is at least about 0.1 newtons when the gastric residence system is in an open configuration.

7. The compacting system of claim 1, wherein a bending force of the gastric residence system is at least about 0.2 newtons when the arms of the gastric residence system are bent more than 5 degrees relative to the arms in an open configuration.

8. The compacting system of claim 1, wherein a bending force of the gastric residence system is at least about 0.2 newtons when the arms of the gastric residence system are bent more than 10 degrees relative to the arms in an open configuration.

9. The compacting system of claim 1, wherein a bending force of the gastric residence system is at least about 0.2 newtons when the arms of the gastric residence system are bent more than 45 degrees relative to the arms in an open configuration.

10. The compacting system of claim 1, wherein the upper circular surface is polished to reduce friction between the gastric residence system and the upper circular surface of the tapered tube.

11. The compacting system of claim 1, wherein the upper circular surface is coated with biocompatible fluoropolymers to reduce friction between the gastric residence system and the upper circular surface of the tapered tube.

12. The compacting system of claim 1, wherein a contact surface area of the primary piston is about 15 square millimeters.

13. The compacting system of claim 1, wherein a contact surface area of the secondary piston is larger than a contact area of the primary piston.

14. The compacting system of claim 1, wherein the tapered tube has a top opening defined by the upper circular surface, and a diameter of the top opening is about 30 to about 50 millimeters.

15. The compacting system of claim 1, wherein the tapered tube has a bottom opening opposite the top opening, and a diameter of the bottom opening is at least about 8.2 millimeters.

16. The compacting system of claim 1, wherein a taper angle of the tapered tube is about 5 to about 60 degrees.

17. The compacting system of claim 3, wherein the container is a half-capsule.

* * * * *